(12) United States Patent
Vlad et al.

(10) Patent No.: US 11,806,448 B2
(45) Date of Patent: Nov. 7, 2023

(54) FRESHENING COMPOSITIONS COMPRISING CONTROLLED RELEASE MODULATORS

(71) Applicant: Arylessence, Inc., Marietta, GA (US)

(72) Inventors: Florin-Iosif Vlad, Amandale, NJ (US); Austin Howard, Dallas, GA (US)

(73) Assignee: Arylessence, Inc., Marietta, GA (US)

( * ) Notice: Subject to any disclaimer, the term of this patent is extended or adjusted under 35 U.S.C. 154(b) by 0 days.

(21) Appl. No.: 16/524,697

(22) Filed: Jul. 29, 2019

(65) Prior Publication Data
US 2020/0038537 A1    Feb. 6, 2020

Related U.S. Application Data

(60) Provisional application No. 62/712,701, filed on Jul. 31, 2018.

(51) Int. Cl.
| | | |
|---|---|---|
| *A61L 9/01* | (2006.01) | |
| *C11B 9/00* | (2006.01) | |
| *A01N 25/00* | (2006.01) | |

(52) U.S. Cl.
CPC ............... *A61L 9/01* (2013.01); *A01N 25/00* (2013.01); *C11B 9/00* (2013.01); *C11B 9/0015* (2013.01);
(Continued)

(58) Field of Classification Search
CPC ..................................... A61L 9/01; C11B 9/00
See application file for complete search history.

(56) References Cited

U.S. PATENT DOCUMENTS

| 5,409,694 A | 4/1995 | Meyer |
| 6,716,805 B1 | 4/2004 | Sherry et al. |

(Continued)

FOREIGN PATENT DOCUMENTS

| EP | 0 520 547 A2 | 12/1992 |
| EP | 0 520 547 A3 | 12/1992 |

(Continued)

OTHER PUBLICATIONS

Vlad, Florin-Iosif; PCT Search Report and Written Opinion for PCT Application No. PCT/US2019/044102, filed Jul. 30, 2019, dated Oct. 15, 2019; 10 pages.

(Continued)

*Primary Examiner* — Arrie L Reuther
(74) *Attorney, Agent, or Firm* — RUPPERT U.S. IP GmbH; Siegfried J. W. Ruppert

(57) ABSTRACT

The present invention relates to freshening compositions, devices comprising same and methods of using same for freshening the atmosphere, the air or surfaces. Also provided are methods for manufacturing the freshening compositions and devices comprising same. Disclosed are non-glycol ether liquid freshening compositions comprising a fragrance release modulator. A freshening composition of this invention may comprise (i) from about 0.1 wt % to about 95 wt % perfume raw materials, (ii) from about 0.01 wt % to about 90 wt % fragrance release modulator, and (iii) from about 1.0 wt % to about 95 wt % solvents, diluents or a mixture thereof. Disclosed are passive and active air or surface freshening products comprising a freshening composition of the present invention that allow controlled and customized release of the freshening composition to the atmosphere, air, or onto surfaces. The addition of a fragrance release modulator to formulate a freshening composition of the present (Continued)

invention allows the modulation of the release of the freshening composition.

102 Claims, 5 Drawing Sheets

(52) U.S. Cl.
CPC .......... *C11B 9/0019* (2013.01); *C11B 9/0061* (2013.01); *C11B 9/0073* (2013.01); *A61L 2209/11* (2013.01); *A61L 2209/13* (2013.01); *A61L 2209/134* (2013.01)

(56) References Cited

U.S. PATENT DOCUMENTS

| | | | |
|---|---|---|---|
| 2002/0193281 A1 | 12/2002 | Mansfeld et al. | |
| 2003/0199402 A1 | 10/2003 | Triplett et al. | |
| 2007/0187404 A1 | 8/2007 | Caunt et al. | |
| 2008/0023569 A1 | 1/2008 | O'Leary et al. | |
| 2008/0248120 A1 | 10/2008 | Anderson et al. | |
| 2009/0202446 A1 | 8/2009 | Vlad et al. | |
| 2012/0097754 A1 | 4/2012 | Vlad et al. | |
| 2012/0328548 A1 | 12/2012 | Touitou | |
| 2014/0115765 A1 | 5/2014 | Carpenter et al. | |
| 2015/0196677 A1 | 7/2015 | Vlad et al. | |
| 2016/0089465 A1 | 3/2016 | Frankenbach et al. | |
| 2016/0367713 A1* | 12/2016 | Morgan | C11B 9/00 |
| 2016/0367715 A1* | 12/2016 | Turner | A61L 9/01 |
| 2018/0008740 A1* | 1/2018 | Morgan, III | A61L 9/01 |
| 2018/0028708 A1 | 2/2018 | Lynch et al. | |
| 2018/0064838 A1 | 3/2018 | Blondeau et al. | |
| 2018/0296716 A1 | 10/2018 | Vlad et al. | |
| 2020/0038537 A1 | 2/2020 | Vlad et al. | |

FOREIGN PATENT DOCUMENTS

| | | |
|---|---|---|
| GB | 2 358 586 A | 8/2001 |
| WO | 1991018586 | 12/1991 |
| WO | WO2016/180893 A1 | 11/2016 |
| WO | WO2016/205028 A1 | 12/2016 |
| WO | WO2017/015273 A1 | 1/2017 |
| WO | WO2017180453 A1 | 10/2017 |

OTHER PUBLICATIONS

Disclosed Anonymously, "Naw fragrance compositions and air care devices", IP.com No. IPCOM000240482D, Feb. 3, 2015.

* cited by examiner

FRESHENING COMPOSITIONS COMPRISING CONTROLLED RELEASE MODULATORS

CROSS REFERENCE TO RELATED APPLICATIONS

This application claims benefit of provisional patent application Ser. No. 62/712,701, filed Jul. 31, 2018, and entitled "FRESHENING COMPOSITIONS COMPRISING CONTROLLED RELEASE MODULATORS," the disclosure of which is incorporated herein in its entirety by reference for all purposes.

FIELD OF THE INVENTION

This invention relates to freshening compositions, preferably liquid freshening compositions, more preferably liquid air freshening compositions. Freshening compositions of the present invention may comprise one or more of a perfume raw material, a solvent and a fragrance release modulator. The invention also relates to air care products and devices comprising a freshening composition. Further, the invention relates to methods for formulating a freshening composition, methods for manufacturing an air care product or device comprising a freshening composition, methods for using a freshening composition to freshen the atmosphere, the air, or a surface, and methods for modulating evaporation of a freshening composition.

BACKGROUND OF THE INVENTION

Air care products, such as wicking-based, diffusion-based, spraying-based, or steam-based products have been commonly used to deliver various freshening compositions into the air or onto a surface. Exemplary freshening compositions used with such air care products may include volatile materials such as perfume compositions, perfume compositions in conjunction with malodor counteracting compositions, perfume compositions in conjunction with insect repelling compositions, or perfume compositions in conjunction with antimicrobial compositions.

When an air care product is based on a wicking releasing mechanism it mainly consists of (i) a liquid freshening composition, (ii) a container, (iii) a delivery element, which can be a wick or a plurality of wicks, a reed or a plurality of reeds, a stick or a plurality of sticks, a fiber or a plurality of fibers, a mesh, a porous or semi-porous substrate, and, optionally, (iv) an evaporation assisting device, such as in-wall electrical plug-in device, a heating device, or a fan. Commonly known air care products based on a wicking releasing mechanism include reed diffusers, wall electrical plug-ins and diffusers associated with a fan or heating system.

Diffusion-based air care products mainly consist of (i) a liquid freshening composition, (ii) a container, (iii) a diffusing interface, for example a membrane, and, optionally, (iv) a heating device, and (v) an air circulating device, such as a fan, or a combination thereof.

Spraying-based air care products mainly consist of (i) a container for accepting and storing an air freshening composition, which may contain a perfume composition or a perfume composition in conjunction with an active composition, such as a malodor counteracting composition, (iii) a propellant as a compressed gas, and (iv) a dispenser.

Steam-based air care products mainly consist of (i) a liquid freshening composition, (ii) a container, and (iii) a steam forming and releasing device.

Wicking, also known as wicking process, refers to a spontaneous transport of a liquid through a porous medium as a result of capillary suction taking place at liquid-gas interfaces at the surface or within the porous medium. Several wick-based systems designed to release perfumes or insect repellent liquids through a combined action of wicking process and evaporation are known. The performance a customer expects for an air care freshener based on a wicking process may include (i) an immediate hedonic experience, i.e., a strong perceived impression with respect to strength and character of the fragrance, also known in the art as "fragrance burst" or "fragrance blooming," and simply referred to as, smell, and (ii) a long-lasting hedonic experience, i.e., a long-lasting fragrance strength and character during the lifespan of the air care freshener product. To meet such customer's expectation, there is an imperative and unresolved need to provide and optimize a liquid freshening composition taking into consideration the design, geometrical characteristics, and physical parameters of a device delivering such air freshening composition. Further, the design of an evaporative assistance device, if such an element is involved, needs to be taken in consideration. In other words, a preferred air care product, such as an air care freshener would comprise a releasing profile of the liquid freshening composition that follows a two stage releasing regime: (i) an initial transitory regime, which is associated with an unusually high amount of liquid freshening composition release, and (ii) a steady-state release regime, which would require a linear release of the air care freshening composition into the external environment until, or very close to its full completion. Such an air care freshener product would operate until its entire liquid freshening composition is released into the external environment with no further human intervention. For example, in a reed diffuser, there should be no need to flip the reeds to achieve the above-mentioned hedonic experiences.

Most of the wicking air care fresheners on the current market fail to provide such a release performance. This failure can be attributed mainly due to (i) the lack of an initial transitory regime, which is responsible for the initial fragrance burst, which translates into a fragrance hedonic experience, (ii) the linear release of a freshening composition until its full completion, which is responsible for delivering the need fragrance experience, strength and character, and sometimes (iii) the high amount of residual product left in a reservoir that is not released. Therefore, there is a need in the art to provide an air care freshener satisfying the above-mentioned requirements.

Despite the critical role of the wicking process with respect to the release of the liquid freshening composition, most of the prior art air care products solely address the volatility of the freshening composition with respect to the fragrance delivery performance of an air freshening compositions, which is expressed based on the vapor pressure of the air freshening composition. Hence, it is of no surprise why known air care products are more concerned with (i) the rate of evaporation of a specific freshening composition, e.g., by taking into account the volatility of the fragrance ingredients, and that of solvents and diluents, and (ii) the design of a particular air care freshener device that may enhance the rate of evaporation of an air care freshening composition, such as an electrical external heater or fan.

Wicking air care fresheners known in the art most commonly use as a solvent or diluent glycol ethers and isoparaffines whose vapor pressures are below 0.1 mm Hg. While complying with the requirements imposed by the Environmental Protection Agency (EPA) and The California Air Resources Board (CARB) with respect to atmospheric emission of organic compounds, and more particularly with the restrictions on the emission level of the so-called "volatile organic compounds" (VOC), and displaying good performance to dissolve fragrance ingredients and having acceptable volatility, glycol ethers can impart specific undesired off-notes, which negatively affect the hedonic performance of an air care freshener product. Further, based on the recent ingredient disclosure initiatives (a new norm accepted and embraced by the consumer goods industry to disclose to the customers the names of the ingredients into their products including the fragrance ingredients), glycol ethers are chemicals that become less and less desired, if not undesired, by customers.

Some silicon solvents, which are exempted by the EPA and CARB and not considered being VOC, can also be used in the formulation of a wicking air freshener diffuser. However, due to their fragrance solubility issues and high cost, the use of silicon solvents in air care freshener products is restricted.

The volatility of a freshening composition varies based on the particular compounds of the composition. As the vapor pressure of a freshening composition increases, the rate at which the freshening composition volatilizes, i.e., evaporates, also increases. As a result, the lifespan of an air care product comprising such freshening composition can be dependent upon the particular freshening composition used. In some cases, carriers, such as solvents and diluents are used to slow down the rate of evaporation of a freshening composition. However, adding carriers to slow down the evaporation rate of a freshening composition may significantly reduce the level of perfume materials in the freshening composition or may even change the character of the freshening composition and its scent characteristics.

There is an unfulfilled need for a freshening composition that delivers long-lasting scent. The present invention provides such freshening compositions, air care products and devices comprising same and methods for manufacturing and using same.

Further, there is an unfulfilled need for a method to manufacture and to provide an air care freshening wicking product that (i) releases an air freshening composition over a specific period of time without human intervention so that no or very minimal residual amounts of that composition will remain in a reservoir and (ii) provides for a two-stage product releasing regime wherein an initial transitory regime is associated with a high amount of liquid freshening composition release, and wherein a steady-state release regime provides for the linear release of the air care freshening composition into the external environment until, or very close to its full completion. The present invention provides such liquid freshening compositions, air care products and devices comprising same and methods for manufacturing and using same.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this specification.

BRIEF SUMMARY OF THE INVENTION

The present invention provides a variety of freshening compositions, a variety of air freshener devices comprising a freshening composition as well as a variety of methods for manufacturing a freshening composition and a variety of methods for manufacturing an air freshener device comprising a freshening composition.

In some embodiments of the present invention, a freshening composition comprises from about 0.1 wt % to about 95 wt % perfume raw material. In some embodiments of the present invention, a freshening composition comprises (i) from about 0.1 wt % to about 95 wt % perfume raw material and (ii) from about 1.0 wt % to about 95 wt % of a non-glycol ether solvent, a non-glycol ether diluent, or a mixture thereof. In some embodiments of the present invention, a freshening composition comprises from about 0.1 wt % to about 95 wt % perfume raw material and (ii) from about 0.01 wt % to about 90 wt % fragrance release modulator. In some embodiments of the present invention, a freshening composition comprises (i) from about 0.1 wt % to about 95 wt % perfume raw material, (ii) from about 1.0 wt % to about 95 wt % of a non-glycol ether solvent, a non-glycol ether diluent, or a mixture thereof, and (iii) from about 0.01 wt % to about 90 wt % fragrance release modulator.

Various perfume raw materials may be used in a freshening composition, in an air freshener device comprising a freshening composition and in a method for manufacturing a freshening composition or in a method for manufacturing an air freshener device comprising a freshening composition. In some embodiments of the present invention, a perfume raw material is selected from the group consisting of an ester, an alcohol, an aldehyde, a ketone, an acetal, a phenol, an ether, a lactone, a furan, a hydrocarbon, an acid, a natural origin fragrance compound, a stereoisomer of any preceeding perfume raw material, and a mixture of any of the preceeding perfume raw materials.

A variety of freshening composition and methods for manufacturing a freshening composition are contemplated and disclosed herein. In some embodiments of the present invention, a freshening composition has one or more characteristics selected from the group consisting of a flash point of greater than about 100° F., a surface tension of less than about 60 mN/m, a dynamic viscosity from about 0.5 cp to about 100 cp, and a density from about 600 g/l to about 1,300 g/l. Surface tension values can be expressed either as mN/m or as dyne/cm. Dynamic viscosity can be expressed either as cp or as mPa-s.

Various fragrance release modulators may be used in a freshening composition, in an air freshener device comprising a freshening composition and in a method for manufacturing a freshening composition or in a method for manufacturing an air freshener device comprising a freshening composition. In some embodiments of the present invention, a fragrance release modulator is selected from the group consisting of a $C_{2-8}$ linear alcohol, a $C_{2-8}$ branched alcohol, an alkyl-ether, an aryl-ether, an alkyl-glycol, an aryl-glycol, an alkyl-carbonate, an aryl-carbonate, an alkyldiol, an alkyl-adipate, an aryl-adipate, an alkyl-benzoate, an aryl-benzoate, an alkyl-citrate, an aryl-citrate, an alkyl-laurate, an aryl-laurate, an alkyl-palmitate, an aryl-palmitate, an alkyl-stearate, an aryl-stearate, an aryl-myristate, an alkyl-succinate, an aryl-succinate, an alkyl-glutarate, an aryl-glutarate, a silicon solvent, and a mixture of any of the preceeding fragrance release modulators.

In some embodiments of the present invention, a freshening composition is adapted to have one or more of a characteristic selected from the group consisting of a flash point higher than about 100° F., a surface tension of about 10 mN/m to about 40 mN/m, a dynamic viscosity from about 1 cp to about 30 cp, and a density from about 650 g/l to about 1,300 g/l.

In some embodiments of the present invention, a freshening composition comprises (i) from about 0.1 wt % to about 95 wt % perfume raw material comprising one or more ingredients selected from the group consisting of an ester, an alcohol, an aldehyde, a ketone, an acetal, a phenol, an ether, a lactone, a furan, a hydrocarbon, an acid, a natural origin fragrance compound, a stereoisomer of any preceeding perfume raw material, and a mixture of any of the preceeding perfume raw materials, (ii) from about 1.0 wt % to about 95 wt % of a non-glycol ether solvent, a non-glycol ether diluent, or a mixture thereof, and (iii) from about 0.01 wt % to about 90 wt % fragrance release modulator having one or more characteristics selected from the group consisting of (a) a flash point higher than about 100° F., (b) a surface tension of less than about 60 mN/m, (c) a dynamic viscosity from about 0.5 cp to about 100 cp, and (d) a density from about 600 g/l to about 1,300 g/l and wherein the fragrance release modulator is selected from the group consisting of a $C_{2-8}$ linear alcohol, a $C_{2-8}$ branched alcohol, an alkyl-ether, an aryl-ether, an alkyl-glycol, an aryl-glycol, an alkyl-carbonate, an aryl-carbonate, an alkyldiol, an alkyl-adipate, an aryl-adipate, an alkyl-benzoate, an aryl-benzoate, an alkyl-citrate, an aryl-citrate, an alkyl-laurate, an aryl-laurate, an alkyl-palmitate, an aryl-palmitate, an alkyl-stearate, an aryl-stearate, an aryl-myristate, an alkyl-succinate, an aryl-succinate, an alkyl-glutarate, an aryl-glutarate, a silicon solvent, a stereoisomer of any preceeding fragrance release modulator, and a mixture of any of the preceeding fragrance release modulators. In some embodiments, a freshening composition comprising (i), (ii), and (iii) as listed in this paragraph is adapted to have one or more of a characteristic selected from the group consisting of (a) a flash point higher than about 100° F., (b) a surface tension from about 10 mN/m to about 40 mN/m, (c) a dynamic viscosity from about 1 cp to about 30 cp, and (d) a density from about 650 g/l to about 1,300 g/l.

In some embodiments of a freshening composition, of an air freshener device comprising a freshening composition and of a method for manufacturing a freshening composition or of a method for manufacturing an air freshener device comprising a freshening composition, a perfume raw material comprises a plurality of perfume raw materials.

In some embodiments of a freshening composition, of an air freshener device comprising a freshening composition and of a method for manufacturing a freshening composition or of a method for manufacturing an air freshener device comprising a freshening composition, a non-glycol ether solvent is selected from the group consisting of an alkyladipate, an aryladipate, an alkyl-glycerol, an aryl-glycerol, an alkyldiol, and aryldiol, an isoparaffine, a silicon, and a mixture of any of the preceeding non-glycol ether solvents.

In some embodiments of a freshening composition, of an air freshener device comprising a freshening composition and of a method for manufacturing a freshening composition or of a method for manufacturing an air freshener device comprising a freshening composition, a non-glycol ether solvent is selected from the group consisting of 2,2-dimethyl-1,3-dioxolane-4-methanol, 3-methyl-1,3-butanediol-1-acetate, dimethyl adipate, dimethicone, disiloxane, trisiloxane, a $C_{15-19}$alkane, a $C_{13-19}$isoparaffine, a cyclosiloxane, Isopar™ M Fluid, an alkylcyclosiloxane, an aryl-cyclosiloxane, and any combination of any of the preceeding non-glycol ether solvents. Isopar™ M Fluid is produced from petroleum-based raw materials, which are treated with hydrogen in the presence of a catalyst to produce a low odor, low aromatic hydrogencarbon solvent. The major components include normal alkanes, isoalkanes, and cycloalkanes. (See, Exxon Mobile Isopar™ M Fluid, Product Safety Summary). For EU only: EC No.: 920-901-0 and 927-676-8; Chemical Name: Hydrocarbons, $C_{11}$-$C_{16}$, isoalkanes, <2% aromatics. CAS No. 64742-8; Chemical Name: Distillates (petroleum), Hydrotreated light.

In some embodiments of a freshening composition, of an air freshener device comprising a freshening composition and of a method for manufacturing a freshening composition or of a method for manufacturing an air freshener device comprising a freshening composition, a fragrance release modulator is selected from the group consisting of ethanol, n-propanol, iso-propanol, n-butanol, t-butanol, 3-methoxy-3-methyl-1-butanol, 1-pentanol, 2-pentanol, amyl-alcohol, n-pentyl alcohol, 1,3 propanediol, 1,2 hexanediol, 1,2 pentanediol, dimethyl ether, propylene glycol, dipropylene glycol, hexyleneglycol, glycerol, benzyl benzoate, triethylcitrate, dioctyl adipate, propylene carbonate, dimethyl carbonate, isoamyl laurate, methyl palmitate, methyl stearate, dimethyl ether, dimethyl adipate, dimethyl succinate, dimethyl glutarate, n-butyl propionate, dimethicone, disiloxane, trisiloxane, and a mixture of any of the preceeding fragrance release modulators.

In addition to (i) a perfume raw material, (ii) a non-glycol ether solvent, a non-glycol ether diluent or a mixture thereof, and (iii) a fragrance modulator, a freshening composition of the present invention may comprise one or more additional ingredients. In some embodiments of a freshening composition, of an air freshener device comprising a freshening composition and of a method for manufacturing a freshening composition or of a method for manufacturing an air freshener device comprising a freshening composition, a freshening composition further comprises less than about 50 wt % of an ingredient having a functional activity. In some embodiments, the ingredient having a functional activity is selected from the group consisting of an ingredient having malodor counteracting activity, an ingredient having antimicrobial activity, an ingredient having an insect repellant activity, an ingredient having a preservative activity, an ingredient having an antioxidant activity, an ingredient having a humectant activity, an ingredient having a UV-blocking activity, an ingredient having a pigment activity, an ingredient having a dye activity, an ingredient having a surfactant activity, an ingredient having an emulsifier activity, an ingredient having a solubilizer activity, an ingredient having a polymer activity, and an ingredient having a buffer activity.

In some embodiments of a freshening composition, of an air freshener device comprising a freshening composition and of a method for manufacturing a freshening composition or of a method for manufacturing an air freshener device comprising a freshening composition, a freshening composition further comprises less than about 50 wt % of an ingredient having a functional activity. In some embodiments of the present invention, the ingredient having the functional activity is selected from the group consisting of an ingredient having malodor counteracting activity, an ingredient having antimicrobial activity, an insect repellant, a preservative, an antioxidant, a humectant, a UV-blocking agent, a pigment, a dye, a surfactant, an emulsifier, a solubilizer, a polymer, and a buffer.

In some embodiments of the present invention, the freshening composition comprises an ingredient having a functional activity in an amount of less than about 50 wt %, in an amount of less than about 40 wt %, in an amount of less than about 30 wt %, in an amount of less than about 20%, in an amount of less than about 10 wt %, or in an amount of less than about 5 wt %.

It is understood and one of ordinary skill in the art will appreciate that, if not clearly contradicted by the content of this specification, each embodiment of a freshening composition and/or features/elements disclosed as part of that embodiment can be combined with any of the embodiments hereinabove or hereinbelow.

The present invention provides a variety of air freshener devices comprising a freshening composition. In some embodiments of the present invention, an air freshener device comprises a freshening composition as described herein. An exemplary non-limiting air freshener device of the present invention comprises a freshening composition comprising (i) from about 0.1 wt % to about 95 wt % perfume raw material comprising one or more ingredients selected from the group consisting of an ester, an alcohol, an aldehyde, a ketone, an acetal, a phenol, an ether, a lactone, a furan, a hydrocarbon, an acid, a natural origin fragrance compound, a stereoisomer of any preceeding perfume raw material, and a mixture of any of the preceeding perfume raw materials; (ii) from about 1.0 wt % to about 95 wt % of a non-glycol ether solvent, a non-glycol ether diluent, or a mixture thereof; and (iii) from about 0.01 wt % to about 90 wt % fragrance release modulator having one or more characteristics selected from the group consisting of (a) a flash point higher than about 100° F., (b) a surface tension of less than about 60 mN/m, (c) a dynamic viscosity from about 0.5 cp to about 100 cp, and (d) a density from about 600 g/l to about 1,300 g/l and wherein the fragrance release modulator is selected from the group consisting of a $C_{2-8}$ linear alcohol, a $C_{2-8}$ branched alcohol, an alkyl-ether, an aryl-ether, an alkyl-glycol, an aryl-glycol, an alkyl-carbonate, an aryl-carbonate, an alkyldiol, an alkyl-adipate, an aryl-adipate, an alkyl-benzoate, an aryl-benzoate, an alkyl-citrate, an aryl-citrate, an alkyl-laurate, an aryl-laurate, an alkyl-palmitate, an aryl-palmitate, an alkyl-stearate, an aryl-stearate, an aryl-myristate, an alkyl-succinate, an aryl-succinate, an alkyl-glutarate, an aryl-glutarate, a silicon solvent, a stereoisomer of any preceding fragrance release modulator, and a mixture of any of the preceeding fragrance release modulators. In some embodiments of an air freshener device or of a method for manufacturing an air freshener device comprising an air freshening composition, the freshening composition comprises (i), (ii), and (iii) as listed in this paragraph and is adapted to have one or more of a characteristic selected from the group consisting of (a) a flash point higher than about 100° F., (b) a surface tension from about 10 mN/m to about 40 mN/m, (c) a dynamic viscosity from about 1 cp to about 30 cp, and (d) a density from about 650 g/l to about 1,300 g/l.

In some embodiments of an air freshener device comprising a freshening composition and in a method for manufacturing an air freshener device comprising a freshening composition, the air freshener comprises a freshening composition comprising (i) less than about 90 wt % fragrance release modulator, (ii) greater than about 5 wt % perfume raw materials, and (iii) between about 10 wt % to about 90 wt % non-glycol ether solvent.

In some embodiments of an air freshener device comprising a freshening composition and in a method for manufacturing an air freshener device comprising a freshening composition, the air freshener comprises a freshening composition comprising an ingredient having a functional activity in an amount of less than about 50 wt %, in an amount of less than about 40 wt %, in an amount of less than about 30 wt %, in an amount of less than about 20%, in an amount of less than about 10 wt %, or in an amount of less than about 5 wt %. In some embodiments, the ingredient having a functional activity is selected from the group consisting of an ingredient having malodor counteracting activity, an ingredient having antimicrobial activity, an ingredient having an insect repellant activity, an ingredient having a preservative activity, an ingredient having an antioxidant activity, an ingredient having a humectant activity, an ingredient having a UV-blocking activity, an ingredient having a pigment activity, an ingredient having a dye activity, an ingredient having a surfactant activity, an ingredient having an emulsifier activity, an ingredient having a solubilizer activity, an ingredient having a polymer activity, and an ingredient having a buffer activity. In some embodiments of the present invention, the ingredient having the functional activity is selected from the group consisting of an ingredient having malodor counteracting activity, an ingredient having antimicrobial activity, an insect repellant, a preservative, an antioxidant, a humectant, a UV-blocking agent, a pigment, a dye, a surfactant, an emulsifier, a solubilizer, a polymer, and a buffer.

In some embodiments of an air freshener device comprising a freshening composition and in a method for manufacturing an air freshener device comprising a freshening composition, the air freshener device comprises a freshening composition and one or more additional components. A variety of additional components may be used.

In some embodiments of an air freshener device comprising a freshening composition and in a method for manufacturing an air freshener device comprising a freshening composition, the air freshener device further comprises a delivery system comprising an element in communication or in contact with the freshening composition. A variety of delivery systems may be used. In some embodiments of an air freshener device comprising a freshening composition and in a method for manufacturing an air freshener device comprising a freshening composition, the air freshener device comprises a delivery system selected from the group consisting of a reed, a plurality of reeds, a stick, a plurality of sticks, a fiber, a plurality of fibers, a wick, a plurality of wicks, a mesh material, a conductive mesh material, a porous substrate, a semi-porous substrate, and a combination of any of the preceeding delivery systems.

In some embodiments of an air freshener device comprising a freshening composition and in a method for manufacturing an air freshener device comprising a freshening composition, the air freshener device further comprises a reservoir having a functionality selected from the group consisting of accepting a freshening composition, receiving a freshening composition, holding a freshening composition, housing freshening composition and storing a freshening composition. A variety of reservoirs may be used. In some embodiments of an air freshener device comprising a freshening composition and in a method for manufacturing an air freshener device comprising a freshening composition, the air freshener device comprises a reservoir selected from the group consisting of a bottle, a vessel, and a container.

In some embodiments of an air freshener device comprising a freshening composition and in a method for manufacturing an air freshener device comprising a freshening composition, the air freshener device further comprises an evaporative assistance element. A variety of evaporative assistance elements may be used. In some embodiments of an air freshener device comprising a freshening composition and in a method for manufacturing an air freshener device comprising a freshening composition, the air freshener device comprises an evaporative assistance element selected from the group consisting of a heater, a fan, an agitator, and a combination of any preceeding evaporative assistance elements.

In some embodiments of an air freshener device comprising a freshening composition and in a method for manufacturing an air freshener device comprising a freshening composition, the air freshener device further comprises a delivery system and an evaporative assistance element. A variety of delivery systems and evaporative assistance elements may be used. In some embodiments of an air freshener device comprising a freshening composition and in a method for manufacturing an air freshener device comprising a freshening composition, the air freshener device comprises a heater wherein the heater is configured to heat a delivery system to a temperature in the range from about 45° C. to about 75° C.

It is understood and one of ordinary skill in the art will appreciate that, if not clearly contradicted by the content of this specification, each embodiment of an air freshener device comprising a freshening composition and/or features/elements disclosed as part of that embodiment can be combined with any of the embodiments hereinabove or hereinbelow.

The present invention provides a variety of methods for manufacturing a freshening composition. In some embodiments of a method for manufacturing a freshening composition, the method comprises the step of combining (i) from about 0.1 wt % to about 95 wt % perfume raw material, and (ii) from about 1.0 wt % to about 95 wt % of a non-glycol ether solvent, a non-glycol ether diluent, or a mixture thereof. In some embodiments of the present invention, a method for manufacturing a freshening composition comprises the step of combining (i) from about 0.1 wt % to about 95 wt % perfume raw material and (ii) from about 0.01 wt % to about 90 wt % fragrance release modulator. In some embodiments of the present invention, a method for manufacturing a freshening composition comprises the step of combining (i) from about 0.1 wt % to about 95 wt % perfume raw material, (ii) from about 1.0 wt % to about 95 wt % of a non-glycol ether solvent, a non-glycol ether diluent, or a mixture thereof, and (iii) from about 0.01 wt % to about 90 wt % fragrance release modulator. In some embodiments of the present invention, a method for manufacturing a freshening composition comprises the step of combining (i) from about 0.1 wt % to about 95 wt % perfume raw material, (ii) from about 1.0 wt % to about 95 wt % of a non-glycol ether solvent, a non-glycol ether diluent, or a mixture thereof, (iii) from about 0.01 wt % to about 90 wt % fragrance release modulator, and (iv) less than about 50 wt % of an ingredient having a functional activity. Ingredients (i), (ii), (iii), and (iv) may be any as described herein.

An exemplary and non-limiting method for manufacturing a freshening composition, comprises the step of combining (i) from about 0.1 wt % to about 95 wt % perfume raw material comprising one or more ingredients selected from the group consisting of an ester, an alcohol, an aldehyde, a ketone, an acetal, a phenol, an ether, a lactone, a furan, a hydrocarbon, an acid, a natural origin fragrance compound, a stereoisomer of any preceeding perfume raw material, and a mixture of any of the preceeding perfume raw materials, (ii) from about 1.0 wt % to about 95 wt % of a non-glycol ether solvent, a non-glycol ether diluent, or a mixture thereof, and (iii) from about 0.01 wt % to about 90 wt % fragrance release modulator having one or more characteristics selected from the group consisting of (a) a flash point higher than about 100° F., (b) a surface tension of less than about 60 mN/m, (c) a dynamic viscosity from about 0.5 cp to about 100 cp, and (d) a density from about 600 g/l to about 1,300 g/l and wherein the fragrance release modulator is selected from the group consisting of a $C_{2-8}$ linear alcohol, a $C_{2-8}$ branched alcohol, an alkyl-ether, an aryl-ether, an alkyl-glycol, an aryl-glycol, an alkyl-carbonate, an aryl-carbonate, an alkyldiol, an alkyl-adipate, an aryl-adipate, an alkyl-benzoate, an aryl-benzoate, an alkyl-citrate, an aryl-citrate, an alkyl-laurate, an aryl-laurate, an alkyl-palmitate, an aryl-palmitate, an alkyl-stearate, an aryl-stearate, an aryl-myristate, an alkyl-succinate, an aryl-succinate, an alkyl-glutarate, an aryl-glutarate, a silicon solvent, a stereoisomer of any preceeding fragrance release modulator, and a mixture of any of the preceeding fragrance release modulators. In some embodiments of method for manufacturing a freshening composition, the method comprises the steps of combining (i), (ii), and (iii) as listed in this paragraph and adapting the freshening composition to have one or more of a characteristic selected from the group consisting of (a) a flash point higher than about 100° F., (b) a surface tension from about 10 mN/m to about 40 mN/m, (c) a dynamic viscosity from about 1 cp to about 30 cp, and (d) a density from about 650 g/l to about 1,300 g/l.

It is understood and one of ordinary skill in the art will appreciate that, if not clearly contradicted by the content of this specification, each embodiment of a method for manufacturing a freshening composition and/or features/elements disclosed as part of that embodiment can be combined with any of the embodiments hereinabove or hereinbelow.

The present invention provides a variety of methods for manufacturing an air freshener device comprising a freshening composition. In some embodiments of a method for manufacturing an air freshener device comprising a freshening composition, the method comprises the step of contacting a reservoir in an air freshening device with a freshening composition.

In some embodiments of a method for manufacturing an air freshener device comprising a freshening composition, the method comprises the step of contacting a reservoir in an air freshening device with a freshening composition comprising (i) from about 0.1 wt % to about 95 wt % perfume raw material, and (ii) from about 1.0 wt % to about 95 wt % of a non-glycol ether solvent, a non-glycol ether diluent, or a mixture thereof. In some embodiments of a method for manufacturing an air freshener device comprising a freshening composition, the method comprises the step of contacting a reservoir in an air freshening device with a freshening composition comprising (i) from about 0.1 wt % to about 95 wt % perfume raw material and (ii) from about 0.01 wt % to about 90 wt % fragrance release modulator. In some embodiments of a method for manufacturing an air freshener device comprising a freshening composition, the method comprises the step of contacting a reservoir in an air freshening device with a freshening composition comprising (i) from about 0.1 wt % to about 95 wt % perfume raw material, (ii) from about 1.0 wt % to about 95 wt % of a non-glycol ether solvent, a non-glycol ether diluent, or a mixture thereof, and (iii) from about 0.01 wt % to about 90 wt % fragrance release modulator. In some embodiments of a method for manufacturing an air freshener device comprising a freshening composition, the method comprises the step of contacting a reservoir in an air freshening device with a freshening composition comprising (i) from about 0.1 wt % to about 95 wt % perfume raw material, (ii) from about 1.0 wt % to about 95 wt % of a non-glycol ether solvent, a non-glycol ether diluent, or a mixture thereof, (iii) from about 0.01 wt % to about 90 wt % fragrance release modulator, and (iv) less than about 50 wt % of an ingredient having a functional activity. Ingredients (i), (ii), (iii), and (iv) may be any as described herein.

An exemplary and non-limiting method for manufacturing an air freshener device comprising a freshening composition, comprises the step of contacting a reservoir in an air freshening device with a freshening composition comprising (i) from about 0.1 wt % to about 95 wt % perfume raw material comprising one or more ingredients selected from the group consisting of an ester, an alcohol, an aldehyde, a ketone, an acetal, a phenol, an ether, a lactone, a furan, a hydrocarbon, an acid, a natural origin fragrance compound, a stereoisomer of any preceeding perfume raw material, and a mixture of any of the preceeding perfume raw materials, (ii) from about 1.0 wt % to about 95 wt % of a non-glycol ether solvent, a non-glycol ether diluent, or a mixture thereof, and (iii) from about 0.01 wt % to about 90 wt % fragrance release modulator having one or more characteristics selected from the group consisting of (a) a flash point higher than about 100° F., (b) a surface tension of less than about 60 mN/m, (c) a dynamic viscosity from about 0.5 cp to about 100 cp, and (d) a density from about 600 g/l to about 1,300 g/l and wherein the fragrance release modulator is selected from the group consisting of a $C_{2-8}$ linear alcohol, a $C_{2-8}$ branched alcohol, an alkyl-ether, an aryl-ether, an alkyl-glycol, an aryl-glycol, an alkyl-carbonate, an aryl-carbonate, an alkyldiol, an alkyl-adipate, an aryl-adipate, an alkyl-benzoate, an aryl-benzoate, an alkyl-citrate, an aryl-citrate, an alkyl-laurate, an aryl-laurate, an alkyl-palmitate, an aryl-palmitate, an alkyl-stearate, an aryl-stearate, an aryl-myristate, an alkyl-succinate, an aryl-succinate, an alkyl-glutarate, an aryl-glutarate, a silicon solvent, a stereoisomer of any preceeding fragrance release modulator, and a mixture of any of the preceeding fragrance release modulators. In some embodiments of method for manufacturing an air freshener device comprising a freshening composition, the method comprises the steps of (A) contacting a reservoir in an air freshening device with a freshening composition comprising (i), (ii), and (iii) as listed in this paragraph and (B) adapting the freshening composition to have one or more of a characteristic selected from the group consisting of (a) a flash point higher than about 100° F., (b) a surface tension from about 10 mN/m to about 40 mN/m, (c) a dynamic viscosity from about 1 cp to about 30 cp, and (d) a density from about 650 g/l to about 1,300 g/l. In some embodiments of method for manufacturing an air freshener device comprising a freshening composition, the method comprises the steps of (A) contacting a reservoir in an air freshening device with a freshening composition comprising (i), (ii), and (iii) as listed in this paragraph, (B) adapting the freshening composition to have one or more of a characteristic selected from the group consisting of (a) a flash point higher than about 100° F., (b) a surface tension from about 10 mN/m to about 40 mN/m, (c) a dynamic viscosity from about 1 cp to about 30 cp, and (d) a density from about 650 g/l to about 1,300 g/l, and (C) configuring the air freshener device to provide a controllable or customizable rate of release of the freshening composition.

It is understood and one of ordinary skill in the art will appreciate that, if not clearly contradicted by the content of this specification, each embodiment of a method for manufacturing an air freshener device comprising a freshening composition and/or features/elements disclosed as part of that embodiment can be combined with any of the embodiments hereinabove or hereinbelow.

Some embodiments of a freshening composition of the present invention are set forth below:

Embodiment 1. A freshening composition comprising:
(i) from about 0.1 wt % to about 95 wt % perfume raw material, the perfume raw material comprising one or more ingredients selected from the group consisting of an ester, an alcohol, an aldehyde, a ketone, an acetal, a phenol, an ether, a lactone, a furan, a hydrocarbon, an acid, a natural origin fragrance compound, a stereoisomer of any preceeding perfume raw material, and a mixture of any of the preceeding perfume raw materials;
(ii) from about 1.0 wt % to about 95 wt % of a non-glycol ether solvent, a non-glycol ether diluent, or a mixture thereof; and
(iii) from about 0.01 wt % to about 90 wt % fragrance release modulator having one or more characteristics selected from the group consisting of:
(a) a flash point higher than about 100° F.,
(b) a surface tension of less than about 60 mN/m,
(c) a dynamic viscosity from about 0.5 cp to about 100 cp, and
(d) a density from about 600 g/l to about 1,300 g/l;
wherein the fragrance release modulator is selected from the group consisting of a $C_{2-8}$ linear alcohol, a $C_{2-8}$ branched alcohol, an alkyl-ether, an aryl-ether, an alkyl-glycol, an aryl-glycol, an alkyl-carbonate, an aryl-carbonate, an alkyldiol, an alkyl-adipate, an aryl-adipate, an alkyl-benzoate, an aryl-benzoate, an alkyl-citrate, an aryl-citrate, an alkyl-laurate, an aryl-laurate, an alkyl-palmitate, an aryl-palmitate, an alkyl-stearate, an aryl-stearate, an aryl-myristate, an alkyl-succinate, an aryl-succinate, an alkyl-glutarate, an aryl-glutarate, a silicon solvent, a stereoisomer of any preceeding fragrance release modulator, and a mixture of any of the preceeding fragrance release modulators; and
wherein the freshening composition is adapted to have one or more of a characteristic selected from the group consisting of:
(a) a flash point higher than about 100° F.,
(b) a surface tension from about 10 mN/m to about 40 mN/m,
(c) a dynamic viscosity from about 1 cp to about 30 cp, and
(d) a density from about 650 g/l to about 1,300 g/l.

Embodiment 2. The freshening composition of Embodiment 1, wherein the perfume raw material comprises a plurality of perfume raw materials.

Embodiment 3. The freshening composition according to any one of Embodiments 1-2, wherein the non-glycol ether solvent is selected from the group consisting of an alkyladipate, an aryladipate, an alkyl-glycerol, an aryl-glycerol, an alkyldiol, and aryldiol, an isoparaffine, a silicon, and a mixture of any of the preceeding non-glycol ether solvents.

Embodiment 4. The freshening composition according to any one of Embodiments 1-2, wherein the non-glycol ether solvent is selected from the group consisting of 2,2-dimethyl-1,3-dioxolane-4-methanol, 3-methyl-1,3-butanediol-1-acetate, dimethyl adipate, dimethicone, disiloxane, trisiloxane, a $C_{15-19}$alkane, a $C_{13-19}$isoparaffine, a cyclosiloxane, Isopar M®, an alkylcyclosiloxane, an aryl-cyclosiloxane, and a combination of any of the preceeding non-glycol ether solvents.

Embodiment 5. The freshening composition according to any one of Embodiments 1-4, wherein the fragrance release modulator is selected from the group consisting of ethanol, n-propanol, iso-propanol, n-butanol, t-butanol, 3-methoxy-3-methyl-1-butanol, 1-pentanol, 2-pentanol, amyl-alcohol, n-pentyl alcohol, 1,3 propanediol, 1,2 hexanediol, 1,2 pentanediol, dimethyl ether, propylene glycol, dipropylene glycol, hexyleneglycol, glycerol, benzyl benzoate, triethylcitrate, dioctyl adipate, propylene carbonate, dimethyl carbonate, isoamyl laurate, methyl palmitate, methyl stearate, dimethyl ether, dimethyl adipate, dimethyl succinate, dimethyl glutarate, n-butyl propionate, dimethicone, disiloxane, trisiloxane, and a mixture of any of the preceeding fragrance release modulators.

Embodiment 6. The freshening composition according to any one of Embodiments 1-5, further comprising less than about 50 wt % of an ingredient having a functional activity and wherein the ingredient having the functional activity is selected from the group consisting of an ingredient having malodor counteracting activity, an ingredient having antimicrobial activity, an insect repellant, a preservative, an antioxidant, a humectant, a UV-blocking agent, a pigment, a dye, a surfactant, an emulsifier, a solubilizer, a polymer, and a buffer.

It is understood and one of ordinary skill in the art will appreciate that, if not clearly contradicted by the content of this specification, each embodiment of a freshening composition and/or features/elements disclosed as part of that embodiment can be combined with any of the embodiments hereinabove or hereinbelow.

Some embodiments of an air freshener device comprising a freshening composition and of the present invention are set forth below:

Embodiment 1. An air freshener device comprising a freshening composition, wherein the freshening composition comprises:
  (i) from about 0.1 wt % to about 95 wt % perfume raw material, the perfume raw material comprising one or more ingredients selected from the group consisting of an ester, an alcohol, an aldehyde, a ketone, an acetal, a phenol, an ether, a lactone, a furan, a hydrocarbon, an acid, a natural origin fragrance compound, a stereoisomer of any preceeding perfume raw material, and a mixture of any of the preceeding perfume raw materials;
  (ii) from about 1.0 wt % to about 95 wt % of a non-glycol ether solvent, a non-glycol ether diluent, or a mixture thereof; and
  (iii) from about 0.01 wt % to about 90 wt % fragrance release modulator having one or more characteristics selected from the group consisting of:
    (a) a flash point higher than about 100° F.,
    (b) a surface tension of less than about 60 mN/m,
    (c) a dynamic viscosity from about 0.5 cp to about 100 cp, and
    (d) a density from about 600 g/l to about 1,300 g/l;
      wherein the fragrance release modulator is selected from the group consisting of a $C_{2-8}$ linear alcohol, a $C_{2-8}$ branched alcohol, an alkyl-ether, an aryl-ether, an alkyl-glycol, an aryl-glycol, an alkyl-carbonate, an aryl-carbonate, an alkyldiol, an alkyl-adipate, an aryl-adipate, an alkyl-benzoate, an aryl-benzoate, an alkyl-citrate, an aryl-citrate, an alkyl-laurate, an aryl-laurate, an alkyl-palmitate, an aryl-palmitate, an alkyl-stearate, an aryl-stearate, an alkyl-myristate, an alkyl-succinate, an aryl-succinate, an alkyl-glutarate, an aryl-glutarate, a silicon solvent, a stereoisomer of any preceeding fragrance release modulator, and a mixture of any of the preceeding fragrance release modulators; and
  wherein the freshening composition is adapted to have one or more of a characteristic selected from the group consisting of:
    (a) a flash point higher than about 100° F.,
    (b) a surface tension from about 10 mN/m to about 40 mN/m,
    (c) a dynamic viscosity from about 1 cp to about 30 cp, and
    (d) a density from about 650 g/l to about 1,300 g/l;
  and wherein the air freshener device is configured to provide a controllable or customizable rate of release of the freshening composition.

Embodiment 2. The air freshener device according to Embodiment 1, comprising: (i) less than about 90 wt % fragrance release modulator, (ii) greater than about 5 wt % perfume raw materials; and (iii) from about 10 wt % to about 90 wt % non-glycol ether solvent.

Embodiment 3. The air freshener device according to any one of Embodiments 1-2, wherein the perfume raw material comprises a plurality of perfume raw materials.

Embodiment 4. The air freshener device according to any one of Embodiments 1-3, wherein the non-glycol ether solvent is selected from the group consisting of an alkyladipate, an aryladipate, an alkyl-glycerol, an aryl-glycerol, an alkyldiol, and aryldiol, an isoparaffine, a silicon, and a mixture of any of the preceeding non-glycol ether solvents.

Embodiment 5. The air freshener device according to any one of Embodiments 1-3, wherein the non-glycol ether solvent is selected from the group consisting of 2,2-dimethyl-1,3-dioxolane-4-methanol, 3-methyl-1,3-butanediol-1-acetate, dimethyl adipate, dimethicone, disiloxane, trisiloxane, a $C_{15-19}$alkane, a $C_{13-19}$isoparaffine, a cyclosiloxane, Isopar M®, an alkylcyclosiloxane, an aryl-cyclosiloxane, and a combination of any of the preceeding non-glycol ether solvents.

Embodiment 6. The air freshener device according to any one of Embodiments 1-5, wherein the fragrance release modulator is selected from the group consisting of ethanol, n-propanol, iso-propanol, n-butanol, t-butanol, 3-methoxy-3-methyl-1-butanol, 1-pentanol, 2-pentanol, amyl-alcohol, n-pentyl alcohol, 1,3 propanediol, 1,2 hexanediol, 1,2 pentanediol, dimethyl ether, propylene glycol, dipropylene glycol, hexyleneglycol, glycerol, benzyl benzoate, triethylcitrate, dioctyl adipate, propylene carbonate, dimethyl carbonate, isoamyl laurate, methyl palmitate, methyl stearate, dimethyl ether, dimethyl adipate, dimethyl succinate, dimethyl glutarate, n-butyl propionate, dimethicone, disiloxane, trisiloxane, and a mixture of any of the preceeding fragrance release modulators.

Embodiment 7. The air freshener device according to any one of Embodiments 1-6, further comprising less than about 50 wt % of an ingredient having a functional activity and wherein the ingredient having the functional activity is selected from the group consisting of an ingredient having malodor counteracting activity, an ingredient having antimicrobial activity, an ingredient having an insect repellant activity, an ingredient having a preservative activity, an ingredient having an antioxidant activity, an ingredient having a humectant activity, an ingredient having a UV-blocking activity, an ingredient having a pigment activity, an ingredient having a dye activity, an ingredient having a surfactant activity, an ingredient having an emulsifier activity, an ingredient having a solubilizer activity, an ingredient having a polymer activity, and an ingredient having a buffer activity.

Embodiment 8. The air freshener device according to any one of Embodiments 1-7, wherein the ingredient having the functional activity is selected from the group consisting of an ingredient having malodor counteracting activity, an ingredient having antimicrobial activity, an insect repellant, a preservative, an antioxidant, a humectant, a UV-blocking agent, a pigment, a dye, a surfactant, an emulsifier, a solubilizer, a polymer, and a buffer.

Embodiment 9. The air freshener device according to any one of Embodiments 7-8, comprising less than about 20 wt % of the ingredient having a functional activity.

Embodiment 10. The air freshener device according to any one of Embodiments 1-9, further comprising a delivery system comprising an element in communication or in contact with the freshening composition.

Embodiment 11. The air freshener device according to Embodiment 10, wherein the delivery system is selected from the group consisting of a reed, a plurality of reeds, a stick, a plurality of sticks, a fiber, a plurality of fibers, a wick, a plurality of wicks, a mesh material, a conductive mesh material, a porous substrate, a semi-porous substrate, and a combination of any of the preceeding delivery systems.

Embodiment 12. The air freshener device according to any one of Embodiments 1-11, further comprising a reservoir having a functionality selected from the group consisting of accepting a freshening composition, receiving a freshening composition, holding a freshening composition, housing a freshening composition and storing a freshening composition.

Embodiment 13. The air freshener device according to Embodiment 12, wherein the reservoir is selected from the group consisting of a bottle, a vessel, and a container.

Embodiment 14. The air freshener device according to any one of Embodiments 1-13, further comprising an evaporative assistance element.

Embodiment 15. The air freshener device according to Embodiment 14, wherein the evaporative assistance element is selected from the group consisting of a heater, a fan, an agitator, and a combination of any of the preceeding evaporative assistance elements.

Embodiment 16. The air freshener device according to Embodiment 15, further comprising a delivery system, wherein the evaporative assistance element is a heater and wherein the heater is configured to heat the delivery system to a temperature in the range from about 45° C. to about 75° C.

Embodiment 17. The air freshener device according to any one of Embodiments 1-16, wherein the perfume raw material comprises a plurality of perfume raw materials It is understood and one of ordinary skill in the art will appreciate that, if not clearly contradicted by the content of this specification, each embodiment of an air freshener device comprising a freshening composition and/or features/elements disclosed as part of that embodiment can be combined with any of the embodiments hereinabove or hereinbelow.

Some embodiments of a method for manufacturing a freshening composition of the present invention are set forth below:

Embodiment 1. A method for manufacturing a freshening composition, the method comprising the step of combining:

(j) from about 0.1 wt % to about 95 wt % perfume raw material, the perfume raw material comprising one or more ingredients selected from the group consisting of an ester, an alcohol, an aldehyde, a ketone, an acetal, a phenol, an ether, a lactone, a furan, a hydrocarbon, an acid, a natural origin fragrance compound, a stereoisomer of any preceeding perfume raw material, and a mixture of any of the preceeding perfume raw materials;

(ii) from about 1.0 wt % to about 95 wt % of a non-glycol ether solvent, a non-glycol ether diluent, or a mixture thereof; and (iii) from about 0.01 wt % to about 90 wt % fragrance release modulator having one or more characteristics selected from the group consisting of:
(a) a flash point higher than about 100° F.,
(b) a surface tension of less than about 60 mN/m,
(c) a dynamic viscosity from about 0.5 cp to about 100 cp, and
(d) a density from about 600 g/l to about 1,300 g/l;
wherein the fragrance release modulator is selected from the group consisting of a $C_{2-8}$ linear alcohol, a $C_{2-8}$ branched alcohol, an alkyl-ether, an aryl-ether, an alkyl-glycol, an aryl-glycol, an alkyl-carbonate, an aryl-carbonate, an alkyldiol, an alkyl-adipate, an aryl-adipate, an alkyl-benzoate, an aryl-benzoate, an alkyl-citrate, an aryl-citrate, an alkyl-laurate, an aryl-laurate, an alkyl-palmitate, an aryl-palmitate, an alkyl-stearate, an aryl-stearate, an aryl-myristate, an alkyl-succinate, an aryl-succinate, an alkyl-glutarate, an aryl-glutarate, a silicon solvent, a stereoisomer of any preceeding fragrance release modulator, and a mixture thereof;

thereby producing a mixture comprising (i), (ii), and (iii).

Embodiment 2. The method according to Embodiment 1, further comprising the step of adapting the freshening composition to have one or more of a characteristic selected from the group consisting of a flash point higher than about 100° F., a surface tension from about 10 mN/m to about 40 mN/m, a dynamic viscosity from about 1 cp to about 30 cp, and a density from about 650 g/l to about 1,300 g/l.

Embodiment 3. The method according to any one of Embodiments 1-2, wherein the perfume raw material comprises a plurality of perfume raw materials.

Embodiment 4. The method according to any one of Embodiments 1-3, wherein the non-glycol ether solvent is selected from the group consisting of an alkyladipate, an aryladipate, an alkyl-glycerol, an aryl-glycerol, an alkyldiol, and aryldiol, an isoparaffine, a silicon, and a mixture of any of the preceeding non-glycol ether solvents.

Embodiment 5. The method according to any one of Embodiments 1-3, wherein the non-glycol ether solvent is selected from the group consisting of 2,2-dimethyl-1,3-dioxolane-4-methanol, 3-methyl-1,3-butanediol-1-acetate, dimethyl adipate, dimethicone, disiloxane, trisiloxane, a $C_{15-19}$alkane, a $C_{13-19}$isoparaffine, a cyclosiloxane, Isopar M®, an alkylcyclosiloxane, an aryl-cyclosiloxane, and a combination of any of the preceeding non-glycol ether solvents.

Embodiment 6. The method according to any one of Embodiments 1-5, wherein the fragrance release modulator is selected from the group consisting of ethanol, n-propanol, iso-propanol, n-butanol, t-butanol, 3-methoxy-3-methyl-1-butanol, 1-pentanol, 2-pentanol, amyl-alcohol, n-pentyl alcohol, 1,3 propanediol, 1,2 hexanediol, 1,2 pentanediol, dimethyl ether, propylene glycol, dipropylene glycol, hexyleneglycol, glycerol, benzyl benzoate, triethylcitrate, dioctyl adipate, propylene carbonate, dimethyl carbonate, isoamyl laurate, methyl palmitate, methyl stearate, dimethyl ether, dimethyl adipate, dimethyl succinate, dimethyl glutarate, n-butyl propionate, dimethicone, disiloxane, trisiloxane, and a mixture of any of the preceeding fragrance release modulators.

Embodiment 7. The method according to any one of Embodiments 1-6, further comprising the step of adding to the mixture comprising (i), (ii) and (iii) less than about 50 wt % of an ingredient having a functional activity and wherein the ingredient having the functional activity is selected from the group consisting of an ingredient having malodor counteracting activity, an ingredient having antimicrobial activity, an ingredient having an insect repellant activity, an ingredient having a preservative activity, an ingredient having an antioxidant activity, an ingredient having a humectant activity, an ingredient having a UV-blocking activity, an ingredient having a pigment activity, an ingredient having a dye activity, an ingredient having a surfactant activity, an ingredient having an emulsifier activity, an ingredient having a solubilizer activity, an ingredient having a polymer activity, and an ingredient having a buffer activity Embodiment 8. The method according to any one of Embodiments 1-6, further comprising the step of adding to the mixture comprising (i), (ii) and (iii) less than about 50 wt % of an ingredient having a functional activity and wherein the ingredient having the functional activity is selected from the group consisting of an ingredient having malodor counteracting activity, an ingredient having antimicrobial activity, an insect repellant, a preservative, an antioxidant, a humectant, a UV-blocking agent, a pigment, a dye, a surfactant, an emulsifier, a solubilizer, a polymer, and a buffer.

It is understood and one of ordinary skill in the art will appreciate that, if not clearly contradicted by the content of this specification, each embodiment of a method for manufacturing a freshening composition and/or features/elements disclosed as part of that embodiment can be combined with any of the embodiments hereinabove or hereinbelow.

Some embodiments of a method for manufacturing an air freshener device comprising a freshening composition of the present invention are set forth below:

Embodiment 1. A method for manufacturing an air freshener device comprising a freshening composition, the method comprising the step of contacting a reservoir in an air freshener device with a freshening composition,
wherein the freshening composition comprises:
(i) from about 0.1 wt % to about 95 wt % perfume raw material, the perfume raw material comprising one or more ingredients selected from the group consisting of an ester, an alcohol, an aldehyde, a ketone, an acetal, a phenol, an ether, a lactone, a furan, a hydrocarbon, an acid, a natural origin fragrance compound, a stereoisomer of any preceeding perfume raw material, and a mixture of any of the preceeding perfume raw materials;
(ii) from about 1.0 wt % to about 95 wt % of a non-glycol ether solvent, a non-glycol ether diluent, or a mixture thereof; and
(iii) from about 0.01 wt % to about 90 wt % fragrance release modulator having one or more characteristics selected from the group consisting of:
(a) a flash point higher than about 100° F.,
(b) a surface tension of less than about 60 mN/m,
(c) a dynamic viscosity from about 0.5 cp to about 100 cp, and
(d) a density from about 600 g/l to about 1,300 g/l;
wherein the fragrance release modulator is selected from the group consisting of a $C_{2-8}$ linear alcohol, a $C_{2-8}$ branched alcohol, an alkyl-ether, an aryl-ether, an alkyl-glycol, an aryl-glycol, an alkyl-carbonate, an aryl-carbonate, an alkyldiol, an alkyl-adipate, an aryl-adipate, an alkyl-benzoate, an aryl-benzoate, an alkyl-citrate, an aryl-citrate, an alkyl-laurate, an aryl-laurate, an alkyl-palmitate, an aryl-palmitate, an alkyl-stearate, an aryl-stearate, an aryl-myristate, an alkyl-succinate, an aryl-succinate, an alkyl-glutarate, an aryl-glutarate, a silicon solvent, a stereoisomer of any preceeding fragrance release modulator, and a mixture of any of the preceeding fragrance release modulators; and
and wherein the freshening composition is adapted to have one or more of a characteristic selected from the group consisting of:
(a) a flash point higher than about 100° F.,
(b) a surface tension from about 10 mN/m to about 40 mN/m,
(c) a dynamic viscosity from about 1 cp to about 30 cp, and
(d) a density from about 650 g/l to about 1,300 g/l.

Embodiment 2. The method according to any one of Embodiment 1, wherein the perfume raw material comprises a plurality of perfume raw materials.

Embodiment 3. The method according to any one of Embodiments 1-2, wherein the non-glycol ether solvent is selected from the group consisting of an alkyladipate, an aryladipate, an alkyl-glycerol, an aryl-glycerol, an alkyldiol, and aryldiol, an isoparaffine, a silicon, and a mixture of any of the preceeding non-glycol ether solvents.

Embodiment 4. The method according to any one of Embodiments 1-2, wherein the non-glycol ether solvent is selected from the group consisting of 2,2-dimethyl-1,3-dioxolane-4-methanol, 3-methyl-1,3-butanediol-1-acetate, dimethyl adipate, dimethicone, disiloxane, trisiloxane, a $C_{15-19}$alkane, a $C_{13-19}$isoparaffine, a cyclosiloxane, Isopar M®, an alkylcyclosiloxane, an aryl-cyclosiloxane, and a combination of any of the preceeding non-glycol ether solvents.

Embodiment 5. The method according to any one of Embodiments 1-4, wherein the fragrance release modulator is selected from the group consisting of ethanol, n-propanol, iso-propanol, n-butanol, t-butanol, 3-methoxy-3-methyl-1-butanol, 1-pentanol, 2-pentanol, amyl-alcohol, n-pentyl alcohol, 1,3 propanediol, 1,2 hexanediol, 1,2 pentanediol, dimethyl ether, propylene glycol, dipropylene glycol, hexyleneglycol, glycerol, benzyl benzoate, triethylcitrate, dioctyl adipate, propylene carbonate, dimethyl carbonate, iso-amyl laurate, methyl palmitate, methyl stearate, dimethyl ether, dimethyl adipate, dimethyl succinate, dimethyl glutarate, n-butyl propionate, dimethicone, disiloxane, trisiloxane, and a mixture of any of the preceeding fragrance release modulators.

Embodiment 6. The method according to any one of Embodiments 1-5, wherein the freshening composition further comprises less than about 50 wt % of an ingredient having a functional activity and wherein the ingredient having the functional activity is selected from the group consisting of an ingredient having malodor counteracting activity, an ingredient having antimicrobial activity, an ingredient having an insect repellant activity, an ingredient having a preservative activity, an ingredient having an antioxidant activity, an ingredient having a humectant activity, an ingredient having a UV-blocking activity, an ingredient having a pigment activity, an ingredient having a dye activity, an ingredient having a surfactant activity, an ingredient having an emulsifier activity, an ingredient having a solubilizer activity, an ingredient having a polymer activity, and an ingredient having a buffer activity Embodiment 7. The method according to any one of Embodiments 1-6, wherein the freshening composition further comprises less than about 50 wt % of an ingredient having a functional activity and wherein the ingredient having the functional activity is selected from the group consisting of an ingredient having malodor counteracting activity, an ingredient having antimicrobial activity, an insect repellant, a preservative, an antioxidant, a humectant, a UV-blocking agent, a pigment, a dye, a surfactant, an emulsifier, a solubilizer, a polymer, and a buffer.

Embodiment 8. The method according to any one of Embodiments 7-8, comprising less than about 20 wt % of the ingredient having a functional activity.

Embodiment 9. The method according to any one of Embodiments 1-9, wherein the air freshener device further comprises a delivery system and wherein the delivery system comprises an element in communication or in contact with the freshening composition.

Embodiment 10. The method according to Embodiment 9, wherein the delivery system is selected from the group consisting of a reed, a plurality of reeds, a stick, a plurality of sticks, a fiber, a plurality of fibers, a wick, a plurality of wicks, a mesh material, a conductive mesh material, a porous substrate, a semi-porous substrate, and a combination of any of the preceeding delivery systems.

Embodiment 11. The method according to any one of Embodiments 1-10, wherein the reservoir has a functionality selected from the group consisting of accepting a freshening composition, receiving a freshening composition, holding a freshening composition, housing a freshening composition and storing a freshening composition.

Embodiment 12. The method according to Embodiment 11, wherein the reservoir is selected from the group consisting of a bottle, a vessel, and a container.

Embodiment 13. The method according to any one of Embodiments 1-12, wherein the air freshener device further comprises an evaporative assistance element.

Embodiment 14. The method according to Embodiment 13, wherein the evaporative assistance element is selected from the group consisting of a heater, a fan, an agitator, and a combination of any of the preceeding evaporative assistance elements.

Embodiment 15. The method according to Embodiment 14, wherein the air freshener device further comprises a delivery system, wherein the evaporative assistance element is a heater and wherein the heater is configured to heat the delivery system to a temperature in the range from about 45° C. to about 75° C.

It is understood and one of ordinary skill in the art will appreciate that, if not clearly contradicted by the content of this specification, each embodiment of a method for manufacturing an air freshener comprising a freshening composition and/or features/elements disclosed as part of that embodiment can be combined with any of the embodiments hereinabove or hereinbelow.

DETAILED DESCRIPTION OF THE INVENTION

I. Definitions

Figure 1:
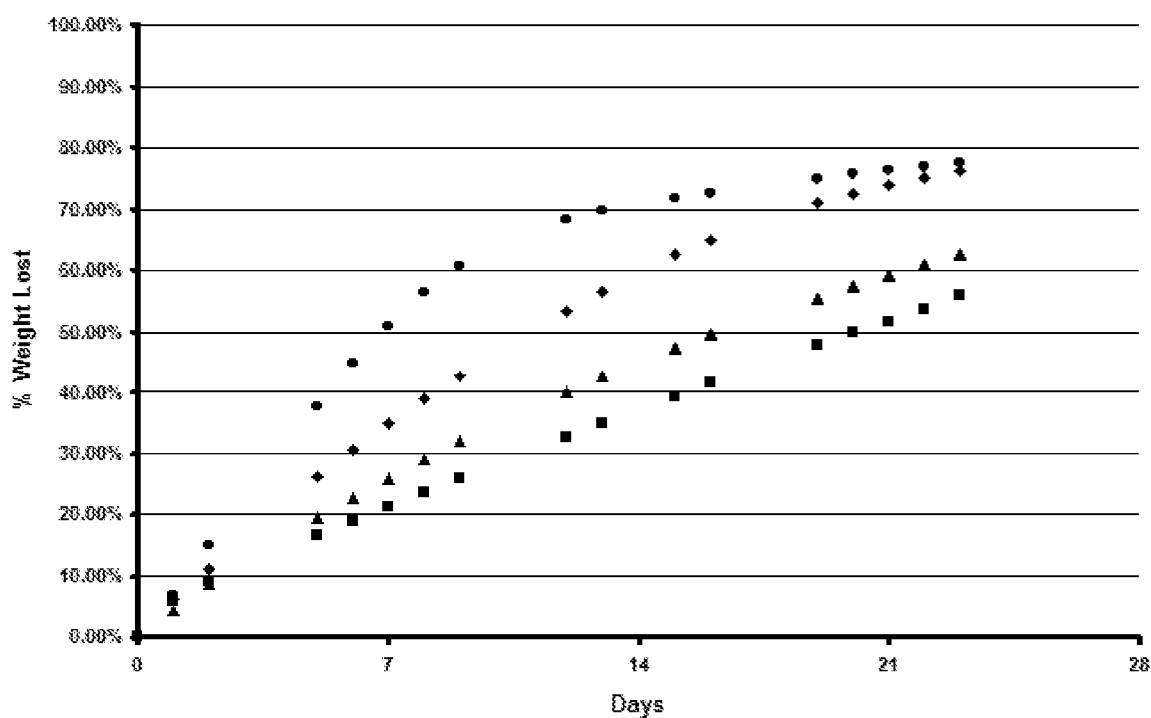
FIG. 1 schematically depicts the influence of different solvents on the release and evaporation of a freshening composition comprising 50 wt % Apple Fragrance (see, Table 9) and 50 wt % solvents as indicated and measured as % weight lost during the time period indicated. The weight percentage refers to the weight percentage of the entire product formulation, i.e., freshening composition. The following solvents were tested: ■, acetone monoglycerol ketal (Augeo Clean Multi® from Solvay); ♦, 3-methyl-1,3-butanediol-acetate (IPD-AC® from Kuraray); ▲ STA-SOL® ESS 165 (dimethyl adipate (DMA) from ST Laboratories Inc.); ●, silicon solvent (VOLASIL® DM-2 from CHEMSIL Silicones, Inc.). Details are described in Example C.

Throughout the present specification and the accompanying claims the words "comprise," "include," and "have" and variations thereof such as "comprises," "comprising," "includes," "including," "has," and "having" are to be interpreted inclusively. That is, these words are intended to convey the possible inclusion of other elements or integers not specifically recited, where the context allows. The term "consisting essentially of" means that the composition, method or structure may include additional ingredients, steps and/or parts, but only if the additional ingredients, steps and/or parts do not materially alter the basic and novel characteristics of the claimed composition, method or structure. As used herein, the term "consisting of" is intended to mean including and limited to whatever follows the phrase "consisting of". Thus the phrase "consisting of" indicates that the listed elements are required or mandatory and that no other elements may be present. No language in the specification should be construed as indicating any non-claimed element essential to the practice of the invention.

The terms "a" and "an" and "the" and similar referents used in the context of describing the invention (especially in the context of the following claims) are to be construed to cover both the singular and the plural, unless otherwise indicated herein or clearly contradicted by context.

The term "and/or" where used herein is to be taken as specific disclosure of each of the two specified features or components with or without the other. For example, "A and/or B" is to be taken as specific disclosure of each of (i) A, (ii) B, and (iii) A and B, just as if each is set out individually herein.

Recitation of ranges of values herein are merely intended to serve as a shorthand method of referring individually to each separate value falling within the range, unless otherwise indicated herein, each individual value is incorporated into the specification as if it were individually recited herein. Ranges may be expressed herein as from "about" (or "approximate") one particular value, and/or to "about" (or "approximate") another particular value. When such a range is expressed, an embodiment includes values from the one particular value to the other particular value. Similarly, when values are expressed as approximations, by use of the antecedent "about" or "approximate" it will be understood that the particular value forms another embodiment. It will be further understood that the endpoints of each of the ranges are significant both in relation to the other endpoint, and independently of the other endpoint. With respect to endpoints of ranges, it is understood that when a range is given herein, it discloses alternative ranges, without specifically reciting them, i.e., (a) an "of/from—to" range in which the endpoints are included in the range and (b) an "between—and" range, in which the endpoints are excluded from the range. For example, a disclosure of a freshening composition comprising about 0.1 wt % to about 95 wt % perfume raw material includes (a) a composition comprising the perfume raw material from about 0.1 wt % to about 95 wt %, in which the endpoints 0.1 wt % and 95 wt % are included, and (b) a composition comprising the perfume raw material between about 0.1 wt % and about 95 wt %, in which the endpoints 0.1 wt % and 95 wt % are excluded. Thus, every range defined herein in the format "from/of—to" is to be understood as also disclosing a separate and discrete range defined as "between—and." Likewise, every range defined herein in the format "between—and" is to be understood as also disclosing a separate and discrete range defined as "from/of—to." It is also understood that there are a number of values disclosed herein, and that each value is also herein disclosed as "about" that particular value in addition to the value itself. For example, if the value "10" is disclosed, then "about 10" is also disclosed. Further, the term "about" applies to both cited endpoints of a range, even when it is written only before the lower endpoint. For example, "about X to Y" should be interpreted as "about X to about Y." It is also understood that when a value is disclosed that is "less than or equal to the value" or "greater than or equal to the value" possible ranges between these values are also disclosed, as appropriately understood by the skilled artisan. For example, if the value "10" is disclosed the "less than or equal to 10" as well as "greater than or equal to 10" is also disclosed.

In the following description it is to be understood that terms such as "forward," "rearward," "front," "back," "right," "left," "upward," "downward," "horizontal," "vertical," "longitudinal," "lateral," "angular," "first," "second" and the like are words of convenience and are not to be construed as limiting terms.

All methods described herein can be performed in any suitable order unless otherwise indicated herein or otherwise clearly contradicted by context. Further, all methods described herein and having more than one step can be performed by more than one person or entity. Thus, a person or an entity can perform step (a) of a method, another person or another entity can perform step (b) of the method, and a yet another person or a yet another entity can perform step (c) of the method, etc. The use of any and all examples, or exemplary language (e. g. "such as") provided herein is intended merely to better illuminate the invention and does not pose a limitation on the scope of the invention otherwise claimed.

Units, prefixes, and symbols are denoted in their Système International de Unites (SI) accepted form. The abbreviations used herein have their conventional meaning within the mechanical, chemical, and biological arts.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

The headings used herein are for organizational purposes only and are not meant to be used to limit the scope of the description or the claims, which can be had by reference to the specification as a whole. Accordingly, the terms defined immediately below are more fully defined by reference to the specification in its entirety.

Illustrations are for the purpose of describing a preferred embodiment of the invention and are not intended to limit the invention thereto.

Unless defined otherwise, all technical and scientific terms used herein have the meaning commonly understood by a person skilled in the art to which this invention belongs. The following references provide one of skill with a general definition of many of the terms used in this invention: The Cambridge Dictionary of Science and Technology (Walker ed., 1988). As used herein, the following terms have the meanings ascribed to them unless specified otherwise.

As used herein, the terms "about" or "approximately" refer to a range of values of plus or minus 20%, preferably, plus or minus 10%, more preferably, plus or minus 5% of a specified value, and more preferably, plus or minus 4% of a specified value, plus or minus 3% of a specified value, plus or minus 2% of a specified value, plus or minus 1% of a specified value, and/or plus or minus 0% of a specified value. For example, the phrase "about 200" includes plus or minus 20% of 200, or from 160 to 240, preferably, plus or minus 10% of 200, or from 180 to 220, more preferably, plus or minus 5% of 200, or from 190 to 210. It includes, also the specified value or concrete number, e.g., "about 200" includes 200.

The terms "agent," "compound," and "ingredient," unless clearly contradicted by context, are used interchangeably herein. As used herein, an "agent" can be any chemical compound, for example, a macromolecule or a small molecule. An agent can have a formula weight of less than about 100,000 grams per mole, less than 50,000 grams per mole, less than 10,000 grams per mole, less than 5,000 grams per mole, less than 1,000 grams per mole, or less than about 500 grams per mole. An agent can be naturally occurring (e.g., an herb or a nature product), synthetic, or both. Examples of macromolecules are proteins, protein complexes, and glycoproteins, nucleic acids, e.g., DNA, RNA and PNA (peptide nucleic acid). Examples of small molecules are peptides, peptidomimetics (e.g., peptoids), amino acids, amino acid analogs, polynucleotides, polynucleotide analogs, nucleotides, nucleotide analogs, organic or inorganic compounds e.g., heteroorganic or organometallic compounds. An agent can be the only substance assayed by a method described herein. Alternatively, a collection of agents can be assayed either consecutively or concurrently by methods described herein.

As used herein, the term "alkyl," by itself or as part of another substituent, means, unless otherwise stated, a straight (i.e. unbranched) or branched chain, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

As used herein, the term "air care product" refers to a product or device for treating or fragrancing air or a surface. It includes, but is not limited to, a spray, an energized (e.g., electrically powered) air freshening delivery system, such as a fan-based diffuser, a liquid electric pluggable air freshener, an electromechanical actuating diffuser, a passive diffuser (e.g., not electrically powered) including, but not limited to a wicking air freshener, such as a reed diffuser, a steam-based freshener, or a membrane-based air freshener, such as a car vent air freshener.

As used herein, the terms "alter," "alteration," "altering," "modulate," modulation," "modulating," and grammatical equivalents thereof are art-recognized and refer to up-regulation (i.e., activation, stimulation, increase), or down-regulation (i.e., inhibition, suppression, reduction, or decrease) of a response, or the two in combination or apart.

As used herein, the term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. The term "aryl" when used in combination with other terms (e.g., arylether, arylglycol, arylcarbonate, aryladipate, arylbenzoate, arylcitrate, aryllaureate, arylpalmitate, arylstearate, arylmyristate, arylsuccinate, arylglutarate, aryloxy, arylthioxy, arylalkyl, and the like) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

As used herein, the terms "connect to," connected to," "attach to" or "attached to" or grammatical equivalents thereof mean to fasten on, to fasten together, to affix to, to mount to, mount on, to connect to, to join, to position onto, to position into, to place onto, or to place into. "Attachment" means the act of attaching or the condition of being attached. Attachment can be direct or indirectly. For example a part A may be attached directly to part B. Alternatively, part A may be attached indirectly to part B through first attaching part A to part C and then attaching part C to part B. More than one intermediary part may be used to attach part A to part B. Attaching can be permanent, temporarily, or for a prolonged time. For example, an air care product or device of the present invention may be attached to a structure, an object, an outlet, etc. temporarily for the time necessary to perform a method of the invention. Alternatively, an air care product or device of the present invention may be attached to a structure, an object, an outlet for a prolonged time, e.g., also when a method of the present invention is not performed.

As used herein, the terms "contacting," "to contact," "contacted to," "contacted with," or grammatical equivalents thereof are used interchangeably with the following: combining with, adding to, mixing with, passing over, incubating with, flowing over, etc. The term "contacting" also includes reference to placement of one substance, e.g., a freshening composition or a component of a freshening composition, as described herein, in direct physical contact or association with another component, such as a reservoir, or with another substance, such as the atmosphere, air or a surface.

As used herein, the term "different" means not the same, not the same identity.

As used herein, the terms "effective amount", "effective dose", "sufficient amount", "amount effective to" or grammatical equivalents thereof mean a dosage sufficient to produce a desired result, whether permanent or temporary, lasting or transit that can be associated with the administration of a composition of the present invention. An"effective amount," an "effective dose," a "sufficient amount," or an "amount effective to" in the context of embodiments of the present invention can be determined by one of ordinary skill in the art using the disclosure of the present application, in particular, the Examples.

As used herein, the term "fragrance release modulator," abbreviated "FRM," refers to a compound having the capability of modulating the release or evaporation of a freshening composition, when said fragrance release modulator is added to or combined with a perfume raw material as described herein. Release or evaporation of a freshening composition can be tested as described herein.

As used herein, the term "freshening composition" refers to a composition that comprises one or more perfume raw materials and which may be used to treat, fragrance, and/or fresh the air. A freshening composition may be used with or without an air care product, referred to herein from time to time as an air freshener device. A freshening composition can be in a liquid form.

As used herein, the terms "greater than" or "more than" include the concrete number. For example, greater than 100 or more than 100 mean greater than or equal to 100 or more than or equal to 100. As used herein, the terms "smaller than," "fewer than." or "less than" include the concrete number. For example, smaller than 100, fewer than 100, or less than 100 mean smaller than or equal to 100, fewer than or equal to 100, or less than or equal to 100.

As used herein, the terms "ingredient having antimicrobial activity" or "antimicrobial ingredient" refer to a compound having the capability of eliminating, reducing or minimizing the presence, occurrence, or growth of microorganisms, such as bacteria, yeasts or molds.

As used herein, the term "ingredient having malodor counteracting activity" refers to a compound having the capability of eliminating, reducing or minimizing a malodor.

As used herein, the term "isomer" refers to compounds that have the same molecular formula but differ in the nature or sequence of bonding of their atoms or the arrangement of their atoms in space. Isomers that differ in the arrangement of their atoms in space are termed "stereoisomers." "Stereoisomer" and "stereoisomers" refer to compounds that exist in different stereoisomeric forms if they possess one or more asymmetric centers or a double bond with asymmetric substitution and, therefore, can be produced as individual stereoisomers or as mixtures. Stereoisomers include enantiomers and diastereomers. Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Unless otherwise indicated, the description of compounds herein is intended to include individual stereoisomers as well as mixtures. The methods for the determination of stereochemistry and the separation of stereoisomers are well known in the art (see, discussion in Chapter 4 of ADVANCED ORGANIC CHEMISTRY, 4th edition J. March, John Wiley and Sons, New York, 1992) differ in the chirality of one or more stereocenters.

The terms "modulate," "modulation," or "modulating" are art-recognized and refer to up-regulation (i.e., activation, stimulation, increase, facilitation, enhancement), or down regulation (i.e., inhibition, suppression, reduction, or decrease) of a response, or the two in combination or apart. Thus, as used herein, the term modulate encompasses up-regulation (i.e., activation, stimulation, increase, facilitation, enhancement), or down regulation (i.e., inhibition, suppression, reduction, or decrease) of a response. In some embodiments, of particular interest are compounds, referred to herein as fragrance release modulator, which have the capability to modulate the release or evaporation of a freshening composition. In some embodiments of the present invention, a fragrance release modulator of the present invention up-regulates the release or evaporation of a freshening composition, relative to a control (not comprising said fragrance release modulator and assigned a value of 100%) by at least about 10%, by at least about 20%, by at least about 30%, by at least about 40%, by at least about 50%, by at least about 60%, by at least about 70%, by at least about 80%, by at least about 90%, by at least about 100%, by at least about 110%, by at least about 120%, by at least about 130%, by at least about 140%, by at least about 150%, by at least about 160%, by at least about 170%, by at least about 180%, by at least about 190%, by at least about 200%, by at least about 250%, by at least about 300%, by at least about 400%, by at least about 500%, or by at least about 1,000-3,000% or more. In some embodiments of the present invention, a fragrance release modulator of the present invention down-regulates the release or evaporation of a freshening composition, relative to a control (not comprising said fragrance release modulator and assigned a value of 100%) by at least about 5%, by at least about 10%, by at least about 15%, by at least about 20%, by at least about 25%, by at least about 30%, by at least about 35%, by at least about 40%, by at least about 45%, by at least about 50%, by at least about 55%, by at least about 60%, by at least about 65%, by at least about 70%, by at least about 75%, by at least about 80%, by at least about 85%, by at least about 90%, by at least about 95% or more.

As used herein, the term "natural origin fragrance compound" refers to a compound isolated or purified from a natural origin and wherein said isolated or purified compound retains the smell, scent or hedonic benefit one of ordinary skill in the art would associate with said natural origin. As a non-limiting example, a compound isolated from a grapefruit will be referred to herein as a natural origin fragrance if that compound retains a smell, scent or hedonic benefit one of ordinary skill in the art would associate with a grapefruit.

As used herein, "optional" or "optionally" means that the subsequently described event, component, element, feature, or circumstance may or may not occur or may or may not be present, and that the description includes instances where said event, component, element, feature or circumstance occurs and/or is present and instances where said event, component, element, feature or circumstance does not occur and/or is not present. As a non-limiting example, a composition A may optionally comprise compound B. In that example, the invention provides (i) a composition A comprising compound B and (ii) a composition not comprising compound B.

As used herein, the term "treating or fragrancing air or a surface" refers to a process resulting in delivering an air freshening composition or a component thereof into the air or bringing an air freshening composition or a component thereof into contact with a surface and producing a desired result. In some embodiments of the present invention, such desired result is eliminating, reducing or minimizing a malodor.

Where appropriate and not contradicted by the disclosure herein, embodiments and elements/features within individual embodiments may be freely combined with those of other embodiments. As a non-limiting example, a preferred viscosity disclosed within the context of a composition itself will also be disclosed within the context of an air care product or device comprising that composition, without specifically reciting again such preferred viscosity in the context of such air care product or device. Thus, unless defined otherwise, and where consistent with the teaching herein, any feature within any embodiment of the invention may be combined with any feature within any other embodiment of the invention, and the skilled person understands and appreciates such combination as being encompassed in the original disclosure of the present application. This applies in particular to embodiments relating to freshening compositions per se, in respect to other embodiments relating to air freshener devices comprising a freshening composition, methods for manufacturing freshening compositions, methods for manufacturing air freshener devices comprising a freshening composition, methods of using a freshening composition, and/or methods for using an air freshener device comprising a freshening composition, including any interrelationship of such embodiments. This also applies in particular to embodiments relating to the various ingredients in a freshening composition, for example, the choice of perfume raw material or materials as well as its/their amount/s and physical characteristic/s, the choice of functional ingredient or ingredients as well as its/their amount/s and physical characteristic/s, the choice of fragrance release modulator or modulators and its/their amount/s and physical characteristic/s, and/or the choice of solvent, diluent, and solubilizer or solvents, diluents, and solubilizers and its/their amount/s and physical characteristic/s.

II. Freshening Compositions

The present invention provides freshening compositions. It is understood and one of ordinary skill in the art will appreciate that, if not clearly contradicted by the content of this specification, each embodiment of a freshening composition and/or features/elements disclosed as part of that embodiment can be combined with any of the embodiments hereinabove or hereinbelow. In some embodiments of the present invention, a freshening composition is an air freshening composition. As described herein, an air freshening composition may be used, e.g., to fresh the atmosphere, the air or a surface, to fragrance the atmosphere, the air or fragrance a surface.

In some embodiments of the present invention, a freshening composition is a liquid freshening composition. As will be understood by one of skilled in the art, a liquid freshening composition consists primarily of a liquid composition and is substantially devoid of solid components.

In some embodiments of the present invention, a freshening composition is a clear freshening composition. As will be understood by one of skilled in the art, a clear freshening composition is a transparent, see-through or translucent composition.

In some embodiments of the present invention, a freshening composition is a homogeneous freshening composition. As will be understood by one of skilled in the art, a homogeneous freshening composition is a uniform composition.

In some embodiments of the present invention, a freshening composition is a liquid air freshening composition. In some embodiments of the present invention, a freshening composition is a clear liquid freshening composition. In some embodiments of the present invention, a freshening composition is a clear liquid air freshening composition. In some embodiments of the present invention, a freshening composition is a homogeneous, clear liquid air freshening composition. Each of the above combines the characteristics and attributes of the individual composition.

For ease, when referring herein to "freshening composition," it is understood that this term includes (i) an air freshening composition, (ii) a liquid freshening composition, (iii) a clear freshening composition, (iv) a homogeneous freshening composition, (v) a liquid air freshening composition, (vi) a clear air freshening composition, (vii) a clear liquid air freshening composition, and (viii) a homogeneous, clear liquid air freshening composition.

In some embodiments of the present invention, a freshening composition comprises a perfume raw material ("PRM"). The "PRMs" disclosed herein, claimed and/or used in a freshening composition comprise stereoisomers of such materials.

In some embodiments of the present invention, a freshening composition comprises a solvent or diluent. The solvents or diluents disclosed herein, claimed and/or used in a freshening composition comprise stereoisomers of such materials.

In some embodiments of the present invention, a freshening composition comprises a fragrance release modulator (FRM). The fragrance release modulators (FRMs) disclosed herein, claimed and/or used in a freshening composition comprise stereoisomers of such materials.

In some embodiments of the present invention, a freshening composition comprises a solvent or diluent and a fragrance release modulator.

Freshening compositions of the present invention can be characterized by their flash point, surface tension, dynamic viscosity, density, vapor pressure, and evaporation rates. Values for flash point, surface tension, dynamic viscosity, density, and evaporation rate provided herein are measured under normal temperature and pressure (NTP) conditions.

In some embodiments of the present invention, a freshening composition has a flash point in the range from about 100° C. to about 250° C. In some embodiments of the present invention, a freshening composition has a flash point in the range from about 110° C. to about 250° C. In some embodiments of the present invention, a freshening composition has a flash point in the range from about 120° C. to about 250° C. In some embodiments of the present invention, a freshening composition has a flash point in the range from about 130° C. to about 250° C. In some embodiments of the present invention, a freshening composition has a flash point in the range from about 140° C. to about 250° C. In some embodiments of the present invention, a freshening composition has a flash point in the range from about 150° C. to about 240° C. In some embodiments of the present invention, a freshening composition has a flash point in the range from about 160° C. to about 230° C. In some embodiments of the present invention, a freshening composition has a flash point in the range from about 170° C. to about 200° C.

In some embodiments of the present invention, a freshening composition has a flash point in the range of between about 100° C. and about 250° C. In some embodiments of the present invention, a freshening composition has a flash point in the range of between about 110° C. and about 250° C. In some embodiments of the present invention, a freshening composition has a flash point in the range of between about 120° C. and about 250° C. In some embodiments of the present invention, a freshening composition has a flash point in the range of between about 130° C. and about 250° C. In some embodiments of the present invention, a freshening composition has a flash point in the range of between about 140° C. and about 250° C. In some embodiments of the present invention, a freshening composition has a flash point in the range of between about 150° C. and about 240° C. In some embodiments of the present invention, a freshening composition has a flash point in the range of between about 160° C. and about 230° C. In some embodiments of the present invention, a freshening composition has a flash point in the range of between about 170° C. and about 200° C.

In some embodiments of the present invention, a freshening composition has a flash point of greater than about 100° F. In some embodiments of the present invention, a freshening composition has a flash point of greater than about 110° F. In some embodiments of the present invention, a freshening composition has a flash point of greater than about 120° F. In some embodiments of the present invention, a freshening composition has a flash point of greater than about 130° F. In some embodiments of the present invention, a freshening composition has a flash point of greater than about 140° F. In some embodiments of the present invention, a freshening composition has a flash point of greater than about 150° F. In some embodiments of the present invention, a freshening composition has a flash point of greater than about 160° F. In some embodiments of the present invention, a freshening composition has a flash point of greater than about 170° F. In some embodiments of the present invention, a freshening composition has a flash point of greater than about 180° F. In some embodiments of the present invention, a freshening composition has a flash point of greater than about 190° F. In some embodiments of the present invention, a freshening composition has a flash point of greater than about 200° F. In some embodiments of the present invention, a freshening composition has a flash point of greater than about 210° F. In some embodiments of the present invention, a freshening composition has a flash point of greater than about 220° F. In some embodiments of the present invention, a freshening composition has a flash point of greater than about 230° F. In some embodiments of the present invention, a freshening composition has a flash point of greater than about 240° F. In some embodiments of the present invention, a freshening composition has a flash point of greater than about 250° F. In some embodiments of the present invention, a freshening composition has a flash point of greater than about 260° F.

In some embodiments of the present invention, a freshening composition has a flash point of less than about 100° F. In some embodiments of the present invention, a freshening composition has a flash point of less than about 110° F. In some embodiments of the present invention, a freshening composition has a flash point of less than about 120° F. In some embodiments of the present invention, a freshening composition has a flash point of less than about 130° F. In some embodiments of the present invention, a freshening composition has a flash point of less than about 140° F. In some embodiments of the present invention, a freshening composition has a flash point of less than about 150° F. In some embodiments of the present invention, a freshening composition has a flash point of less than about 160° F. In some embodiments of the present invention, a freshening composition has a flash point of less than about 170° F. In some embodiments of the present invention, a freshening composition has a flash point of less than about 180° F. In some embodiments of the present invention, a freshening composition has a flash point of less than about 190° F. In some embodiments of the present invention, a freshening composition has a flash point of less than about 200° F. In some embodiments of the present invention, a freshening composition has a flash point of less than about 210° F. In some embodiments of the present invention, a freshening composition has a flash point of less than about 220° F. In some embodiments of the present invention, a freshening composition has a flash point of less than about 230° F. In some embodiments of the present invention, a freshening composition has a flash point of less than about 240° F. In some embodiments of the present invention, a freshening composition has a flash point of less than about 250° F. In some embodiments of the present invention, a freshening composition has a flash point of less than about 260° F.

Surface tension is the tendency of a fluid surface to shrink into the minimum surface area possible. Because of the relatively high attraction of water molecules to each other through hydrogen bonds, water has a higher surface tension (72.8 millinewtons per meter [mN/m] at 20° C.) than most other liquids. In some embodiments of the present invention, a freshening composition has a surface tension in the range from about 5 mN/m to about 100 mN/m. In some embodiments of the present invention, a freshening composition has a surface tension in the range from about 10 mN/m to about 90 mN/m. In some embodiments of the present invention, a freshening composition has a surface tension in the range from about 15 mN/m to about 80 mN/m. In some embodiments of the present invention, a freshening composition has a surface tension in the range from about 20 mN/m to about 70 mN/m. In some embodiments of the present invention, a freshening composition has a surface tension in the range from about 20 mN/m to about 60 mN/m. In some embodiments of the present invention, a freshening composition has a surface tension in the range from about 20 mN/m to about 50 mN/m.

In some embodiments of the present invention, a freshening composition has a surface tension in the range of between about 5 mN/m and about 100 mN/m. In some embodiments of the present invention, a freshening composition has a surface tension in the range of between about 10 mN/m and about 90 mN/m. In some embodiments of the present invention, a freshening composition has a surface tension in the range of between about 15 mN/m and about 80 mN/m. In some embodiments of the present invention, a freshening composition has a surface tension in the range of between about 20 mN/m and about 70 mN/m. In some embodiments of the present invention, a freshening composition has a surface tension in the range of between about 20 mN/m and about 60 mN/m. In some embodiments of the present invention, a freshening composition has a surface tension in the range of between about 20 mN/m and about 50 mN/m.

In some embodiments of the present invention, a freshening composition has a surface tension of greater than about 5 mN/m, alternatively, greater than about 10 mN/m, alternatively, greater than about 15 mN/m, alternatively, greater than about 20 mN/m, alternatively, greater than about 25 mN/m, alternatively, greater than about 30 mN/m, alternatively, greater than about 35 mN/m, alternatively, greater than about 40 mN/m, alternatively, greater than about 45 mN/m, alternatively, greater than about 50 mN/m, alternatively, greater than about 55 mN/m, alternatively, greater than about 60 mN/m, alternatively, greater than about 65 mN/m, alternatively, greater than about 70 mN/m, alternatively, greater than about 75 mN/m, alternatively, greater than about 80 mN/m, alternatively, greater than about 85 mN/m, alternatively, greater than about 90 mN/m, alternatively, greater than about 95 mN/m, alternatively, greater than about 100 mN/m.

In some embodiments of the present invention, a freshening composition has a surface tension of less than about 5 mN/m, alternatively, less than about 10 mN/m, alternatively, less than about 15 N/m, alternatively, less than about 20 mN/m, alternatively, less than about 25 mN/m, alternatively, less than about 30 mN/m, alternatively, less than about 35 mN/m, alternatively, less than about 40 mN/m, alternatively, less than about 45 mN/m, alternatively, less than about 50 mN/m, alternatively, less than about 55 mN/m, alternatively, less than about 60 mN/m, alternatively, less than about 65 mN/m, alternatively, less than about 70 mN/m, alternatively, less than about 75 mN/m, alternatively, less than about 80 mN/m, alternatively, less than about 85 mN/m, alternatively, less than about 90 mN/m, alternatively, less than about 95 mN/m, alternatively, less than about 100 mN/m.

A preferred freshening composition of the present invention has a surface tension in the range from about 10 mN/m to about 40 mN/m. A preferred freshening composition of the present invention has a surface tension in the range from about 20 mN/m to about 35 mN/m.

The SI (International System of Units) unit of a dynamic viscosity is the pascal-second (Pa-s), or equivalent kilogram per meter per second (kg*m$^{-1}$*s$^{-1}$). The CGS (Centimetre-gram-second system of units) unit is called the poise (P). It is commonly expressed, particularly in ASTM (American Society for Testing and Materials) standards, as centipoise (cp) since the latter is equal to the SI multiple millipascal seconds (mPA-s).

In some embodiments of the present invention, a freshening composition has a dynamic viscosity range in the range of between about 0.1 cp and about 150 cp. In some embodiments of the present invention, a freshening composition has a dynamic viscosity range in the range of between about 0.2 cp and about 140 cp. In some embodiments of the present invention, a freshening composition has a dynamic viscosity range in the range of between about 0.3 cp and about 130 cp. In some embodiments of the present invention, a freshening composition has a dynamic viscosity range in the range of between about 0.5 cp and about 120 cp. In some embodiments of the present invention, a freshening composition has a dynamic viscosity range in the range of between about 0.7 cp and about 110 cp. In some embodiments of the present invention, a freshening composition has a dynamic viscosity range in the range of between about 0.8 cp and about 100 cp. In some embodiments of the present invention, a freshening composition has a dynamic viscosity range in the range of between about 1 cp and about 100 cp. In some embodiments of the present invention, a freshening composition has a dynamic viscosity range in the range of between about 1 cp and about 90 cp. In some embodiments of the present invention, a freshening composition has a dynamic viscosity range in the range of between about 1 cp and about 80 cp. In some embodiments of the present invention, a freshening composition has a dynamic viscosity range in the range of between about 1 cp and about 70 cp. In some embodiments of the present invention, a freshening composition has a dynamic viscosity range in the range of between about 1 cp and about 60 cp. In some embodiments of the present invention, a freshening composition has a dynamic viscosity range in the range of between about 1 cp and about 50 cp. In some embodiments of the present invention, a freshening composition has a dynamic viscosity range in the range of between about 1 cp and about 40 cp. In some embodiments of the present invention, a freshening composition has a dynamic viscosity range in the range of between about 1 cp and about 30 cp. In some embodiments of the present invention, a freshening composition has a dynamic viscosity range in the range of between about 1 cp and about 20 cp. In some embodiments of the present invention, a freshening composition has a dynamic viscosity range in the range of between about 1 cp and about 10 cp.

In some embodiments of the present invention, a freshening composition has a dynamic viscosity range in the range from about 0.1 cp to about 150 cp. In some embodiments of the present invention, a freshening composition has a dynamic viscosity range in the range from about 0.2 cp to about 140 cp. In some embodiments of the present invention, a freshening composition has a dynamic viscosity range in the range from about 0.3 cp to about 130 cp. In some embodiments of the present invention, a freshening composition has a dynamic viscosity range in the range from about 0.5 cp to about 120 cp. In some embodiments of the present invention, a freshening composition has a dynamic viscosity range in the range from about 0.7 cp to about 110 cp. In some embodiments of the present invention, a freshening composition has a dynamic viscosity range in the range from about 0.8 cp to about 100 cp. In some embodiments of the present invention, a freshening composition has a dynamic viscosity range in the range from about 1 cp to about 100 cp. In some embodiments of the present invention, a freshening composition has a dynamic viscosity range in the range from about 1 cp to about 90 cp. In some embodiments of the present invention, a freshening composition has a dynamic viscosity range in the range from about 1 cp to about 80 cp. In some embodiments of the present invention, a freshening composition has a dynamic viscosity range in the range from about 1 cp to about 70 cp. In some embodiments of the present invention, a freshening composition has a dynamic viscosity range in the range from about 1 cp to about 60 cp. In some embodiments of the present invention, a freshening composition has a dynamic viscosity range in the range from about 1 cp to about 50 cp. In some embodiments of the present invention, a freshening composition has a dynamic viscosity range in the range from about 1 cp to about 40 cp. In some embodiments of the present invention, a freshening composition has a dynamic viscosity range in the range from about 1 cp to about 30 cp. In some embodiments of the present invention, a freshening composition has a dynamic viscosity range in the range from about 1 cp to about 20 cp. In some embodiments of the present invention, a freshening composition has a dynamic viscosity range in the range from about 1 cp to about 10 cp.

In some embodiments of the present invention, a freshening composition has a dynamic viscosity of greater than about 0.1 cp. In some embodiments of the present invention, a freshening composition has a dynamic viscosity of greater than about 0.2 cp. In some embodiments of the present invention, a freshening composition has a dynamic viscosity of greater than about 0.3 cp. In some embodiments of the present invention, a freshening composition has a dynamic viscosity of greater than about 0.4 cp. In some embodiments of the present invention, a freshening composition has a dynamic viscosity of greater than about 0.5 cp. In some embodiments of the present invention, a freshening composition has a dynamic viscosity of greater than about 0.7 cp. In some embodiments of the present invention, a freshening composition has a dynamic viscosity of greater than about 1 cp. In some embodiments of the present invention, a freshening composition has a dynamic viscosity of greater than about 2 cp. In some embodiments of the present invention, a freshening composition has a dynamic viscosity of greater than about 3 cp. In some embodiments of the present invention, a freshening composition has a dynamic viscosity of greater than about 5 cp. In some embodiments of the present invention, a freshening composition has a dynamic viscosity of greater than about 7 cp. In some embodiments of the present invention, a freshening composition has a dynamic viscosity of greater than about 10 cp. In some embodiments of the present invention, a freshening composition has a dynamic viscosity of greater than about 15 cp. In some embodiments of the present invention, a freshening composition has a dynamic viscosity of greater than about 20 cp. In some embodiments of the present invention, a freshening composition has a dynamic viscosity of greater than about 25 cp. In some embodiments of the present invention, a freshening composition has a dynamic viscosity of greater than about 30 cp. In some embodiments of the present invention, a freshening composition has a dynamic viscosity of greater than about 35 cp. In some embodiments of the present invention, a freshening composition has a dynamic viscosity of greater than about 40 cp. In some embodiments of the present invention, a freshening composition has a dynamic viscosity of greater than about 45 cp. In some embodiments of the present invention, a freshening composition has a dynamic viscosity of greater than about 50 cp.

In some embodiments of the present invention, a freshening composition has a dynamic viscosity of less than about 0.1 cp. In some embodiments of the present invention, a freshening composition has a dynamic viscosity of less than about 0.2 cp. In some embodiments of the present invention, a freshening composition has a dynamic viscosity of less than about 0.3 cp. In some embodiments of the present invention, a freshening composition has a dynamic viscosity of less than about 0.4 cp. In some embodiments of the present invention, a freshening composition has a dynamic viscosity of less than about 0.5 cp. In some embodiments of the present invention, a freshening composition has a dynamic viscosity of less than about 0.7 cp. In some embodiments of the present invention, a freshening composition has a dynamic viscosity of less than about 1 cp. In some embodiments of the present invention, a freshening composition has a dynamic viscosity of less than about 2 cp. In some embodiments of the present invention, a freshening composition has a dynamic viscosity of less than about 3 cp. In some embodiments of the present invention, a freshening composition has a dynamic viscosity of less than about 5 cp. In some embodiments of the present invention, a freshening composition has a dynamic viscosity of less than about 7 cp. In some embodiments of the present invention, a freshening composition has a dynamic viscosity of less than about 10 cp. In some embodiments of the present invention, a freshening composition has a dynamic viscosity of less than about 15 cp. In some embodiments of the present invention, a freshening composition has a dynamic viscosity of less than about 20 cp. In some embodiments of the present invention, a freshening composition has a dynamic viscosity of less than about 25 cp. In some embodiments of the present invention, a freshening composition has a dynamic viscosity of less than about 30 cp. In some embodiments of the present invention, a freshening composition has a dynamic viscosity of less than about 35 cp. In some embodiments of the present invention, a freshening composition has a dynamic viscosity of less than about 40 cp. In some embodiments of the present invention, a freshening composition has a dynamic viscosity of less than about 45 cp. In some embodiments of the present invention, a freshening composition has a dynamic viscosity of less than about 50 cp. In some embodiments of the present invention, a freshening composition has a dynamic viscosity of less than about 60 cp. In some embodiments of the present invention, a freshening composition has a dynamic viscosity of less than about 70 cp. In some embodiments of the present invention, a freshening composition has a dynamic viscosity of less than about 80 cp. In some embodiments of the present invention, a freshening composition has a dynamic viscosity of less than about 90 cp. In some embodiments of the present invention, a freshening composition has a dynamic viscosity of less than about 100 cp.

A preferred freshening composition of the present invention has a surface density in the range from about 650 g/l to about 1,300 g/l. Another preferred freshening composition of the present invention has a surface density in the range from about 700 g/l to about 1,300 g/l. Another preferred freshening composition of the present invention has a surface density in the range of between 650 g/l and about 1,300 g/l. Another preferred freshening composition of the present invention has a surface density in the range of between about 700 g/l and about 1,300 g/l.

A preferred freshening composition of the present invention has a flash point higher than about 140° F., a surface tension from about 10 mN/m to about 40 mN/m. a dynamic viscosity from about 1 cp to about 20 cp, and a density in the range from about 700 g/l to about 1,200 g/l. Another preferred freshening composition of the present invention has a flash point higher than about 140° F., a surface tension in the range of between 10 mN/m and about 40 mN/m. a dynamic viscosity in the range of between about 1 cp and about 20 cp, and a density in the range of between about 700 g/l and about 1,200 g/l.

A preferred freshening composition of the present invention has a vapor pressure of less than about 0.1 atm.

Preferred freshening compositions of the present invention comply with VOC, CARB and safety-toxicity requirements by having a flash point higher than about 140° F. and being substantially free of volatile organic compounds ("VOCs"), i.e., they contain no more than about 18 wt % VOCs.

The freshening compositions of the present invention may be used with or without an air care product or with or without a device as further described herein.

The freshening compositions of the present invention may be combined with any air care freshening product wherein the freshening composition may be used directly or after dilution with solvents or diluents.

A. Perfume Raw Materials

In some embodiments of the present invention, a freshening composition comprises a perfume raw material. It is understood and one of ordinary skill in the art will appreciate that, if not clearly contradicted by the content of this specification, each embodiment of a perfume raw material and/or features/elements disclosed as part of that embodiment can be combined with any of the embodiments hereinabove or hereinbelow.

In some embodiments of the present invention, an air freshening composition comprises a perfume raw material. In some embodiments of the present invention, a liquid freshening composition comprises a perfume raw material. In some embodiments of the present invention, a clear freshening composition comprises a perfume raw material. In some embodiments of the present invention, a homogenous freshening composition comprises a perfume raw material. In some embodiments of the present invention, a clear liquid freshening composition comprises a perfume raw material. In some embodiments of the present invention, a liquid air freshening composition comprises a perfume raw material. In some embodiments of the present invention, a homogeneous clear liquid air freshening composition comprises a perfume raw material. In some embodiments of the present invention, a homogeneous clear liquid air freshening composition comprises a perfume raw material.

In some embodiments of the present invention, a freshening composition comprises a perfume raw material and a solvent or diluent. In some embodiments of the present invention, an air freshening composition comprises a perfume raw material and a solvent or diluent. In some embodiments of the present invention, a liquid freshening composition comprises a perfume raw material and a solvent or diluent. In some embodiments of the present invention, a clear freshening composition comprises a perfume raw material and a solvent or diluent. In some embodiments of the present invention, a homogenous freshening composition comprises a perfume raw material and a solvent or diluent. In some embodiments of the present invention, a clear liquid freshening composition comprises a perfume raw material and a solvent or diluent. In some embodiments of the present invention, a liquid air freshening composition comprises a perfume raw material and a solvent or diluent. In some embodiments of the present invention, a homogeneous clear liquid air freshening composition comprises a perfume raw material and a solvent or diluent. In some embodiments of the present invention, a homogeneous clear liquid air freshening composition comprises a perfume raw material and a solvent or diluent.

In some embodiments of the present invention, a freshening composition comprises a perfume raw material and a fragrance release modulator. In some embodiments of the present invention, an air freshening composition comprises a perfume raw material and a fragrance release modulator. In some embodiments of the present invention, a liquid freshening composition comprises a perfume raw material and a fragrance release modulator. In some embodiments of the present invention, a clear freshening composition comprises a perfume raw material and a fragrance release modulator. In some embodiments of the present invention, a homogenous freshening composition comprises a perfume raw material and a fragrance release modulator. In some embodiments of the present invention, a clear liquid freshening composition comprises a perfume raw material and a fragrance release modulator. In some embodiments of the present invention, a liquid air freshening composition comprises a perfume raw material and a fragrance release modulator. In some embodiments of the present invention, a homogeneous clear liquid air freshening composition comprises a perfume raw material and a fragrance release modulator. In some embodiments of the present invention, a homogeneous clear liquid air freshening composition comprises a perfume raw material and a fragrance release modulator.

In some embodiments of the present invention, a freshening composition comprises a perfume raw material, a solvent or diluent, and a fragrance release modulator. In some embodiments of the present invention, an air freshening composition comprises a perfume raw material, a solvent or diluent, and a fragrance release modulator. In some embodiments of the present invention, a liquid freshening composition comprises a perfume raw material, a solvent or diluent, and a fragrance release modulator. In some embodiments of the present invention, a clear freshening composition comprises a perfume raw material, a solvent or diluent, and a fragrance release modulator. In some embodiments of the present invention, a homogenous freshening composition comprises a perfume raw material, a solvent or diluent, and a fragrance release modulator. In some embodiments of the present invention, a clear liquid freshening composition comprises a perfume raw material, a solvent or diluent, and a fragrance release modulator. In some embodiments of the present invention, a liquid air freshening composition comprises a perfume raw material, a solvent or diluent, and a fragrance release modulator. In some embodiments of the present invention, a homogeneous clear liquid air freshening composition comprises a perfume raw material, a solvent or diluent, and a fragrance release modulator. In some embodiments of the present invention, a homogeneous clear liquid air freshening composition comprises a perfume raw material, a solvent or diluent, and a fragrance release modulator.

In some embodiments of the present invention, a perfume raw material comprises one or more ingredients. Perfume raw materials comprise a variety of compounds and, e.g., include compounds referred to as a fragrance ingredient, a flavor ingredient, an essential oil, and a natural extract. A fragrance ingredient, as used herein, refers to any perfume raw material that is utilized for its fragrance, scent and/or hedonic benefit.

Thus, a freshening composition of this invention may include various, different PRMs. A freshening composition of this invention may include a plurality of PRMs. These PRMs are not particularly limited as far as their use as part of a freshening composition is concerned. Exemplary perfume raw materials are disclosed herein and have been disclosed elsewhere, e.g., in U.S. Pat. Nos. 5,663,134; 5,670,475; 5,783,544; 5,939,060; and 6,146,621, each of which is incorporated herewith by reference. Other known synthetic aroma chemicals and natural origin fragrance material that may be used as a PRM are described in "Perfume and Flavor Chemicals", Vols. I and II, Steffen Arctander, Allured Pub. Co. (1994); "Perfumery Material Performance V.3.3", Boelens Aroma Chemical Information Service (1996); and "Flower Oils and Floral Compounds In Perfumery", Danute Lajaujis Anonis, Allured Pub. Co. (1993), each of which is incorporated herewith by reference.

Perfume raw materials described herein may be characterized by their volatility and fall into three categories: highly volatile (top not), medium volatile (medium not), and low volatile (bottom not).

Any perfume raw material or any blend of a plurality of perfume raw materials that can be smelled is also referred to herein as a perfume or a fragrance. Specific fragrances that are described in great detail herein, include, but are not limited to, Apple Fragrance and Floral Fresh Fragrance, each of which comprises a blend of a plurality of perfume raw materials. Acetic acid, on the other hand is a non-limiting of a single ingredient that has a smell and hence, may also be referred to as a perfume or fragrance. Blending, mixing, combining a plurality of perfume raw materials allows the practitioner to create various and different smells.

In some embodiments of the present invention, a perfume raw material comprises an ingredient selected from the group consisting of an ester, an alcohol, an aldehyde, a ketone, an acetal, a phenol, an ether, a lactone, a furan, a hydrocarbon, an acid, a natural origin fragrance material, a stereoisomer of any preceeding perfume raw material, and a mixture of any of the preceeding perfume raw materials.

In some embodiments of the present invention, a perfume raw material comprises an ester. A variety of esters may be used without diverging from the scope of the present invention. In some embodiments of the present invention, a perfume raw material is an ester selected from the group consisting of an acrylic ester (methyl, ethyl, etc.), an acetoacetic ester (methyl, ethyl, etc.), an anisic ester (methyl, ethyl, etc.), a benzoic ester (allyl, isoamyl, ethyl, geranyl, linalyl, phenylethyl, hexyl, cis-3-hexenyl, benzyl, methyl, etc.), an anthranilic ester (cinnamyl, cis-3-hexenyl, methyl, ethyl, linalyl, isobutyl, etc.), an N-methylanthranilic ester (methyl, ethyl etc.), an isovaleric ester (amyl, allyl, isoamyl, isobutyl, isopropyl, ethyl, octyl, geranyl, cyclohexyl, citronellyl, terpenyl, linalyl, cinnamyl, phenylethyl, butyl, propyl, hexyl, benzyl, methyl, rhodinyl, etc.), an isobutyric ester (isoamyl, geranyl, citronellyl, terpenyl, cinnamyl, octyl, neryl, phenylethyl, phenylpropyl, phenoxyethyl, butyl, propyl, isopropyl, hexyl, benzyl, methyl, ethyl, linalyl, rhodinyl, etc.), an undecylenic ester (allyl, isoamyl, butyl, ethyl, methyl, etc.), an octanoic ester (allyl, isoamyl, ethyl, octyl, hexyl, butyl, methyl, linalyl, etc.), an octenoic ester (methyl, ethyl, etc.), an octyne carboxylic ester (methyl, ethyl, etc.), a caproic ester (allyl, amyl, isoamyl, methyl, ethyl, isobutyl, propyl, hexyl, cis-3-hexenyl, trans- 2-hexenyl, linalyl, geranyl, cyclohexyl, etc.), a hexenoic ester (methyl, ethyl, etc.), a valeric ester (amyl, isopropyl, isobutyl, ethyl, cis-3-hexenyl, trans-2-hexenyl, cinnamyl, phenylethyl, methyl, etc.), a formic ester (anisyl, isoamyl, isopropyl, ethyl, octyl, geranyl, citronellyl, cinnamyl, cyclohexyl, terpenyl, phenylethyl, butyl, propyl, hexyl, cis-3-hexenyl, benzyl, linalyl, rhodinyl, etc.), a crotonic ester (isobutyl, ethyl, cyclohexyl, etc.), a cinnamic ester (allyl, ethyl, methyl, isopropyl, propyl, 3-phenylpropyl, benzyl, cyclohexyl, methyl, etc.), a succinic ester (mono-methyl, diethyl, dimethyl, etc.), an acetic ester (anisyl, amyl, alpha-amylcinnamyl, isoamyl, isobutyl, isopropyl, isobornyl, isoeugenyl, eugenyl, 2-ethylbutyl, ethyl, 3-octyl, p-cresyl, o-cresyl, geranyl, α-santalyl, β-santalyl, cyclohexyl, cyclonreryl, dihydrocuminyl, dimethylbenzylcarbinyl, cinnamyl, styrallyl, decyl, dodecyl, terpenyl, guanyl, neryl, nonyl, phenylethyl, phenylpropyl, butyl, furfuryl, propyl, hexyl, cis-3-hexenyl, trans-2-hexenyl, cis-3-nonenyl, cis-6-nonenyl, cis-3, cis-6-nonadienyl, 3-methyl-2-butenyl, heptyl, benzyl, borayl, myrcenyl, dihydromyrcenyl, myrtenyl, methyl, 2-methylbutyl, menthyl, linalyl, rhodinyl, etc.), an salicylic ester (allyl, isoamyl, phenyl, phenylethyl, benzyl, ethyl, methyl, etc.), a cyclohexyl alkanoic ester (ethyl cyclohexyl acetate, allyl cyclohexyl propionate, allyl cyclohexyl butyrate, allyl cyclohexyl hexanoate, allyl cyclohexyl decanoate, allyl cyclohexyl valerate, etc.), a stearic ester (ethyl, propyl, butyl, etc.), a sebacic ester (diethyl, dimethyl, etc.), a decanoic ester (isoamyl, ethyl, butyl, methyl, etc.), a dodecanoic ester (isoamyl, ethyl, butyl, etc.), a lactic ester (isoamyl, ethyl, butyl, etc.), a nonanoic ester (ethyl, phenylethyl, methyl, etc.), a nonenoic ester (allyl, ethyl, methyl, etc.), a hydroxyhexanoic ester (ethyl, methyl, etc.), a phenylacetic ester (isoamyl, isobutyl, ethyl, geranyl, citronellyl, cis-3-hexenyl, methyl, etc.), a phenoxyacetic ester (allyl, ethyl, methyl, etc.), a furancarboxylic ester (ethyl furancarboxylate, methyl furancarboxylate, hexyl furancarboxylate, isobutyl furanpropionate, etc.), a propionic ester (anisyl, allyl, ethyl, amyl, isoamyl, propyl, butyl, isobutyl, isopropyl, benzyl, geranyl, cyclohexyl, citronellyl, cinnamyl, tetrahydrofurfuryl, tricyclodecenyl, heptyl, bornyl, methyl, menthyl, linalyl, terpenyl, a-methylpropionyl, β-methylpropionyl, etc.), a heptanoic ester (allyl, ethyl, octyl, propyl, methyl, etc.), a heptin carboxylic ester (allyl, ethyl, propyl, methyl, etc.), a myristic ester (isopropyl, ethyl, methyl etc.), a phenylglycidic ester (ethyl phenyl glycidate, ethyl 3-methylphenylglycidate, ethyl p-methyl-P-phenylglycidate, etc.), 2-methylbutyric ester (methyl, ethyl, octyl, phenylethyl, butyl, hexyl, benzyl, etc.), 3-methylbutyric ester (methyl, ethyl, etc.), a butyric ester (anisyl, amyl, allyl, isoamyl, methyl, ethyl, propyl, octyl, guanyl, linalyl, geranyl, cyclohexyl, citronellyl, cinnamyl, neryl, terpenyl, phenylpropyl, β-phenylethyl, butyl, hexyl, cis-3-hexenyl, trans-2-hexenyl, benzyl, rhodinyl, etc.), and a hydroxybutyric ester (methyl, ethyl, menthyl and the like of 3-hydroxybutyrate), a stereoisomer of any preceeding ester, and a mixture of any of the preceeding esters.

In some embodiments of the present invention, a perfume raw material comprises an alcohol. A variety of alcohols may be used without diverging from the scope of the present invention. In some embodiments of the present invention, a perfume raw material is an alcohol selected from the group consisting of an aliphatic alcohol (isoamyl alcohol, 2-ethylhexanol, 1-octanol, 3-octanol, 1-octen-3-ol, 1-decanol, 1-dodecanol, 2,6-nonadienol, nonanol, 2-nonanol, cis-3, nonenol, trans-2, cis-6-nonadienol, cis-3, cis-6-nonadienol, butanol, hexanol, cis-3-hexenol, trans-2-hexenol, 1-undecanol, heptanol, 2-heptanol, 3-methyl-1-pentanol, etc.), a terpene alcohol (borneol, isoborneol, carveol, geraniol, α-santalol, β-santalol, citronellol, 4-thujanol, terpineol, 4-terpineol, nerol, myrcenol, myrtenol, dihydromyrcenol, tetrahydromyrcenol, nerolidol, hydroxycitronerol, farnesol, perilla alcohol, rhodinol, linalool, etc.), an aromatic alcohol (anise alcohol, alpha-amylcinnamic alcohol, isopropylbenzylcarbinol, carvacrol, cumin alcohol, dimethylbenzylcarbinol, cinnamic alcohol, α-phenylethyl alcohol, phenylethylcarbinol, β-phenylethyl alcohol, 3-phenylpropyl alcohol, benzyl alcohol, etc.), a stereoisomer of any preceeding alcohol, and a mixture of any of the preceeding alcohols.

In some embodiments of the present invention, a perfume raw material comprises an aldehyde. A variety of aldehydes may be used without diverging from the scope of the present invention. In some embodiments of the present invention, a perfume raw material is an aldehyde selected from the group consisting of an aliphatic aldehyde (acetoaldehyde, octanal, nonanal, decanal, undecanal, 2,6-dimethyl-5-heptanal, 3,5,5-trimethylhexanal, cis-3, cis-6-nonadienal, trans-2, cis-6-nonadienal, valeraldehyde, propanal, isopropanal, hexanal, trans-2-hexenal, cis-3-hexenal, 2-pentenal, dodecanal, tetradecanal, trans-4-decenal, trans-2-tridecenal, trans-2-dodecenal, trans-2-undecenal, 2,4-hexadienal, cis-6-nonenal, trans-2-nonenal, 2-methylbutanal, etc.), an aromatic aldehyde (anisaldehyde, α-amylcinnamic aldehyde, α-methylcinnamic aldehyde, cyclamen aldehyde, p-isopropylphenylacetaldehyde, ethylvanillin, cuminaldehyde, salicylaldehyde, cinnamic aldehyde, o-tolylaldehyde, m-tolylaldehyde, p-tolylaldehyde, vanillin, piperonal, phenylacetaldehyde, heliotropin, benzaldehyde, 4-methyl-2-phenyl-2-pentenal, p-methoxycinnamic aldehyde, p-methoxybenzaldehyde, etc.), a terpene aldehyde (geranial, citral, citronellal, α-sinensal, β-sinensal, perillaldehyde, hydroxycitronellal, tetrahydrocitral, myrtenal, cyclocitral, isocyclocitral, citronelly-loxyacetaldehyde, neral, methylenecitronellal, myrac aldehyde, vernaldehyde, safranal, etc.), a stereoisomer of any preceeding aldehyde, and a mixture of any of the preceeding aldehydes.

In some embodiments of the present invention, a perfume raw material comprises a ketone. A variety of ketones may be used without diverging from the scope of the present invention. In some embodiments of the present invention, a perfume raw material is a ketone selected from the group consisting of a cyclic ketone (1-acetyl-3,3-dimethyl-1-cyclohexene, cis-jasmone, α-irone, β-irone, γ-irone, ethylmaltol, cyclotene, dihydronootkatone, 3,4-dimethyl-1,2-cyclopentadione, sotolone, α-damascone, 3-damascone, γ-damascene, 6-damascone, α-damascenone, β-damascenone, γ-damascenone, nootkatone, 2-sec-butylcyclohexanone, maltol, α-ionone, β-ionone, γ-ionone, α-methylionone, β-methylionone, γ-methylionone, α-isomethylionone, β-isomethylionone, γ-isomethylionone, furaneol, camphor, etc.), an aromatic ketone (acetonaphthone, acetophenone, anisylideneacetone, raspberry ketone, p-methylacetopheneon, anisylacetone, p-methoxyacetophenone, etc.), a linear ketone (diacetyl, 2-nonanone, 2-heptanone, 2,3-heptanedione, 2-pentanone, methyl amyl ketone, methyl nonyl ketone, β-methyl naphthyl ketone, methylheptanone, 3-heptanone, 4-heptanone, 3-octanone, 2,3-hexanedione, 2-undecanone, dimethyloctenone, 6-methyl-5-hepten-2-one, etc.), a stereoisomer of any preceeding ketone, and a mixture of any of the preceeding ketones.

In some embodiments of the present invention, a perfume raw material comprises an acetal. A variety of acetals may be used without diverging from the scope of the present invention. In some embodiments of the present invention, a perfume raw material is an acetal selected from the group consisting of acetaldehyde diethyl acetal, acetaldehyde diamyl acetal, acetaldehyde dihexyl acetal, acetaldehyde propylene glycol acetal, acetaldehyde ethyl cis-3-hexenyl acetal, benzaldehyde glycerin acetal, benzaldehyde propylene glycol acetal, citral dimethyl acetal, citral diethyl acetal, citral propylene glycol acetal, citral ethylene glycol acetal, phenyl acetaldehyde dimethyl acetal, citronellyl methyl acetal, acetaldehyde phenylethyl propyl acetal, hexanal dimethyl acetal, hexanal dihexyl acetal, hexanal propylene glycol acetal, trans-2-hexenal diethyl acetal, trans-2-hexenal propylene glycol acetal, cis-3-hexenal diethyl acetal, heptanal diethyl acetal, heptanal ethylene glycol acetal, octanal dimethyl acetal, nonanal dimethyl acetal, decanal dimethyl acetal, decanal diethyl acetal, 2-methylundecanal dimethyl acetal, citronellal dimethyl acetal, ambersage (from Givaudan Flavors Corporation, East Hanover, N.J., USA), acetoacetate ethyl ethylene glycol acetal, 2-phenylpropanal dimethyl acetal, a stereoisomer of any preceeding acetal, and a mixture of any of the preceeding acetals.

In some embodiments of the present invention, a perfume raw material comprises a phenol. A variety of phenols may be used without diverging from the scope of the present invention. In some embodiments of the present invention, a perfume raw material is a phenol selected from the group consisting of eugenol, isoeugenol, 2-methoxy-4-vinylphenol, thymol, carvacrol, guaiacol, chavicol, a stereoisomer of any preceeding phenol, and a mixture of any of the preceeding phenols.

In some embodiments of the present invention, a perfume raw material comprises an ether. A variety of ethers may be used without diverging from the scope of the present invention. In some embodiments of the present invention, a perfume raw material is an ether selected from the group consisting of anethole, 1,4-cineole, dibenzyl ether, linalool oxide, limonene oxide, nerol oxide, rose oxide, methylisoeugenol, methyl chavicol, isoamyl phenylethyl ether, β-naphthyl methyl ether, phenyl propyl ether, p-cresyl methyl ether, vanillyl butyl ether, alpha-terpinyl methyl ether, citronellyl ethyl ether, geranyl ethyl ether, rose furan, decyl methyl ether, methyl phenylmethyl ether, a stereoisomer of any preceeding ether, and a mixture of any of the preceeding ethers.

In some embodiments of the present invention, a perfume raw material comprises a lactone. A variety of lactones may be used without diverging from the scope of the present invention. In some embodiments of the present invention, a perfume raw material is a lactone selected from the group consisting of γ-decalactone, δ-decalactone, γ-heptalactone, γ-nonalactone, γ-hexalactone, δ-hexalactone, γ-octalactone, δ-octalactone, γ-undecalactone, δ-undecalactone, δ-dodecalactone, δ-2-decenolactone, methyllactone, 5-hydroxy-8-undecenoic acid δ-lactone, jasmine lactone, menthalactone, dihydrocoumarin, octahydrocoumarin, δ-methylcoumarin, a stereoisomer of any preceeding lactone, and a mixture of any of the preceeding lactones.

In some embodiments of the present invention, a perfume raw material comprises a furan. A variety of furans may be used without diverging from the scope of the present invention. In some embodiments of the present invention, a perfume raw material is a furan selected from the group consisting of furan, 2-methyl furan, 2-ethylfuran, 2,5-diethyltetrahydrofuran, 3-hydroxy-2-methyltetrahydrofuran, 2-(methoxymethyl) furan, 2,3-dihydrofuran, furfural, 5-methylfurfural, 3-(2-furyl)-2-methyl-2-propenal, 5-(hydroxymethyl) furfural, 2,5-dimethyl-4-hydroxy-3 (2H)-furanone (furaneol), 4,5-dimethyl-3-hydroxy-2(5H)-furanone (sotolone), 2-ethyl-4-hydroxy-5-methyl-3(2H)-furanone (homofuraneol), 5-ethyl-3-hydroxy-4-methyl-2(5H)furanone (homosotolone), 3-methyl-1,2-cyclopentanedione (cyclotene), 2(5H)-furanone, 4-methyl-2(5H)-furanone, 5-methyl-2(5H)-furanone, 2-methyl-3 (2H)-furanone, 5-methyl-3(2H)-furanone, 2-acetylfuranone, 2-acetyl-5-methylfuran, furfuryl alcohol, methyl 2-furancarboxylate, ethyl 2-furancarboxylate, furfuryl acetate, a stereoisomer of any preceeding furan, and a mixture of any of the preceeding furans.

In some embodiments of the present invention, a perfume raw material comprises a hydrocarbon. A variety of hydrocarbons may be used without diverging from the scope of the present invention. In some embodiments of the present invention, a perfume raw material is a hydrocarbon selected from the group consisting of α-bisabolene, β-bisabolene, β-caryophyllene, p-cymene, terpinene, terpinolene, cadinene, farnesene, limonene, ocimene, myrcene, α-pinene, β-pinene, 1,3,5-undecatriene, valencene, a stereoisomer of any preceeding hydrocarbon, and a mixture of any of the preceeding hydrocarbons.

In some embodiments of the present invention, a perfume raw material comprises an acid. A variety of acids may be used without diverging from the scope of the present invention. In some embodiments of the present invention, a perfume raw material is an acid selected from the group consisting of geranic acid, dodecanoic acid, myristic acid, stearic acid, lactic acid, phenylacetic acid, pyruvic acid, trans-2-methyl-2-pentenoic acid, 2-methyl-cis-3-pentenoic acid, 2-methyl-4-pentenoic acid, cyclohexanecarboxylic acid, a stereoisomer of any preceeding acid, and a mixture of any of the preceeding acids.

In some embodiments of the present invention, a perfume raw material comprises a natural origin fragrance compound. A variety of natural origin fragrance compounds may be used without diverging from the scope of the present invention. In some embodiments of the present invention, a perfume raw material is a natural origin fragrance compound isolated or purified from a natural origin selected from the group consisting of anise, orange, lemon, lime, mandarin, petit grain, bergamot, lemon balm, grapefruit, elemi, olibanum, lemon grass, neroli, marjoram, angelica root, star anise, basil, bay, calamus, chamomile, caraway, cardamon, cassia, cinnamon, pepper, perilla, cypress, oregano, cascarilla, ginger, parsley, pine needle, sage, hyssop, tea tree, mustard, horseradish, clarisage, clove, cognac, coriander, estragon, eucalyptus, fennel, guaiac wood, dill, cajuput, worm seed, pimento, juniper, fenugreek, garlic, laurel, mace, mil, nutmeg, spruce, geranium, citronella, lavender, lavandin, palmarosa, rose, rosemary, sandalwood, oak moth, cider wood, vetiver, linaloe, bois de rose, patchouli, labdanum, cumin, thyme, ylang-ylang, birch, capsicum, celery, tolu balsam, djenne, inmortel, benzoin, jasmine, cassia, tuberose, mignonette, marigold, mimosa, opopanax, orris, vanilla, licorice, and a mixture of any of the preceeding perfume raw materials.

In some embodiments of the present invention, a perfume raw material comprises one or more compounds selected from the group of compounds listed in Table 1 of published U.S. Pat. Appl. No. 2018/0008740 A1.

In some embodiments of the present invention, perfume raw materials, perfumes or fragrances, when too concentrated are being combined with a solvent or diluent (as described herein). As not all perfume raw materials are liquid, combining them with a solvent or diluent will also solve solid raw perfume ingredients, In some embodiments of the present invention, perfume raw materials, perfumes or fragrances in concentrated or diluted form are being combined with a fragrance release modulator (as described herein), which will allow the modulation of the releasing rate, or the modulation of the dispersing pattern of the respective freshening composition.

The amount of perfume raw material in a freshening composition of the present invention may vary depending on the type of perfume raw material being used. Generally, the amount of perfume raw material in a freshening composition of the present invention ranges from about 0.001 wt % to about 90 wt %. When the amount of the perfume raw materials too low, fragrance intensity may not be sufficient. When the amount of the perfume raw materials too high, the cost of the freshening composition may become unattractive for a consumer. Taking these points into account, one of skill in the art will appreciate that it is desirable that the amount of a perfume raw material is appropriately selected depending on the type of perfume raw material being used. Using guidance provided herein, one of ordinary skill in the art will be able to determine an appropriate amount of a perfume raw material to be used when formulating a freshening composition.

The amount of perfume raw material, such as a fragrance ingredient, added to formulate a freshening composition of the present invention may vary. In some embodiments of the present invention, a freshening composition comprises greater than about 0.001 wt % of a perfume raw material. In some embodiments of the present invention, a freshening composition comprises greater than about 0.005 wt % of a perfume raw material. In some embodiments of the present invention, a freshening composition comprises greater than about 0.01 wt % of a perfume raw material. In some embodiments of the present invention, a freshening composition comprises greater than about 0.02 wt % of a perfume raw material. In some embodiments of the present invention, a freshening composition comprises greater than about 0.03 wt % of a perfume raw material. In some embodiments of the present invention, a freshening composition comprises greater than about 0.04 wt % of a perfume raw material. In some embodiments of the present invention, a freshening composition comprises greater than about 0.05 wt % of a perfume raw material. In some embodiments of the present invention, a freshening composition comprises greater than about 0.06 wt % of a perfume raw material. In some embodiments of the present invention, a freshening composition comprises greater than about 0.07 wt % of a perfume raw material. In some embodiments of the present invention, a freshening composition comprises greater than about 0.08 wt % of a perfume raw material. In some embodiments of the present invention, a freshening composition comprises greater than about 0.09 wt % of a perfume raw material. In some embodiments of the present invention, a freshening composition comprises greater than about 0.1 wt % of a perfume raw material. In some embodiments of the present invention, a freshening composition comprises greater than about 0.2 wt % of a perfume raw material. In some embodiments of the present invention, a freshening composition comprises greater than about 0.3 wt % of a perfume raw material. In some embodiments of the present invention, a freshening composition comprises greater than about 0.4 wt % of a perfume raw material. In some embodiments of the present invention, a freshening composition comprises greater than about 0.5 wt % of a perfume raw material. In some embodiments of the present invention, a freshening composition comprises greater than about 1 wt % of a perfume raw material. In some embodiments of the present invention, a freshening composition comprises greater than about 2 wt % of a perfume raw material. In some embodiments of the present invention, a freshening composition comprises greater than about 3 wt % of a perfume raw material. In some embodiments of the present invention, a freshening composition comprises greater than about 4 wt % of a perfume raw material. In some embodiments of the present invention, a freshening composition comprises greater than about 5 wt % of a perfume raw material. In some embodiments of the present invention, a freshening composition comprises greater than about 6 wt % of a perfume raw material. In some embodiments of the present invention, a freshening composition comprises greater than about 7 wt % of a perfume raw material. In some embodiments of the present invention, a freshening composition comprises greater than about 8 wt % of a perfume raw material. In some embodiments of the present invention, a freshening composition comprises greater than about 9 wt % of a perfume raw material. In some embodiments of the present invention, a freshening composition comprises greater than about 10 wt % of a perfume raw material. In some embodiments of the present invention, a freshening composition comprises greater than about 15 wt % of a perfume raw material. In some embodiments of the present invention, a freshening composition comprises greater than about 20 wt % of a perfume raw material. In some embodiments of the present invention, a freshening composition comprises greater than about 25 wt % of a perfume raw material. In some embodiments of the present invention, a freshening composition comprises greater than about 30 wt % of a perfume raw material. In some embodiments of the present invention, a freshening composition comprises greater than about 40 wt % of a perfume raw material. In some embodiments of the present invention, a freshening composition comprises greater than about 50 wt % of a perfume raw material. In some embodiments of the present invention, a freshening composition comprises greater than about 60 wt % of a perfume raw material. In some embodiments of the present invention, a freshening composition comprises greater than about 70 wt % of a perfume raw material. In some embodiments of the present invention, a freshening composition comprises greater than about 80 wt % of a perfume raw material. In some embodiments of the present invention, a freshening composition comprises greater than about 85 wt % of a perfume raw material. Wt % is based on the total weight of the freshening composition.

In some embodiments of the present invention, a freshening composition comprises less than about 0.001 wt % of a perfume raw material. In some embodiments of the present invention, a freshening composition comprises less than about 0.005 wt % of a perfume raw material. In some embodiments of the present invention, a freshening composition comprises less than about 0.01 wt % of a perfume raw material. In some embodiments of the present invention, a freshening composition comprises less than about 0.02 wt % of a perfume raw material. In some embodiments of the present invention, a freshening composition comprises less than about 0.03 wt % of a perfume raw material. In some embodiments of the present invention, a freshening composition comprises less than about 0.04 wt % of a perfume raw material. In some embodiments of the present invention, a freshening composition comprises less than about 0.05 wt % of a perfume raw material. In some embodiments of the present invention, a freshening composition comprises less than about 0.06 wt % of a perfume raw material. In some embodiments of the present invention, a freshening composition comprises less than about 0.07 wt % of a perfume raw material. In some embodiments of the present invention, a freshening composition comprises less than about 0.08 wt % of a perfume raw material. In some embodiments of the present invention, a freshening composition comprises less than about 0.09 wt % of a perfume raw material. In some embodiments of the present invention, a freshening composition comprises less than about 0.1 wt % of a perfume raw material. In some embodiments of the present invention, a freshening composition comprises less than about 0.2 wt % of a perfume raw material. In some embodiments of the present invention, a freshening composition comprises less than about 0.3 wt % of a perfume raw material. In some embodiments of the present invention, a freshening composition comprises less than about 0.4 wt % of a perfume raw material. In some embodiments of the present invention, a freshening composition comprises less than about 0.5 wt % of a perfume raw material. In some embodiments of the present invention, a freshening composition comprises less than about 0.6 wt % of a perfume raw material. In some embodiments of the present invention, a freshening composition comprises less than about 0.7 wt % of a perfume raw material. In some embodiments of the present invention, a freshening composition comprises less than about 0.8 wt % of a perfume raw material. In some embodiments of the present invention, a freshening composition comprises less than about 0.9 wt % of a perfume raw material. In some embodiments of the present invention, a freshening composition comprises less than about 1 wt % of a perfume raw material. In some embodiments of the present invention, a freshening composition comprises less than about 2 wt % of a perfume raw material. In some embodiments of the present invention, a freshening composition comprises less than about 3 wt % of a perfume raw material. In some embodiments of the present invention, a freshening composition comprises less than about 4 wt % of a perfume raw material. In some embodiments of the present invention, a freshening composition comprises less than about 5 wt % of a perfume raw material. In some embodiments of the present invention, a freshening composition comprises less than about 6 wt % of a perfume raw material. In some embodiments of the present invention, a freshening composition comprises less than about 7 wt % of a perfume raw material. In some embodiments of the present invention, a freshening composition comprises less than about 8 wt % of a perfume raw material. In some embodiments of the present invention, a freshening composition comprises less than about 9 wt % of a perfume raw material. In some embodiments of the present invention, a freshening composition comprises less than about 10 wt % of a perfume raw material. In some embodiments of the present invention, a freshening composition comprises less than about 15 wt % of a perfume raw material. In some embodiments of the present invention, a freshening composition comprises less than about 20 wt % of a perfume raw material. In some embodiments of the present invention, a freshening composition comprises less than about 25 wt % of a perfume raw material. In some embodiments of the present invention, a freshening composition comprises less than about 30 wt % of a perfume raw material. In some embodiments of the present invention, a freshening composition comprises less than about 40 wt % of a perfume raw material. In some embodiments of the present invention, a freshening composition comprises less than about 50 wt % of a perfume raw material. In some embodiments of the present invention, a freshening composition comprises less than about 60 wt % of a perfume raw material. In some embodiments of the present invention, a freshening composition comprises less than about 70 wt % of a perfume raw material. In some embodiments of the present invention, a freshening composition comprises less than about 80 wt % of a perfume raw material. In some embodiments of the present invention, a freshening composition comprises less than about 85 wt % of a perfume raw material. Wt % is based on the total weight of the freshening composition.

In some embodiments of the present invention, a freshening composition comprises a perfume raw material in the range from about 0.001 wt % to about 90 wt %. In some embodiments of the present invention, a freshening composition comprises a perfume raw material in the range from about 0.01 wt % to about 85 wt %. In some embodiments of the present invention, a freshening composition comprises a perfume raw material in the range from about 0.1 wt % to about 85 wt %. In some embodiments of the present invention, a freshening composition comprises a perfume raw material in the range from about 0.2 wt % to about 80 wt %. In some embodiments of the present invention, a freshening composition comprises a perfume raw material in the range from about 0.5 wt % to about 70 wt %. In some embodiments of the present invention, a freshening composition comprises a perfume raw material in the range from about 0.75 wt % to about 65 wt %. In some embodiments of the present invention, a freshening composition comprises a perfume raw material in the range from about 1 wt % to about 60 wt %. In some embodiments of the present invention, a freshening composition comprises a perfume raw material in the range from about 2 wt % to about 55 wt %. In some embodiments of the present invention, a freshening composition comprises a perfume raw material in the range from about 3 wt % to about 50 wt %. In some embodiments of the present invention, a freshening composition comprises a perfume raw material in the range from about 5 wt % to about 45 wt %. In some embodiments of the present invention, a freshening composition comprises a perfume raw material in the range from about 7.5 wt % to about 40 wt %. In some embodiments of the present invention, a freshening composition comprises a perfume raw material in the range from about 10 wt % to about 35 wt %. In some embodiments of the present invention, a freshening composition comprises a perfume raw material in the range from about 15 wt % to about 30 wt %. In some embodiments of the present invention, a freshening composition comprises a perfume raw material in the range from about 20 wt % to about 25 wt %. Wt % is based on the total weight of the freshening composition.

1. Functional Ingredients

In some embodiments of the present invention, a freshening composition comprises a compound having a functional activity, i.e., a functional ingredient. It is understood and one of ordinary skill in the art will appreciate that, if not clearly contradicted by the content of this specification, each embodiment of a compound having a functional activity or a functional ingredient and/or features/elements disclosed as part of that embodiment can be combined with any of the embodiments hereinabove or hereinbelow.

In some embodiments of the present invention, a freshening composition comprises a perfume raw material and a functional ingredient. In some embodiments of the present invention, an air freshening composition comprises a perfume raw material and a functional ingredient. In some embodiments of the present invention, a liquid freshening composition comprises a perfume raw material and a functional ingredient. In some embodiments of the present invention, a clear freshening composition comprises a perfume raw material and a functional ingredient. In some embodiments of the present invention, a homogenous freshening composition comprises a perfume raw material and a functional ingredient. In some embodiments of the present invention, a clear liquid freshening composition comprises a perfume raw material and a functional ingredient. In some embodiments of the present invention, a liquid air freshening composition comprises a perfume raw material and a functional ingredient. In some embodiments of the present invention, a homogeneous clear liquid air freshening composition comprises a perfume raw material and functional ingredient. In some embodiments of the present invention, a homogeneous clear liquid air freshening composition comprises a perfume raw material and a functional ingredient.

Functional ingredients provide various beneficial activities, such as cleaning, surface care protection, fabric conditioning or softening, fabric refreshing, de-wrinkling, air freshening, air deodorizing, malodor removal, skin moisturizing, body deodorizing, and the like. A functional ingredient may include water or deionized water.

A variety of functional ingredients may be used without diverging from the scope of the present invention. In some embodiments of the present invention, an ingredient having a functional activity is selected from the group consisting of an ingredient having malodor counteracting activity, an ingredient having antimicrobial activity, an ingredient having an insect repellant activity, an ingredient having a preservative activity, an ingredient having an antioxidant activity, an ingredient having a humectant activity, an ingredient having a UV-blocking activity, an ingredient having a pigment activity, an ingredient having a dye activity, an ingredient having a surfactant activity, an ingredient having an emulsifier activity, an ingredient having a solubilizer activity, an ingredient having a polymer activity, and an ingredient having a buffer activity.

In some embodiments of the present invention, a functional ingredient is an ingredient having a malodor counteracting activity. Thus, in some embodiments of the present invention, a freshening composition comprises an ingredient having malodor counteracting activity. A variety of ingredients having malodor counteracting activity may be used without diverging from the scope of the present invention.

In a freshening composition of the present invention, certain functional ingredients deliver a malodor removal benefit. A malodor removal benefit is defined as both a sensory and analytically measurable (such as by gas chromatography) malodor reduction or malodor decrease. Thus, in some embodiments of the present invention, a freshening composition delivers a malodor removal benefit. A freshening composition will not function merely by using perfume to cover up or mask odors. Rather, in some embodiments of the present invention wherein a freshening composition is provided with a malodor controlling agent, the freshening composition utilizes one or more of several types of odor control mechanisms. A preferred functional ingredient having malodor controlling agent is cyclodextrin. Cyclodextrin" includes α-cyclodextrin, β-cyclodextrin, γ-cyclodextrin. Included within "cyclodextrin" are derivatives of cyclodextrin, e.g., ether, ester and amide derivatives. In some embodiments of the present invention, β-cyclodextrin is an unmodified β-cyclodextrin. Particularly included within the term "cyclodextrin" are modified cyclodextrins as described in U.S. Pat. Nos. 5,134,127 and 6,407,079. Thus, in some embodiments of the present invention, a freshening composition comprises a cyclodextrin.

In some embodiments of the present invention, a functional ingredient is an ingredient having antimicrobial activity. Thus, in some embodiments of the present invention, a freshening composition comprises an ingredient having antimicrobial activity. An antimicrobial ingredient may also exhibit some bactericidal properties, depending on the dose. The main role of an antimicrobial ingredient is to inhibit the growth of any such microorganism in a freshening composition and on any area which is exposed to such freshening composition.

A variety of ingredients having antimicrobial activity may be used without diverging from the scope of the present invention. Suitable antimicrobial ingredients include, but are not limited to parabens, i.e. methyl, ethyl, propyl or butyl paraben and mixtures thereof; benzyl alcohol; phenol; cresol; cetrimide and thiomersal. A preferred antimicrobial ingredient is a paraben. Other preferred ingredients having microbial activity are hexylene glycol, 1,2 hexanediol, and phenoxy ethanol.

In some embodiments of the present invention, a functional ingredient is an insect repellant. Thus, in some embodiments of the present invention, a freshening composition comprises an insect repellant. A variety of insect repellants may be used without diverging from the scope of the present invention. Preferred insect repellents include, but are not limited to, N,N-diethyl-meta-toluamide and methyl nonyl ketone.

In some embodiments of the present invention, a functional ingredient is preservative. Thus, in some embodiments of the present invention, a freshening composition comprises a preservative. A variety of preservatives may be used without diverging from the scope of the present invention. Preferred preservatives include, but are not limited to, imidazolidinyl urea, diazolidinyl urea, allantoin, and sodium hydroxymethylglycinate.

In some embodiments of the present invention, a functional ingredient is an antioxidant. Thus, in some embodiments of the present invention, a freshening composition comprises an antioxidant. A variety of antioxidants may be used without diverging from the scope of the present invention. Preferred antioxidants include, but are not limited to, butylate hydroxytoluene, ascorbic acid, and tocopherol.

In some embodiments of the present invention, a functional ingredient is a humectant. Thus, in some embodiments of the present invention, a freshening composition comprises a humectant. A variety of humectants may be used without diverging from the scope of the present invention. Preferred humectants include, but are not limited to, glycerol, hexylene glycol, and ethyl-hexylglycerin.

In some embodiments of the present invention, a functional ingredient is a UV-blocking agent. Thus, in some embodiments of the present invention, a freshening composition comprises a UV-blocking agent. A variety of UV-blocking agents may be used without diverging from the scope of the present invention. Preferred antioxidants include, but are not limited to, avobenzone, oxybenzone, dioxybenzone, and octocrylene.

In some embodiments of the present invention, a functional ingredient is a pigment. Thus, in some embodiments of the present invention, a freshening composition comprises a pigment. A variety of pigments may be used without diverging from the scope of the present invention. Preferred pigments include, but are not limited to, chrome oxide, iron oxide, and ferric ferrocyanate.

In some embodiments of the present invention, a functional ingredient is a dye. Thus, in some embodiments of the present invention, a freshening composition comprises a dye. A variety of dyes may be used without diverging from the scope of the present invention. Such dyes include both water and oil soluable dyes. Preferred dyes include, but are not limited to, C71100 D&C Yellow #8, C73005 D&C Red #6, and C76002 D&C Green #6.

In some embodiments of the present invention, a functional ingredient is a surfactant. Thus, in some embodiments of the present invention, a freshening composition comprises a surfactant. A variety of surfactants may be used without diverging from the scope of the present invention. Surfactants include nonionic surfactants, anionic surfactants, and cationic surfactants. A preferred nonionic surfactant includes, but is not limited to, polyalkoxylate, glucose, sucrose, and amine oxide. A preferred anionic surfactant includes, but is not limited to, sulfate, sulfonate, carboxylate, and phosphate. Preferred cationic surfactant include, but are not limited to, alkylammonium salts.

In some embodiments of the present invention, a functional ingredient is an emulsifier. Thus, in some embodiments of the present invention, a freshening composition comprises an emulsifier. A variety of emulsifiers may be used without diverging from the scope of the present invention. Preferred emulsifiers include, but are not limited to, ethoxylated sorbitols, such as Tween20® or Tween85®. Tween20® is known in the art as polyethylene glycol sorbitan monolaureate (polyoxyethtlenesorbitan monolaureate, CAS Number. 9005-64-5; MDL number MFCD00165986). Tween85® is known in the art as polyoxyethylensorbitan trioleate (CAS Number 9005-70-3; MDL number MFCD01779641).

In some embodiments of the present invention, a functional ingredient is a solubilizer. Thus, in some embodiments of the present invention, a freshening composition comprises a solubilizer. A variety of solubilizers may be used without diverging from the scope of the present invention. Preferred solubilizers include, but are not limited to, propylene glycol, dipropylene glycol, and hexylene glycol.

In some embodiments of the present invention, a functional ingredient is a polymer. Thus, in some embodiments of the present invention, a freshening composition comprises a polymer. A variety of polymers may be used without diverging from the scope of the present invention. Preferred polymers include, but are not limited to, cellulose derivatives, such as ethyl cellulose, and polyvinyl alcohol.

In some embodiments of the present invention, a functional ingredient is a buffer. Thus, in some embodiments of the present invention, a freshening composition comprises a buffer. A variety of buffers may be used without diverging from the scope of the present invention. Preferred buffers include, but are not limited to, phosphate buffers.

In some embodiments of the present invention, a perfume raw material comprises a mixture comprising one or more of an ingredient having a functional activity, as described herein. In some embodiments of the present invention the ingredient having a functional activity is selected from the group consisting of an ingredient having malodor counteracting activity, an ingredient having antimicrobial activity, an insect repellant, a preservative, an antioxidant, a humectant, a UV-blocking agent, a pigment, a dye, a surfactant, an emulsifier, a solubilizer, a polymer, and a buffer.

A freshening composition of the present invention may comprise a functional ingredient at a level of less than about 90 wt %, less than about 85 wt %, less than about 80 wt %, less than about 75 wt %, less than about 70 wt %, less than about 65 wt %, less than about 60 wt %, less than about 55 wt %, less than about 50 wt %, less than about 45 wt %, less than about 40 wt %, less than about 35 wt %, less than about 30 wt %, less than about 25 wt %, less than about 20 wt %, less than about 15 wt %, less than about 10 wt %, less than about 5 wt %, less than about 2 wt %, less than about 1 wt %, less than about 0.5 wt %, less than about 0.2 wt %, or less than about 0.1 wt %, with the weight percentages being relative to the total weight of the freshening composition.

A freshening composition of the present invention may comprise a functional ingredient at a level of greater than about 0.01 wt %, greater than about 0.1 wt %, greater than about 0.2 wt %, greater than about 0.5 wt %, greater than about 1 wt %, greater than about 2 wt %, greater than about 5 wt %, greater than about 10 wt %, greater than about 15 wt %, greater than about 20 wt %, greater than about 25 wt %, greater than about 30 wt %, greater than about 35 wt %, greater than about 40 wt %, greater than about 45 wt %, greater than about 50 wt %, greater than about 55 wt %, greater than about 60 wt %, greater than about 65 wt %, greater than about 70 wt %, greater than about 75 wt %, greater than about 80 wt %, greater than about 85 wt %, greater than about 90 wt %, with the weight percentages being relative to the total weight of the freshening composition.

2. Preferred Blends of Perfume Raw Materials

One of ordinary skill in the art given the guidance of this disclosure will be able to formulate an unlimited variety of freshening composition comprising one or more of the compounds described herein. Some non-limiting, preferred blends of perfume raw materials for use in freshening compositions of the present invention are described herein, and more specifically in the Examples. A blend of perfume raw materials comprises a plurality of perfume raw materials. It is understood and one of ordinary skill in the art will appreciate that, if not clearly contradicted by the content of this specification, each embodiment of a preferred blend of perfume raw materials and/or features/elements disclosed as part of that embodiment can be combined with any of the embodiments hereinabove or hereinbelow.

In some embodiments of the present invention, a blend of perfume raw materials, referred to herein from time to time as Fragrance "Apple" or Apple Fragrance comprises one or more of the compounds listed in Table 1:

TABLE 1

Compounds in Fragrance Apple as identified by their respective CAS numbers and IUPAC nomenclature. One of ordinary skill in the art will appreciate that in this table and in Tables 2-4, allyl hexanoate refers to hexanoic acid, 2-propenyl ester, allyl heptanoate refers to heptanoic acid, 2-propyl ester, benzaldehyde refers to phenylmethanol aldehyde, and hexyl acetate refers to acetate C-6.

| CAS # | IUPAC NOMENCLATURE |
|---|---|
| 67634-00-8 | Allyl (3-methylbutoxy) acetate |
| 123-68-2 | Allyl hexanoate |
| 2705-87-5 | Allyl 3-cyclohexylpropanoate |
| 142-19-8 | Allyl heptanoate |
| 100-52-7 | Benzaldehyde |
| 103-95-7 | 3-(4-Isopropylphenyl)-2-methylpropanal |
| 18479-58-8 | 2,6-Dimethyloct-7-en-2-ol |
| 151-05-3 | 1,1-Dimethyl-2-phenylethyl acetate |
| 10094-34-5 | 1,1-Dimethyl-2-phenylethyl butyrate |
| 7452-79-1 | Ethyl 2-methylbutanoate |
| 4940-11-8 | 2-Ethyl-3-hydroxy-4H-pyran-4-one |
| 121-32-4 | 3-Ethoxy-4-hydroxybenzaldehyde |
| 105-95-3 | 1,4-Dioxacycloheptadecane-5,17-dione |
| 97-53-0 | 4-Allyl-2-methoxyphenol |
| 6413-10-1 | Ethyl (2-methyl-1,3-dioxolan-2-yl) acetate |
| 24851-98-7 | Methyl (3-oxo-2-pentylcyclopentyl) acetate |
| 6728-26-3 | Hex-2-enal |
| 142-92-7 | Hexyl acetate |
| 101-86-0 | 2-Benzylideneoctanal |
| 1335-66-6 | 4,5,6-Trimethylcyclohex-3-ene-1-carbaldehyde |
| 54464-57-2 | 1-(2,3,8,8-Tetramethyl-1,2,3,4,5,6,7,8-octahydronaphthalen-2-yl) ethanone |
| 3681-71-8 | Hex-3-en-1-yl acetate |

TABLE 1-continued

Compounds in Fragrance Apple as identified by their respective CAS numbers and IUPAC nomenclature. One of ordinary skill in the art will appreciate that in this table and in Tables 2-4, allyl hexanoate refers to hexanoic acid, 2-propenyl ester, allyl heptanoate refers to heptanoic acid, 2-propyl ester, benzaldehyde refers to phenylmethanol aldehyde, and hexyl acetate refers to acetate C-6.

| CAS # | IUPAC NOMENCLATURE |
|---|---|
| 928-96-1 | Hex-3-en-1-ol |
| 39255-32-8 | Ethyl 2-methylpentanoate |
| 104-61-0 | 5-Pentyldihydrofuran-2(3H)-one |
| 103-60-6 | 2-Phenoxyethyl 2-methylpropanoate |
| 93-92-5 | 1-Phenylethyl acetate |
| 68039-49-6 | 2,4-Dimethylcyclohex-3-ene-1-carbaldehyde |
| 104-67-6 | 5-Heptyldihydrofuran-2(3H)-one |
| 88-41-5 | 2-tert-Butylcyclohexyl acetate |

Thus, a preferred freshening composition of the present invention comprises a blend of perfume raw materials, which comprises one or more compounds selected from the group consisting of allyl (3-methylbutoxy) acetate, allyl hexanoate, allyl 3-cyclohexylpropanoate, allyl heptanoate, benzaldehyde, 3-(4-isopropylphenyl)-2-methylpropanal, 2,6-dimethyl oct-7-en-2-ol, 1,1-dimethyl-2-phenylethyl acetate, 1,1-dimethyl-2-phenylethyl butyrate, ethyl 2-methylbutanoate, 2-ethyl-3-hydroxy-4H-pyran-4-one, 3-ethoxy-4-hydroxybenzaldehyde, 1,4-dioxacycloheptadecane-5,17-dione, 4-allyl-2-methoxyphenol, ethyl (2-methyl-1,3-dioxolan-2-yl) acetate, methyl (3-oxo-2-pentylcyclopentyl) acetate, hex-2-enal, hexyl acetate, 2-benzylideneoctanal, 4,5,6-trimethylcyclohex-3-ene-1-carbaldehyde, 1-(2,3,8,8-tetramethyl-1,2,3,4,5,6,7,8-octahydronaphthalen-2-yl) ethanone, hex-3-en-1-yl acetate, hex-3-en-1-ol, ethyl 2-methylpentanoate, 5-pentyldihydrofuran-2(3H)-one, 2-phenoxyethyl 2-methylpropanoate, 1-phenylethyl acetate, 2,4-dimethyl cyclohex-3-ene-1-carbaldehyde, 5-heptyldihydrofuran-2(3H)-one, and 2-tert-butylcyclohexyl acetate. It is understood and one of ordinary skill in the art will appreciate that, if not clearly contradicted by the content of this specification, each of the one or more preceeding compounds can be combined with any of the embodiments hereinabove or hereinbelow, and in particular with any embodiment of a fragrance release modulator and/or features/elements disclosed as part of that embodiment.

In some embodiments of the present invention, a blend of perfume raw materials, referred to herein from time to time as Fragrance "Apple," consists of the compounds listed in Table 1.

Thus, a preferred blend of perfume raw materials of the present invention consists of allyl (3-methylbutoxy) acetate, allyl hexanoate, allyl 3-cyclohexylpropanoate, allyl heptanoate, benzaldehyde, 3-(4-isopropylphenyl)-2-methylpropanal, 2,6-dimethyloct-7-en-2-ol, 1,1-dimethyl-2-phenylethyl acetate, 1,1-dimethyl-2-phenylethyl butyrate, ethyl 2-methylbutanoate, 2-ethyl-3-hydroxy-4H-pyran-4-one, 3-ethoxy-4-hydroxybenzaldehyde, 1,4-dioxacycloheptadecane-5,17-dione, 4-allyl-2-methoxyphenol, ethyl (2-methyl-1,3-dioxolan-2-yl) acetate, methyl (3-oxo-2-pentylcyclopentyl) acetate, hex-2-enal, hexyl acetate, 2-benzylideneoctanal, 4,5,6-trimethylcyclohex-3-ene-1-carbaldehyde, 1-(2,3,8,8-tetramethyl-1,2,3,4,5,6,7,8-octahydronaphthalen-2-yl) ethanone, hex-3-en-1-yl acetate, hex-3-en-1-ol, ethyl 2-methylpentanoate, 5-pentyldihydrofuran-2(3H)-one, 2-phenoxyethyl 2-methylpropanoate, 1-phenylethyl acetate, 2,4-dimethylcyclohex-3-ene-1-carbaldehyde, 5-heptyldihydrofuran-2(3H)-one, and 2-tert-butylcyclohexyl acetate. It is understood and one of ordinary skill in the art will appreciate that, if not clearly contradicted by the content of this specification, each of the one or more preceeding compounds can be combined with any of the embodiments hereinabove or hereinbelow, and in particular with any embodiment of a fragrance release modulator and/or features/elements disclosed as part of that embodiment.

A further preferred blend of perfume raw materials of the present invention, referred to herein from time to time as Fragrance "Apple" or Apple Fragrance, comprises one or more compounds listed in Table 2 at the indicated weight percentage range.

TABLE 2

Compounds in Fragrance Apple as identified by their respective CAS numbers, IUPAC nomenclatures and weight percentage ranges. Weight percentage range given for each compound is in reference to the total weight of the blend of perfume raw materials.

| CAS # | IUPAC NOMENCLATURE | WEIGHT PERCENTAGE RANGE |
|---|---|---|
| 67634-00-8 | Allyl (3-methylbutoxy) acetate | About 0.1-20.0 |
| 123-68-2 | Allyl hexanoate | About 0.1-10.0 |
| 2705-87-5 | Allyl 3-cyclohexylpropanoate | About 0.1-10.0 |
| 142-19-8 | Allyl heptanoate | About 0.1-10.0 |
| 100-52-7 | Benzaldehyde | About 0.1-10.0 |
| 103-95-7 | 3-(4-Isopropylphenyl)-2-methylpropanal | About 0.1-10.0 |
| 18479-58-8 | 2,6-Dimethyloct-7-en-2-ol | About 1.0-20.0 |
| 151-05-3 | 1,1-Dimethyl-2-phenylethyl acetate | About 0.1-10.0 |
| 10094-34-5 | 1,1-Dimethyl-2-phenylethyl butyrate | About 1.0-20.0 |
| 7452-79-1 | Ethyl 2-methylbutanoate | About 0.1-10.0 |
| 4940-11-8 | 2-Ethyl-3-hydroxy-4H-pyran-4-one | About 0.1-10.0 |
| 121-32-4 | 3-Ethoxy-4-hydroxybenzaldehyde | About 0.1-10.0 |
| 105-95-3 | 1,4-Dioxacycloheptadecane-5,17-dione | About 1.0-50.0 |
| 97-53-0 | 4-Allyl-2-methoxyphenol | About 1.0-20.0 |
| 6413-10-1 | Ethyl (2-methyl-1,3-dioxolan-2-yl) acetate | About 0.1-20.0 |
| 24851-98-7 | Methyl (3-oxo-2-pentylcyclopentyl) acetate | About 1.0-20.0 |
| 6728-26-3 | Hex-2-enal | About 0.01-10.0 |
| 142-92-7 | Hexyl acetate | About 0.1-10.0 |
| 101-86-0 | 2-Benzylideneoctanal | About 1.0-20.0 |
| 1335-66-6 | 4,5,6-Trimethylcyclohex-3-ene-1-carbaldehyde | About 1.0-20.0 |
| 54464-57-2 | 1-(2,3,8,8-Tetramethyl-1,2,3,4,5,6,7,8-octahydronaphthalen-2-yl) ethanone | About 1.0-20.0 |
| 3681-71-8 | Hex-3-en-1-yl acetate | About 0.1-10.0 |
| 928-96-1 | Hex-3-en-1-ol | About 0.1-10.0 |
| 39255-32-8 | Ethyl 2-methylpentanoate | About 0.1-10.0 |
| 104-61-0 | 5-Pentyldihydrofuran-2(3H)-one | About 0.1-10.0 |
| 103-60-6 | 2-Phenoxyethyl 2-methylpropanoate | About 0.1-20 |
| 93-92-5 | 1-Phenylethyl acetate | About 0.1-10 |
| 68039-49-6 | 2,4-Dimethylcyclohex-3-ene-1-carbaldehyde | About 0.1-20.0 |
| 104-67-6 | 5-Heptyldihydrofuran-2(3H)-one | About 2.0-80.0 |
| 88-41-5 | 2-tert-Butylcyclohexyl acetate | About 2.0-80.0 |
| | TOTAL | 100.00 |

Thus, a preferred blend of perfume raw materials of the present invention comprises one or more compounds with a weight percentage range selected from the group consisting of from about 0.1-20.0 wt % of allyl (3-methylbutoxy) acetate, from about 0.1-10.0 wt % of allyl hexanoate, from about 0.1-10.0 wt % of allyl 3-cyclohexylpropanoate, from about 0.1-10.0 wt % of allyl heptanoate, from about 0.1-10.0 wt % of benzaldehyde, from about 0.1-10.0 wt % of 3-(4-isopropylphenyl)-2-methylpropanal, from about 1.0-20.0 wt % of 2,6-dimethyloct-7-en-2-ol, from about 0.1-10.0 wt % of 1,1-dimethyl-2-phenylethyl acetate, from about 1.0-20.0 wt % of 1,1-dimethyl-2-phenylethyl butyrate, from about 0.1-10.0 wt % of ethyl 2-methylbutanoate, from about 0.1-10.0 wt % of 2-ethyl-3-hydroxy-4H-pyran-4-one, from about 0.1-10.0 wt % of 3-ethoxy-4-hydroxybenzaldehyde, from about 1.0-50.0 wt % of 1,4-dioxacycloheptadecane-5,17-dione, from about 1.0-20.0 wt % of 4-allyl-2-methoxyphenol, from about 0.1-20.0 wt % of ethyl (2-methyl-1,3-dioxolan-2-yl) acetate, from about 1.0-20.0 wt % of methyl (3-oxo-2-pentylcyclopentyl) acetate, from about 0.01-10.0 wt % of hex-2-enal, from about 0.1-10.0 wt % of hexyl acetate, from about 1.0-20.0 wt % of 2-benzylideneoctanal, from about 1.0-20.0 wt % of 4,5,6-trimethylcyclohex-3-ene-1-carbaldehyde, from about 1.0-20.0 wt % of 1-(2,3,8,8-tetramethyl-1,2,3,4,5,6,7,8-octahydronaphthalen-2-yl) ethanone, from about 0.1-10.0 wt % of hex-3-en-1-yl acetate, from about 0.1-10.0 wt % of hex-3-en-1-ol, from about 0.1-10.0 wt % of ethyl 2-methylpentanoate, from about 0.1-10.0 wt % of 5-pentyldihydrofuran-2(3H)-one, from about 0.1-20.0 wt % of 2,4-dimethylcyclohex-3-ene-1-carbaldehyde, from about 2.0-80.0 wt % of 5-heptyldihydrofuran-2(3H)-one, and from about 2.0-80.0 wt % of 2-tert-butylcyclohexyl acetate, wherein the weight percentage range of each compound is with reference to the total weight of the blend of the perfume raw materials. It is understood and one of ordinary skill in the art will appreciate that, if not clearly contradicted by the content of this specification, each of the one or more preceeding compounds can be combined with any of the embodiments hereinabove or hereinbelow, and in particular with any embodiment of a fragrance release modulator and/or features/elements disclosed as part of that embodiment.

In some embodiments of the present invention, a blend of perfume raw materials, referred to herein from time to time as Fragrance "Apple" or Apple Fragrance consists of the compounds listed in Table 2 at the indicated weight percentage range.

Thus, a preferred blend of perfume raw materials of the present invention consists of from about 0.1-20.0 wt % of allyl (3-methylbutoxy) acetate, from about 0.1-10.0 wt % of allyl hexanoate, from about 0.1-10.0 wt % of allyl 3-cyclohexylpropanoate, from about 0.1-10.0 wt % of allyl heptanoate, from about 0.1-10.0 wt % of benzaldehyde, from about 0.1-10.0 wt % of 3-(4-isopropylphenyl)-2-methylpropanal, from about 1.0-20.0 wt % of 2,6-dimethyloct-7-en-2-ol, from about 0.1-10.0 wt % of 1,1-dimethyl-2-phenylethyl acetate, from about 1.0-20.0 wt % of 1,1-dimethyl-2-phenylethyl butyrate, from about 0.1-10.0 wt % of ethyl 2-methylbutanoate, from about 0.1-10.0 wt % of 2-ethyl-3-hydroxy-4H-pyran-4-one, from about 0.1-10.0 wt % of 3-ethoxy-4-hydroxybenzaldehyde, from about 1.0-50.0 wt % of 1,4-dioxacycloheptadecane-5,17-dione, from about 1.0-20.0 wt % of 4-allyl-2-methoxyphenol, from about 0.1-20.0 wt % of ethyl (2-methyl-1,3-dioxolan-2-yl) acetate, from about 1.0-20.0 wt % of methyl (3-oxo-2-pentylcyclopentyl) acetate, from about 0.01-10.0 wt % of hex-2-enal, from about 0.1-10.0 wt % of hexyl acetate, from about 1.0-20.0 wt % of 2-benzylideneoctanal, from about 1.0-20.0 wt % of 4,5,6-trimethylcyclohex-3-ene-1-carbaldehyde, from about 1.0-20.0 wt % of 1-(2,3,8,8-tetramethyl-1,2,3,4,5,6,7,8-octahydronaphthalen-2-yl) ethanone, from about 0.1-10.0 wt % of hex-3-en-1-yl acetate, from about 0.1-10.0 wt % of hex-3-en-1-ol, from about 0.1-10.0 wt % of ethyl 2-methylpentanoate, from about 0.1-10.0 wt % of 5-pentyldihydrofuran-2(3H)-one, from about 0.1-20.0 wt % of 2,4-dimethylcyclohex-3-ene-1-carbaldehyde, from about 2.0-80.0 wt % of 5-heptyldihydrofuran-2(3H)-one, and from about 2.0-80.0 wt % of 2-tert-butylcyclohexyl acetate, wherein the weight percentage range of each compound is with reference to the total weight of the blend of the perfume raw materials. It is understood and one of ordinary skill in the art will appreciate that, if not clearly contradicted by the content of this specification, each of the one or more preceeding compounds can be combined with any of the embodiments hereinabove or hereinbelow, and in particular with any embodiment of a fragrance release modulator and/or features/elements disclosed as part of that embodiment.

A further preferred blend of perfume raw materials of the present invention, referred to herein from time to time as Fragrance "Apple" or Apple Fragrance comprises one or more compounds listed in Table 3 at the indicated weight percentage range.

TABLE 3

Compounds in Fragrance Apple as identified by their respective CAS numbers, IUPAC nomenclatures and weight percentage ranges. Weight percentage range given for each compound is in reference to the total weight of the blend of the perfume raw materials.

| CAS # | IUPAC NOMENCLATURE | WEIGHT PERCENTAGE RANGE |
|---|---|---|
| 67634-00-8 | Allyl (3-methylbutoxy) acetate | About 0.2-10.0 |
| 123-68-2 | Allyl hexanoate | About 0.1-4.0 |
| 2705-87-5 | Allyl 3-cyclohexylpropanoate | About 0.1-5.0 |
| 142-19-8 | Allyl heptanoate | About 0.1-5.0 |
| 100-52-7 | Benzaldehyde | About 0.1-3.0 |
| 103-95-7 | 3-(4-Isopropylphenyl)-2-methylpropanal | About 0.1-5.0 |
| 18479-58-8 | 2,6-Dimethyloct-7-en-2-ol | About 1.0-10.0 |
| 151-05-3 | 1,1-Dimethyl-2-phenylethyl acetate | About 0.1-5.0 |
| 10094-34-5 | 1,1-Dimethyl-2-phenylethyl butyrate | About 1.0-10.0 |
| 7452-79-1 | Ethyl 2-methylbutanoate | About 0.1-5.0 |
| 4940-11-8 | 2-Ethyl-3-hydroxy-4H-pyran-4-one | About 0.1-2.0 |
| 121-32-4 | 3-Ethoxy-4-hydroxybenzaldehyde | About 0.1-5.0 |
| 105-95-3 | 1,4-Dioxacycloheptadecane-5,17-dione | About 1.0-20.0 |
| 97-53-0 | 4-Allyl-2-methoxyphenol | About 1.0-10.0 |
| 6413-10-1 | Ethyl (2-methyl-1,3-dioxolan-2-yl) acetate | About 0.2-10.0 |
| 24851-98-7 | Methyl (3-oxo-2-pentylcyclopentyl) acetate | About 1.0-10.0 |
| 6728-26-3 | Hex-2-enal | About 0.01-1.0 |
| 142-92-7 | Hexyl acetate | About 0.1-8.0 |
| 101-86-0 | 2-Benzylideneoctanal | About 1.0-10.0 |
| 1335-66-6 | 4,5,6-Trimethylcyclohex-3-ene-1-carbaldehyde | About 1.0-10.0 |
| 54464-57-2 | 1-(2,3,8,8-Tetramethyl-1,2,3,4,5,6,7,8-octahydronaphthalen-2-yl) ethanone | About 1.0-10.0 |
| 3681-71-8 | Hex-3-en-1-yl acetate | About 0.1-5.0 |
| 928-96-1 | Hex-3-en-1-ol | About 0.1-7.0 |
| 39255-32-8 | Ethyl 2-methylpentanoate | About 0.1-5.0 |
| 104-61-0 | 5-Pentyldihydrofuran-2(3H)-one | About 0.1-7.0 |
| 103-60-6 | 2-Phenoxyethyl 2-methylpropanoate | About 0.1-10.0 |
| 93-92-5 | 1-Phenylethyl acetate | About 0.1-3.0 |
| 68039-49-6 | 2,4-Dimethylcyclohex-3-ene-1-carbaldehyde | About 0.2-10.0 |
| 104-67-6 | 5-Heptyldihydrofuran-2(3H)-one | About 2.0-50.0 |
| 88-41-5 | 2-tert-Butylcyclohexyl acetate | About 2.0-50.0 |
| | TOTAL | 100.00 |

Thus, a preferred blend of perfume raw materials of the present invention comprises one or more compounds with a weight percentage range selected from the group consisting of from about 0.2-10.0 wt % of allyl (3-methylbutoxy) acetate, from about 0.1-4.0 wt % of allyl hexanoate, from about 0.1-5.0 wt % of allyl 3-cyclohexylpropanoate, from about 0.1-5.0 wt % of allyl heptanoate, from about 0.1-3.0 wt % of benzaldehyde, from about 0.1-5.0 wt % of 3-(4-isopropylphenyl)-2-methylpropanal, from about 1.0-10.0 wt % of 2,6-dimethyloct-7-en-2-ol, from about 0.1-5.0 wt % of 1,1-dimethyl-2-phenylethyl acetate, from about 1.0-10.0 wt % of 1,1-dimethyl-2-phenylethyl butyrate, from about 0.1-5.0 wt % of ethyl 2-methylbutanoate, from about 0.1-2.0 wt % of 2-ethyl-3-hydroxy-4H-pyran-4-one, from about 0.1-

5.0 wt % of 3-ethoxy-4-hydroxybenzaldehyde, from about 1.0-20.0 wt % of 1,4-dioxacycloheptadecane-5,17-dione, from about 1.0-10.0 wt % of 4-allyl-2-methoxyphenol, from about 0.2-10.0 wt % of ethyl (2-methyl-1,3-dioxolan-2-yl) acetate, from about 1.0-10.0 wt % of methyl (3-oxo-2-pentylcyclopentyl) acetate, from about 0.01-1.0 wt % of hex-2-enal, from about 0.1-8.0 wt % of hexyl acetate, from about 1.0-10.0 wt % of 2-benzylideneoctanal, from about 1.0-10.0 wt % of 4,5,6-trimethylcyclohex-3-ene-1-carbaldehyde, from about 1.0-10.0 wt % of 1-(2,3,8,8-tetramethyl-1,2,3,4,5,6,7,8-octahydronaphthalen-2-yl) ethanone, from about 0.1-5.0 wt % of hex-3-en-1-yl acetate, from about 0.1-7.0 wt % of hex-3-en-1-ol, from about 0.1-5.0 wt % of ethyl 2-methylpentanoate, from about 0.1-7.0 wt % of 5-pentyldihydrofuran-2(3H)-one, from about 0.2-10.0 wt % of 2-phenoxyethyl 2-methylpropanoate, from about 0.1-3.0 wt % of 1-phenylethyl acetate, from about 0.2-10.0 wt % of 2,4-dimethylcyclohex-3-ene-1-carbaldehyde, from about 2.0-50.0 wt % of 5-heptyldihydrofuran-2(3H)-one, and from about 2.0-50.0 wt % of 2-tert-butylcyclohexyl acetate, wherein the weight percentage range of each compound is with reference to the total weight of the blend of the perfume raw materials. It is understood and one of ordinary skill in the art will appreciate that, if not clearly contradicted by the content of this specification, each of the one or more preceeding compounds can be combined with any of the embodiments hereinabove or hereinbelow, and in particular with any embodiment of a fragrance release modulator and/or features/elements disclosed as part of that embodiment.

In some embodiments of the present invention, a blend of perfume raw materials, referred to herein from time to time as Fragrance "Apple or Apple Fragrance" consists of the compounds listed in Table 3 at the indicated weight percentage range.

Thus, a preferred blend of perfume raw materials of the present invention consists of from about 0.2-10.0 wt % of allyl (3-methylbutoxy) acetate, from about 0.1-4.0 wt % of allyl hexanoate, from about 0.1-5.0 wt % of allyl 3-cyclohexylpropanoate, from about 0.1-5.0 wt % of allyl heptanoate, from about 0.1-3.0 wt % of benzaldehyde, from about 0.1-5.0 wt % of 3-(4-isopropylphenyl)-2-methylpropanal, from about 1.0-10.0 wt % of 2,6-dimethyloct-7-en-2-ol, from about 0.1-5.0 wt % of 1,1-dimethyl-2-phenylethyl acetate, from about 1.0-10.0 wt % of 1,1-dimethyl-2-phenylethyl butyrate, from about 0.1-5.0 wt % of ethyl 2-methylbutanoate, from about 0.1-2.0 wt % of 2-ethyl-3-hydroxy-4H-pyran-4-one, from about 0.1-5.0 wt % of 3-ethoxy-4-hydroxybenzaldehyde, from about 1.0-20.0 wt % of 1,4-dioxacycloheptadecane-5,17-dione, from about 1.0-10.0 wt % of 4-allyl-2-methoxyphenol, from about 0.2-10.0 wt % of ethyl (2-methyl-1,3-dioxolan-2-yl) acetate, from about 1.0-10.0 wt % of methyl (3-oxo-2-pentylcyclopentyl) acetate, from about 0.01-1.0 wt % of hex-2-enal, from about 0.1-8.0 wt % of hexyl acetate, from about 1.0-10.0 wt % of 2-benzylideneoctanal, from about 1.0-10.0 wt % of 4,5,6-trimethylcyclohex-3-ene-1-carbaldehyde, from about 1.0-10.0 wt % of 1-(2,3,8,8-tetramethyl-1,2,3,4,5,6,7,8-octahydronaphthalen-2-yl) ethanone, from about 0.1-5.0 wt % of hex-3-en-1-yl acetate, from about 0.1-7.0 wt % of hex-3-en-1-ol, from about 0.1-5.0 wt % of ethyl 2-methylpentanoate, from about 0.1-7.0 wt % of 5-pentyldihydrofuran-2(3H)-one, from about 0.2-10.0 wt % of 2-phenoxyethyl 2-methylpropanoate, from about 0.1-3.0 wt % of 1-phenylethyl acetate, from about 0.2-10.0 wt % of 2,4-dimethylcyclohex-3-ene-1-carbaldehyde, from about 2.0-50.0 wt % of 5-heptyldihydrofuran-2(3H)-one, and from about 2.0-50.0 wt % of 2-tert-butylcyclohexyl acetate, wherein the weight percentage range of each compound is with reference to the total weight of the blend of the perfume raw materials. It is understood and one of ordinary skill in the art will appreciate that, if not clearly contradicted by the content of this specification, each of the one or more preceeding compounds can be combined with any of the embodiments hereinabove or hereinbelow, and in particular with any embodiment of a fragrance release modulator and/or features/elements disclosed as part of that embodiment.

A further preferred blend of perfume raw materials of the present invention, referred to herein from time to time as Fragrance "Apple" or Apple Fragrance comprises one or more compounds listed in Table 4 at the indicated weight percentage.

TABLE 4

Compounds in Fragrance Apple as identified by their respective CAS numbers, IUPAC nomenclatures and weight percentages. Weight percentage given for each compound is in reference to the total weight of the blend of the perfume raw materials.

| CAS # | IUPAC NOMENCLATURE | WEIGHT PERCENTAGE |
|---|---|---|
| 67634-00-8 | Allyl (3-methylbutoxy) acetate | About 2.0 |
| 123-68-2 | Allyl hexanoate | About 0.4 |
| 2705-87-5 | Allyl 3-cyclohexylpropanoate | About 0.5 |
| 142-19-8 | Allyl heptanoate | About 1.0 |
| 100-52-7 | Benzaldehyde | About 0.3 |
| 103-95-7 | 3-(4-Isopropylphenyl)-2-methylpropanal | About 0.5 |
| 18479-58-8 | 2,6-Dimethyloct-7-en-2-ol | About 5.0 |
| 151-05-3 | 1,1-Dimethyl-2-phenylethyl acetate | About 1.0 |
| 10094-34-5 | 1,1-Dimethyl-2-phenylethyl butyrate | About 5.0 |
| 7452-79-1 | Ethyl 2-methylbutanoate | About 0.5 |
| 4940-11-8 | 2-Ethyl-3-hydroxy-4H-pyran-4-one | About 0.2 |
| 121-32-4 | 3-Ethoxy-4-hydroxybenzaldehyde | About 1.0 |
| 105-95-3 | 1,4-Dioxacycloheptadecane-5,17-dione | About 10.0 |
| 97-53-0 | 4-Allyl-2-methoxyphenol | About 3.0 |
| 6413-10-1 | Ethyl (2-methyl-1,3-dioxolan-2-yl) acetate | About 2.0 |
| 24851-98-7 | Methyl (3-oxo-2-pentylcyclopentyl) acetate | About 5.0 |
| 6728-26-3 | Hex-2-enal | About 0.1 |
| 142-92-7 | Hexyl acetate | About 0.8 |
| 101-86-0 | 2-Benzylideneoctanal | About 5.0 |
| 1335-66-6 | 4,5,6-Trimethylcyclohex-3-ene-1-carbaldehyde | About 5.0 |
| 54464-57-2 | 1-(2,3,8,8-Tetramethyl-1,2,3,4,5,6,7,8-octahydronaphthalen-2-yl) ethanone | About 5.0 |
| 3681-71-8 | Hex-3-en-1-yl acetate | About 0.5 |
| 928-96-1 | Hex-3-en-1-ol | About 0.7 |
| 39255-32-8 | Ethyl 2-methylpentanoate | About 0.5 |
| 104-61-0 | 5-Pentyldihydrofuran-2(3H)-one | About 0.7 |
| 103-60-6 | 2-Phenoxyethyl 2-methylpropanoate | About 2.0 |
| 93-92-5 | 1-Phenylethyl acetate | About 0.3 |
| 68039-49-6 | 2,4-Dimethylcyclohex-3-ene-1-carbaldehyde | About 2.0 |
| 104-67-8 | 5-Heptyldihydrofuran-2(3H)-one | About 15.0 |
| 88-41-5 | 2-tert-Butylcyclohexyl acetate | About 25.0 |
| | TOTAL | 100.00 |

Thus, a preferred blend of perfume raw material of the present invention comprises one or more compounds with a weight percentage selected from the group consisting of about 2.0 wt % of allyl (3-methylbutoxy) acetate, about 0.4 wt % of allyl hexanoate, about 0.5 wt % of allyl 3-cyclohexylpropanoate, about 1.0 wt % of allyl heptanoate, about 0.3 wt % of benzaldehyde, about 0.5 wt % of 3-(4-isopropylphenyl)-2-methylpropanal, about 5.0 wt % of 2,6-dimethyloct-7-en-2-ol, about 1.0 wt % of 1,1-dimethyl-2-phenylethyl acetate, about 5.0 wt % of 1,1-dimethyl-2-phenylethyl butyrate, about 0.5 wt % of ethyl 2-methylbutanoate, about 0.2 wt % of 2-ethyl-3-hydroxy-4H-pyran-4-one, about 1.0 wt % of 3-ethoxy-4-hydroxybenzaldehyde, about 10.0 wt % of 1,4-dioxacycloheptadecane-5,17-dione, about 3.0 wt % of 4-allyl-2-methoxyphenol, about 2.0 wt % of ethyl (2-methyl-1,3-dioxolan-2-yl) acetate, about 5.0 wt % of methyl (3-oxo-2-pentylcyclopentyl) acetate, about 0.1 wt % of hex-2-enal, about 0.8 wt % of hexyl acetate, about 5.0 wt % of 2-benzylideneoctanal, about 5.0 wt % of 4,5,6-trimethylcyclohex-3-ene-1-carbaldehyde, about 5.0 wt % of 1-(2,3,8,8-tetramethyl-1,2,3,4,5,6,7,8-octahydronaphthalen-2-yl) ethanone, about 0.5 wt % of hex-3-en-1-yl acetate, about 0.7 wt % of hex-3-en-1-ol, about 0.5 wt % of ethyl 2-methylpentanoate, about 0.7 wt % of 5-pentyldihydrofuran-2(3H)-one, about 2.0 wt % of 2-phenoxyethyl 2-methylpropanoate, about 0.3 wt % of 1-phenylethyl acetate, about 2.0 wt % of 2,4-dimethylcyclohex-3-ene-1-carbaldehyde, about 15.0 wt % of 5-heptyldihydrofuran-2(3H)-one, and about 25.0 wt % of 2-tert-butylcyclohexyl acetate, wherein the weight percentage of each compound is with reference to the total weight of the blend of the perfume raw materials. It is understood and one of ordinary skill in the art will appreciate that, if not clearly contradicted by the content of this specification, each of the one or more preceeding compounds can be combined with any of the embodiments hereinabove or hereinbelow, and in particular with any embodiment of a fragrance release modulator and/or features/elements disclosed as part of that embodiment.

In some embodiments of the present invention, a preferred blend of perfume raw materials, referred to herein from time to time as Fragrance "Apple or Apple Fragrance" consists of the compounds listed in Table 4 at the indicated weight percentage.

Thus, a preferred blend of perfume raw materials of the present invention consists of about 2.0 wt % of allyl (3-methylbutoxy) acetate, about 0.4 wt % of allyl hexanoate, about 0.5 wt % of allyl 3-cyclohexylpropanoate, about 1.0 wt % of allyl heptanoate, about 0.3 wt % of benzaldehyde, about 0.5 wt % of 3-(4-isopropylphenyl)-2-methylpropanal, about 5.0 wt % of 2,6-dimethyloct-7-en-2-ol, about 1.0 wt % of 1,1-dimethyl-2-phenylethyl acetate, about 5.0 wt % of 1,1-dimethyl-2-phenylethyl butyrate, about 0.5 wt % of ethyl 2-methylbutanoate, about 0.2 wt % of 2-ethyl-3-hydroxy-4H-pyran-4-one, about 1.0 wt % of 3-ethoxy-4-hydroxybenzaldehyde, about 10.0 wt % of 1,4-dioxacycloheptadecane-5,17-dione, about 3.0 wt % of 4-allyl-2-methoxyphenol, about 2.0 wt % of ethyl (2-methyl-1,3-dioxolan-2-yl) acetate, about 5.0 wt % of methyl (3-oxo-2-pentylcyclopentyl) acetate, about 0.1 wt % of hex-2-enal, about 0.8 wt % of hexyl acetate, about 5.0 wt % of 2-benzylideneoctanal, about 5.0 wt % of 4,5,6-trimethylcyclohex-3-ene-1-carbaldehyde, about 5.0 wt % of 1-(2,3,8,8-tetramethyl-1,2,3,4,5,6,7,8-octahydronaphthalen-2-yl) ethanone, about 0.5 wt % of hex-3-en-1-yl acetate, about 0.7 wt % of hex-3-en-1-ol, about 0.5 wt % of ethyl 2-methylpentanoate, about 0.7 wt % of 5-pentyldihydrofuran-2(3H)-one, about 2.0 wt % of 2-phenoxyethyl 2-methylpropanoate, about 0.3 wt % of 1-phenylethyl acetate, about 2.0 wt % of 2,4-dimethylcyclohex-3-ene-1-carbaldehyde, about 15.0 wt % of 5-heptyldihydrofuran-2(3H)-one, and about 25.0 wt % of 2-tert-butylcyclohexyl acetate, wherein the weight percentage of each compound is with reference to the total weight of the blend of the perfume raw materials. It is understood and one of ordinary skill in the art will appreciate that, if not clearly contradicted by the content of this specification, each of the one or more preceeding compounds can be combined with any of the embodiments hereinabove or hereinbelow, and in particular with any embodiment of a fragrance release modulator and/or features/elements disclosed as part of that embodiment.

In some embodiments of the present invention, a blend of perfume raw materials, referred to herein from time to time as Fragrance "Floral Fresh" or Floral Fresh Fragrance, comprises one or more of the compounds listed in Table 5.

TABLE 5

Compounds in Fragrance Floral Fresh as identified by their respective CAS numbers and IUPAC nomenclature. One of ordinary skill in the art will appreciate that hexyl salicylate refers to benzoic acid, 2-hydroxy-, hexyl ester.

| CAS # | IUPAC NOMENCLATURE |
|---|---|
| 54464-57-2 | 1-(2,3,8,8-Tetramethyl-1,2,3,4,5,6,7,8-octahydronaphthalen-2-yl) ethanone |
| 24851-98-7 | Methyl (3-oxo-2-pentylcyclopentyl) acetate |
| 101-86-0 | 2-Benzylideneoctanal |
| 32388-55-9 | 1-Cedr-8-en-9-ylethanone |
| 32210-23-4 | 4-tert-Butylcyclohexyl acetate |
| 115-95-7 | 1,5-Dimethyl-1-vinylhex-4-en-1-yl acetate |
| 78-70-6 | 3,7-Dimethylocta-1,6-dien-3-ol |
| 1335-46-2 | 1-(2,6,6-Trimethylcyclohex-2-en-1-yl) pent-1-en-3-one |
| 63500-71-0 | 2-Isobutyl-4-methyltetrahydro-2H-pyran-4-ol |
| 105-95-3 | 1,4-Dioxacycloheptadecane-5,17-dione |
| 18479-58-8 | 2,6-Dimethyloct-7-en-2-ol |
| 103-95-7 | 3-(4-Isopropylphenyl)-2-methylpropanal |
| 6259-76-3 | Hexyl salicylate |
| 67634-15-5 | 3-(4-Ethylphenyl)-2,2-dimethylpropanal |
| 67634-14-4 | 3-(2-ethylphenyl)-2,2-dimethylpropanal |
| 5413-60-5 | 3a,4,5,6,7,7a-Hexahydro-1H-4,7-methanoinden-6-yl acetate |
| 8000-27-9 | Cedarwood oil, Virginian (*Juniperus virginiana L.*)* |
| 110-41-8 | 2-Methylundecanal |
| 101-48-4 | (2,2-Dimethoxyethyl) benzene |
| 112-45-8 | Undec-10-enal |
| 928-96-1 | Hex-3-en-1-ol |
| 1205-17-0 | 3-(1,3-Benzodioxol-5-yl)-2-methylpropanal |
| 93-92-5 | 1-Phenylethyl acetate |
| 3738-00-9 | 3a,6,6,9a-Tetramethyldodecahydronaphtho[2,1-b] furan |
| 67634-00-8 | Allyl (3-methylbutoxy) acetate |
| 56973-85-4 | 1-(5,5-Dimethylcyclohex-1-en-1-yl) pent-4-en-1-one |

*Cedarwood oil, Virginian (*Juniperus virginiana L.*) is entered in this table and in Tables 6-8 and 10 as the principal RIFM (Research Institute of Fragrance Materials) botanical nomenclature as it could not be found in the IUPAC database. In general, cedarwood oils extracted from *Juniperus virginiana* of the Cypressaceae family, also known as Virginian, red, eastern red or southern red cedar, as well as Bedford cedarwood, may be used. The main chemical componenets of cedarwood oil are α-cedrene, β-cedrene, thujopsene, other sesquiterpenes, cedrol and widdrol.

Thus, a preferred blend of perfume raw materials of the present invention comprises one or more compounds selected from the group consisting of 1-(2,3,8,8-tetramethyl-1,2,3,4,5,6,7,8-octahydronaphthalen-2-yl) ethanone, methyl (3-oxo-2-pentylcyclopentyl) acetate, 2-benzylideneoctanal, 1-cedr-8-en-9-ylethanone, 4-tert-butylcyclohexyl acetate, 1,5-dimethyl-1-vinylhex-4-en-1-yl acetate, 3,7-dimethylocta-1,6-dien-3-ol, 1-(2,6,6-trimethylcyclohex-2-en-1-yl) pent-1-en-3-one, 2-isobutyl-4-methyltetrahydro-2H-pyran-4-ol, 1,4-dioxacycloheptadecane-5,17-dione, 2,6-dimethyl oct-7-en-2-ol, 3-(4-isopropylphenyl)-2-methylpropanal, hexyl salicylate, 3-(4-ethylphenyl)-2,2-dimethylpropanal, 3-(2-ethylphenyl)-2,2-dimethylpropanal, 3a,4,5,6,7,7a-hexahydro-1H-4,7-methanoinden-6-yl acetate, Cedarwood oil, Virginian (*Juniperus virginiana* L.), 2-methylundecanal, (2,2-dimethoxyethyl) benzene, undec-10-enal, hex-3-en-1-ol, 3-(1,3-benzodioxol-5-yl)-2-methylpropanal, 1-phenylethyl acetate, 3a,6,6,9a-tetramethyldodecahydronaphtho[2,1-b] furan, allyl (3-methylbutoxy) acetate, and 1-(5,5-dimethylcyclohex-1-en-1-yl) pent-4-en-1-one. It is understood and one of ordinary skill in the art will appreciate that, if not clearly contradicted by the content of this specification, each of the one or more preceeding compounds can be combined with any of the embodiments hereinabove or hereinbelow, and in particular with any embodiment of a fragrance release modulator and/or features/elements disclosed as part of that embodiment.

In some embodiments of the present invention, a blend of perfume raw materials, referred to herein from time to time as Fragrance "Floral Fresh" or Floral Fresh Fragrance, consists of the compounds listed in Table 5.

Thus, a preferred blend of perfume raw materials of the present invention consists of 1-(2,3,8,8-tetramethyl-1,2,3,4,5,6,7,8-octahydronaphthalen-2-yl) ethanone, methyl (3-oxo-2-pentylcyclopentyl) acetate, 2-benzylideneoctanal, 1-cedr-8-en-9-ylethanone, 4-tert-butylcyclohexyl acetate, 1,5-dimethyl-1-vinylhex-4-en-1-yl acetate, 3,7-dimethylocta-1,6-dien-3-ol, 1-(2,6,6-trimethylcyclohex-2-en-1-yl) pent-1-en-3-one, 2-isobutyl-4-methyltetrahydro-2H-pyran-4-ol, 1,4-dioxacycloheptadecane-5,17-dione, 2,6-dimethyloct-7-en-2-ol, 3-(4-isopropylphenyl)-2-methylpropanal, hexyl salicylate, 3-(4-ethylphenyl)-2,2-dimethylpropanal, 3-(2-ethylphenyl)-2,2-dimethylpropanal, 3a,4,5,6,7,7a-hexahydro-1H-4,7-methanoinden-6-yl acetate, Cedarwood oil, Virginian (*Juniperus virginiana* L.), 2-methylundecanal, (2,2-dimethoxyethyl) benzene, undec-10-enal, hex-3-en-1-ol, 3-(1,3-benzodioxol-5-yl)-2-methylpropanal, 1-phenylethyl acetate, 3a,6,6,9a-tetramethyldodecahydronaphtho[2,1-b] furan, allyl (3-methylbutoxy) acetate, and 1-(5,5-dimethylcyclohex-1-en-1-yl) pent-4-en-1-one. It is understood and one of ordinary skill in the art will appreciate that, if not clearly contradicted by the content of this specification, each of the one or more preceeding compounds can be combined with any of the embodiments hereinabove or hereinbelow, and in particular with any embodiment of a fragrance release modulator and/or features/elements disclosed as part of that embodiment.

A further preferred blend of perfume raw materials of the present invention, referred to herein from time to time as "Floral Fresh" or Floral Fresh Fragrance, comprises one or more compounds listed in Table 6 at the indicated weight percentage range.

TABLE 6

Compounds in Fragrance Floral Fresh as identified by their respective CAS numbers, IUPAC nomenclatures and weight percentage ranges. Weight percentage range given for each compound is in reference to the total weight of the blend of the perfume raw materials.

| CAS # | IUPAC NOMENCLATURE | WEIGHT PERCENTAGE RANGE |
|---|---|---|
| 54464-57-2 | 1-(2,3,8,8-Tetramethyl-1,2,3,4,5,6,7,8-octahydronaphthalen-2-yl) ethanone | About 1.0-50.0 |
| 24851-98-7 | Methyl (3-oxo-2-pentylcyclopentyl) acetate | About 1.0-50.0 |
| 101-86-0 | 2-Benzylideneoctanal | About 1.0-50.0 |
| 32388-55-9 | 1-Cedr-8-en-9-ylethanone | About 0.5-20.0 |
| 32210-23-4 | 4-tert-Butylcyclohexyl acetate | About 0.5-20.0 |
| 115-95-7 | 1,5-Dimethyl-1-vinylhex-4-en-1-yl acetate | About 0.5-20.0 |
| 78-70-6 | 3,7-Dimethylocta-1,6-dien-3-ol | About 0.5-20.0 |
| 1335-46-2 | 1-(2,6,6-Trimethylcyclohex-2-en-1-yl) pent-1-en-3-one | About 0.5-20.0 |
| 63500-71-0 | 2-Isobutyl-4-methyltetrahydro-2H-pyran-4-ol | About 0.5-20.0 |
| 105-95-3 | 1,4-Dioxacycloheptadecane-5,17-dione | About 0.5-20.0 |
| 18479-58-8 | 2,6-Dimethyloct-7-en-2-ol | About 0.5-20.0 |
| 103-95-7 | 3-(4-Isopropylphenyl)-2-methylpropanal | About 0.1-15.0 |
| 6259-76-3 | Hexyl salicylate | About 0.1-15.0 |
| 67634-15-5 | 3-(4-Ethylphenyl)-2,2-dimethylpropanal | About 0.1-15.0 |
| 67634-14-4 | 3-(2-ethylphenyl)-2,2-dimethylpropanal | About 0.1-15.0 |
| 5413-60-5 | 3a,4,5,6,7,7a-Hexahydro-1H-4,7-methanoinden-6-yl acetate | About 0.1-15.0 |

TABLE 6-continued

Compounds in Fragrance Floral Fresh as identified by their respective CAS numbers, IUPAC nomenclatures and weight percentage ranges. Weight percentage range given for each compound is in reference to the total weight of the blend of the perfume raw materials.

| CAS # | IUPAC NOMENCLATURE | WEIGHT PERCENTAGE RANGE |
|---|---|---|
| 8000-27-9 | Cedarwood oil, Virginian (*Juniperus virginiana* L.) | About 0.1-15.0 |
| 110-41-8 | 2-Methylundecanal | About 0.1-15.0 |
| 101-48-4 | (2,2-Dimethoxyethyl) benzene | About 0.1 15.0 |
| 112-45-8 | Undec-10-enal | About 0.1-15.0 |
| 928-96-1 | Hex-3-en-1-ol | About 0.1-15.0 |
| 1205-17-0 | 3-(1,3-Benzodioxol-5-yl)-2-methylpropanal | About 0.1-15.0 |
| 93-92-5 | 1-Phenylethyl acetate | About 0.1-15.0 |
| 3738-00-9 | 3a,6,6,9a-Tetramethyldodecahydronaphtho[2,1-b]furan | About 0.1-15.0 |
| 67634-00-8 | Allyl (3-methylbutoxy) acetate | About 0.1-15.0 |
| 56973-85-4 | 1-(5,5-Dimethylcyclohex-1-en-1-yl) pent-4-en-1-one | About 0.01 15.0 |
| | TOTAL | 100.00 |

Thus, a preferred blend of perfume raw materials of the present invention comprises one or more compounds with a weight percentage selected from the group consisting of from about 1.0-50.0 wt % of 1-(2,3,8,8-tetramethyl-1,2,3,4,5,6,7,8-octahydronaphthalen-2-yl) ethanone, from about 1.0-50.0 wt % of methyl (3-oxo-2-pentylcyclopentyl) acetate, from about 1.0-50.0 wt % of 2-benzylideneoctanal, from about 0.5-20.0 wt % of 1-cedr-8-en-9-ylethanone, from about 0.5-20.0 wt % of 4-tert-butylcyclohexyl acetate, from about 0.5-20.0 wt % of 1,5-dimethyl-1-vinylhex-4-en-1-yl acetate, from about 0.5-20.0 wt % of 3,7-dimethylocta-1,6-dien-3-ol, from about 0.5-20.0 wt % of 1-(2,6,6-trimethylcyclohex-2-en-1-yl) pent-1-en-3-one, from about 0.5-20.0 wt % of 2-isobutyl-4-methyltetrahydro-2H-pyran-4-ol, from about 0.5-20.0 wt % of 1,4-dioxacycloheptadecane-5,17-dione, from about 0.5-20.0 wt % of 2,6-dimethyloct-7-en-2-ol, from about 0.1-15.0 wt % of 3-(4-isopropylphenyl)-2-methylpropanal, hexyl salicylate, from about 0.1-15.0 wt % of 3-(4-ethylphenyl)-2,2-dimethylpropanal, from about 0.1-15.0 wt % of 3-(2-ethylphenyl)-2,2-dimethylpropanal, from about 0.1-15.0 wt % of 3a,4,5,6,7,7a-hexahydro-1H-4,7-methanoinden-6-yl acetate, from about 0.1-15.0 wt % of Cedarwood oil, Virginian (*Juniperus virginiana* L.), from about 0.1-15.0 wt % of 2-methylundecanal, (2,2-dimethoxyethyl) benzene, from about 0.1-15.0 wt % of undec-10-enal, from about 0.1-15.0 wt % of hex-3-en-1-ol, from about 0.1-15.0 wt % of 3-(1,3-benzodioxol-5-yl)-2-methylpropanal, from about 0.1-15.0 wt % of 1-phenylethyl acetate, from about 0.1-15.0 wt % of 3a,6,6,9a-tetramethyldodecahydronaphtho[2,1-b] furan, from about 0.1-15.0 wt % of allyl (3-methylbutoxy) acetate, and from about 0.01-15.0 wt % of 1-(5,5-dimethylcyclohex-1-en-1-yl) pent-4-en-1-one, wherein the weight percentage range of each compound is with reference to the total weight of the blend of the perfume raw materials. It is understood and one of ordinary skill in the art will appreciate that, if not clearly contradicted by the content of this specification, each of the one or more preceeding compounds can be combined with any of the embodiments hereinabove or hereinbelow, and in particular with any embodiment of a fragrance release modulator and/or features/elements disclosed as part of that embodiment.

In some embodiments of the present invention, a blend of perfume raw materials, referred to herein from time to time as Fragrance "Floral Fresh" or Floral Fresh Fragrance, consists of the compounds listed in Table 6 at the indicated weight percentage range.

Thus, a preferred blend of perfume raw materials of the present invention consists of from about 1.0-50.0 wt % of 1-(2,3,8,8-tetramethyl-1,2,3,4,5,6,7,8-octahydronaphthalen-2-yl) ethanone, from about 1.0-50.0 wt % of methyl (3-oxo-2-pentylcyclopentyl) acetate, from about 1.0-50.0 wt % of 2-benzylideneoctanal, from about 0.5-20.0 wt % of 1-cedr-8-en-9-ylethanone, from about 0.5-20.0 wt % of 4-tert-butylcyclohexyl acetate, from about 0.5-20.0 wt % of 1,5-dimethyl-1-vinylhex-4-en-1-yl acetate, from about 0.5-20.0 wt % of 3,7-dimethylocta-1,6-dien-3-ol, from about 0.5-20.0 wt % of 1-(2,6,6-trimethylcyclohex-2-en-1-yl) pent-1-en-3-one, from about 0.5-20.0 wt % of 2-isobutyl-4-methyltetrahydro-2H-pyran-4-ol, from about 0.5-20.0 wt % of 1,4-dioxacycloheptadecane-5,17-dione, from about 0.5-20.0 wt % of 2,6-dimethyloct-7-en-2-ol, from about 0.1-15.0 wt % of 3-(4-isopropylphenyl)-2-methylpropanal, hexyl salicylate, from about 0.1-15.0 wt % of 3-(4-ethylphenyl)-2,2-dimethylpropanal, from about 0.1-15.0 wt % of 3-(2-ethylphenyl)-2,2-dimethylpropanal, from about 0.1-15.0 wt % of 3a,4,5,6,7,7a-hexahydro-1H-4,7-methanoinden-6-yl acetate, from about 0.1-15.0 wt % of Cedarwood oil, Virginian (*Juniperus virginiana* L.), from about 0.1-15.0 wt % of 2-methylundecanal, (2,2-dimethoxyethyl) benzene, from about 0.1-15.0 wt % of undec-10-enal, from about 0.1-15.0 wt % of hex-3-en-1-ol, from about 0.1-15.0 wt % of 3-(1,3-benzodioxol-5-yl)-2-methylpropanal, from about 0.1-15.0 wt % of 1-phenylethyl acetate, from about 0.1-15.0 wt % of 3a,6,6,9a-tetramethyldodecahydronaphtho[2,1-b] furan, from about 0.1-15.0 wt % of allyl (3-methylbutoxy) acetate, and from about 0.01-15.0 wt % of 1-(5,5-dimethylcyclohex-1-en-1-yl) pent-4-en-1-one, wherein the weight percentage range of each compound is with reference to the total weight of the blend of the perfume raw materials. It is understood and one of ordinary skill in the art will appreciate that, if not clearly contradicted by the content of this specification, each of the one or more preceeding compounds can be combined with any of the embodiments hereinabove or hereinbelow, and in particular with any embodiment of a fragrance release modulator and/or features/elements disclosed as part of that embodiment.

A further preferred blend of perfume raw material of the present invention, referred to herein from time to time as Fragrance "Floral Fresh" or Floral Fresh Fragrance, comprises one or more compounds listed in Table 7 at the indicated weight percentage range.

TABLE 7

Compounds in Fragrance Floral Fresh as identified by their respective CAS numbers, IUPAC nomenclatures and weight percentage ranges. Weight percentage range given for each compound is in reference to the total weight of the blend of the perfume raw materials.

| CAS # | IUPAC NOMENCLATURE | WEIGHT PERCENTAGE RANGE |
|---|---|---|
| 54464-57-2 | 1-(2,3,8,8-Tetramethyl-1,2,3,4,5,6,7,8-octahydronaphthalen-2-yl) ethanone | About 1.0-25.0 |
| 24851-98-7 | Methyl (3-oxo-2-pentylcyclopentyl) acetate | About 1.0-25.0 |
| 101-86-0 | 2-Benzylideneoctanal | About 1.0-25.0 |
| 32388-55-9 | 1-Cedr-8-en-9-ylethanone | About 1.0-10.0 |
| 32210-23-4 | 4-tert-Butylcyclohexyl acetate | About 1.0-10.0 |

TABLE 7-continued

Compounds in Fragrance Floral Fresh as identified by their respective CAS numbers, IUPAC nomenclatures and weight percentage ranges. Weight percentage range given for each compound is in reference to the total weight of the blend of the perfume raw materials.

| CAS # | IUPAC NOMENCLATURE | WEIGHT PERCENTAGE RANGE |
|---|---|---|
| 115-95-7 | 1,5-Dimethyl-1-vinylhex-4-en-1-yl acetate | About 1.0-10.0 |
| 78-70-6 | 3,7-Dimethylocta-1,6-dien-3-ol | About 1.0-10.0 |
| 1335-46-2 | 1-(2,6,6-Trimethylcyclohex-2-en-1-yl) pent-1-en-3-one | About 1.0-10.0 |
| 63500-71-0 | 2-Isobutyl-4-methyltetrahydro-2H-pyran-4-ol | About 1.0-10. |
| 105-95-3 | 1,4-Dioxacycloheptadecane-5,17-dione | About 1.0-10.0 |
| 18479-58-8 | 2,6-Dimethyloct-7-en-2-ol | About 1.0-10.0 |
| 103-95-7 | 3-(4-Isopropylphenyl)-2-methylpropanal | About 0.1-10.0 |
| 6259-76-3 | Hexyl salicylate | About 0.1-10.0 |
| 67634-15-5 | 3-(4-Ethylphenyl)-2,2-dimethylpropanal | About 0.1-10.0 |
| 67634-14-4 | 3-(2-ethylphenyl)-2,2-dimethylpropanal | About 0.1-6.0 |
| 5413-60-5 | 3a,4,5,6,7,7a-Hexahydro-1H-4,7-methanoinden-6-yl acetate | About 0.1-10.0 |
| 8000-27-9 | Cedarwood oil, Virginian (*Juniperus virginiana* L.) | About 0.1-10.0 |
| 110-41-8 | 2-Methylundecanal | About 0.1-10.0 |
| 101-48-4 | (2,2-Dimethoxyethyl) benzene | About 0.1-8.0 |
| 112-45-8 | Undec-10-enal | About 0.1-6.0 |
| 928-96-1 | Hex-3-en-1-ol | About 0.1-6.0 |
| 1205-17-0 | 3-(1,3-Benzodioxol-5-yl)-2-methylpropanal | About 0.1-6.0 |
| 93-92-5 | 1-Phenylethyl acetate | About 0.1-5.0 |
| 3738-00-9 | 3a,6,6,9a-Tetramethyldodecahydronaphtho[2,1-b]furan | About 0.1-5.0 |
| 67634-00-8 | Allyl (3-methylbutoxy) acetate | About 0.1-5.0 |
| 56973-85-4 | 1-(5,5-Dimethylcyclohex-1-en-1-yl) pent-4-en-1-one | Abou 0.01-5.0 |
| | TOTAL | 100.00 |

Thus, a preferred blend of perfume raw materials of the present invention comprises one or more compounds with a weight percentage selected from the group consisting of from about 1.0-25.0 wt % of 1-(2,3,8,8-tetramethyl-1,2,3,4,5,6,7,8-octahydronaphthalen-2-yl) ethanone, from about 1.0-25.0 wt % of methyl (3-oxo-2-pentylcyclopentyl) acetate, from about 1.0-25.0 wt % of 2-benzylideneoctanal, from about 1.0-10.0 wt % of 1-cedr-8-en-9-ylethanone, 1.0-10.0 wt % of 4-tert-butylcyclohexyl acetate, from about 1.0-10.0 wt % of 1,5-dimethyl-1-vinylhex-4-en-1-yl acetate, from about 1.0-10.0 wt % of 3,7-dimethylocta-1,6-dien-3-ol, from about 1.0-10.0 wt % of 1-(2,6,6-trimethylcyclohex-2-en-1-yl) pent-1-en-3-one, from about 1.0-10.0 wt % of 2-isobutyl-4-methyltetrahydro-2H-pyran-4-ol, from about 1.0-10.0 wt % of 1,4-dioxacycloheptadecane-5,17-dione, from about 1.0-10.0 wt % of 2,6-dimethyloct-7-en-2-ol, from about 0.1-10.0 wt % of 3-(4-isopropylphenyl)-2-methylpropanal, from about 0.1-10.0 wt % of hexyl salicylate, from about 0.1-10.0 wt % of 3-(4-ethylphenyl)-2,2-dimethylpropanal, from about 0.1-6.0 wt % of 3-(2-ethylphenyl)-2,2-dimethylpropanal, from about 0.1-10.0 wt % of 3a,4,5,6,7,7a-hexahydro-1H-4,7-methanoinden-6-yl acetate, from about 0.1-10.0 wt % of Cedarwood oil, Virginian (*Juniperus virginiana* L.), from about 0.1-10.0 wt % of 2-methylundecanal, from about 0.1-8.0 wt % of (2,2-dimethoxyethyl) benzene, from about 0.1-6.0 wt % of undec-10-enal, from about 0.1-6.0 wt % of hex-3-en-1-ol, from about 0.1-6.0 wt % of 3-(1,3-benzodioxol-5-yl)-2-methylpropanal, from about 0.1-5.0 wt % of 1-phenylethyl acetate, from about 0.1-5.0 wt % of 3a,6,6,9a-tetramethyldodecahydronaphtho

[2,1-b] furan, from about 0.1-5.0 wt % of allyl (3-methylbutoxy) acetate, and from about 0.01-5.0 wt % of 1-(5,5-dimethylcyclohex-1-en-1-yl) pent-4-en-1-one, wherein the weight percentage range of each compound is with reference to the total weight of the blend of the perfume raw materials. It is understood and one of ordinary skill in the art will appreciate that, if not clearly contradicted by the content of this specification, each of the one or more preceeding compounds can be combined with any of the embodiments hereinabove or hereinbelow, and in particular with any embodiment of a fragrance release modulator and/or features/elements disclosed as part of that embodiment.

In some embodiments of the present invention, a blend of perfume raw materials, referred to herein from time to time as Fragrance "Floral Fresh" or Floral Fresh Fragrance, consists of the compounds listed in Table 7 at the indicated weight percentage range.

Thus, a preferred blend of perfume raw materials of the present invention consists of from about 1.0-25.0 wt % of 1-(2,3,8,8-tetramethyl-1,2,3,4,5,6,7,8-octahydronaphthalen-2-yl) ethanone, from about 1.0-25.0 wt % of methyl (3-oxo-2-pentylcyclopentyl) acetate, from about 1.0-25.0 wt % of 2-benzylideneoctanal, from about 1.0-10.0 wt % of 1-cedr-8-en-9-ylethanone, from about 1.0-10.0 wt % of 4-tert-butylcyclohexyl acetate, from about 1.0-10.0 wt % of 1,5-dimethyl-1-vinylhex-4-en-1-yl acetate, from about 1.0-10.0 wt % of 3,7-dimethylocta-1,6-dien-3-ol, from about 1.0-10.0 wt % of 1-(2,6,6-trimethylcyclohex-2-en-1-yl) pent-1-en-3-one, from about 1.0-10.0 wt % of 2-isobutyl-4-methyltetrahydro-2H-pyran-4-ol, from about 1.0-10.0 wt % of 1,4-dioxacycloheptadecane-5,17-dione, from about 1.0-10.0 wt % of 2,6-dimethyloct-7-en-2-ol, from about 0.1-10.0 wt % of 3-(4-isopropylphenyl)-2-methylpropanal, from about 0.1-10 wt % of hexyl salicylate, from about 0.1-10.0 wt % of 3-(4-ethylphenyl)-2,2-dimethylpropanal, from about 0.1-6.0 wt % of 3-(2-ethylphenyl)-2,2-dimethylpropanal, from about 0.1-10.0 wt % of 3a,4,5,6,7,7a-hexahydro-1H-4,7-methanoinden-6-yl acetate, from about 0.1-10.0 wt % of Cedarwood oil, Virginian (*Juniperus virginiana* L.), from about 0.1-10.0 wt % of 2-methylundecanal, from about 0.1-8.0 wt % of (2,2-dimethoxyethyl) benzene, from about 0.1-6.0 wt % of undec-10-enal, from about 0.1-6.0 wt % of hex-3-en-1-ol, from about 0.1-6.0 wt % of 3-(1,3-benzodioxol-5-yl)-2-methylpropanal, 0.1-5.0 wt % of 1-phenylethyl acetate, from about 0.1-5.0 wt % of 3a,6,6,9a-tetramethyldodecahydronaphtho[2,1-b] furan, from about 0.1-5.0 wt % of allyl (3-methylbutoxy) acetate, and from about 0.01-5.0 wt % of 1-(5,5-dimethylcyclohex-1-en-1-yl) pent-4-en-1-one, wherein the weight percentage range of each compound is with reference to the total weight of the blend of the perfume raw materials. It is understood and one of ordinary skill in the art will appreciate that, if not clearly contradicted by the content of this specification, each of the one or more preceeding compounds can be combined with any of the embodiments hereinabove or hereinbelow, and in particular with any embodiment of a fragrance release modulator and/or features/elements disclosed as part of that embodiment.

A further preferred blend of perfume raw materials of the present invention, referred to herein from time to time as Fragrance "Floral Fresh or Floral Fresh Fragrance" comprises one or more compounds listed in Table 8 at the indicated weight percentage.

TABLE 8

Compounds in Fragrance Floral Fresh as identified by their respective CAS numbers, IUPAC nomenclatures and weight percentages. Weight percentage given for each compound is in reference to the total weight of the blend of perfume raw materials.

| CAS # | IUPAC NOMENCLATURE | WEIGHT PERCENTAGE |
|---|---|---|
| 54464-57-2 | 1-(2,3,8,8-Tetramethyl-1,2,3,4,5,6,7,8-octahydronaphthalen-2-yl) ethanone | About 14.0 |
| 24851-98-7 | Methyl (3-oxo-2-pentylcyclopentyl) acetate | About 12.0 |
| 101-86-0 | 2-Benzylideneoctanal | About 11.0 |
| 32388-55-9 | 1-Cedr-8-en-9-ylethanone | About 6.0 |
| 32210-23-4 | 4-tert-Butylcyclohexyl acetate | About 6.0 |
| 115-95-7 | 1,5-Dimethyl-1-vinylhex-4-en-1-yl acetate | About 6.0 |
| 78-70-6 | 3,7-Dimethylocta-1,6-dien-3-ol | About 6.0 |
| 1335-46-2 | 1-(2,6,6-Trimethylcyclohex-2-en-1-yl) pent-1-en-3-one | About 6.0 |
| 63500-71-0 | 2-Isobutyl-4-methyltetrahydro-2H-pyran-4-ol | About 6.0 |
| 105-95-3 | 1,4-Dioxacycloheptadecane-5,17-dione | About 6.0 |
| 18479-58-8 | 2,6-Dimethyloct-7-en-2-ol | About 6.0 |
| 103-95-7 | 3-(4-Isopropylphenyl)-2-methylpropanal | About 2.0 |
| 6259-76-3 | Hexyl salicylate | About 2.0 |
| 67634-15-5 | 3-(4-Ethylphenyl)-2,2-dimethylpropanal | About 1.40 |
| 67634-14-4 | 3-(2-ethylphenyl)-2,2-dimethylpropanal | About 0.6 |
| 5413-60-5 | 3a,4,5,6,7,7a-Hexahydro-1H-4,7-methanoinden-6-yl acetate | About 2.0 |
| 8000-27-9 | Cedarwood oil, Virginian (*Juniperus virginiana* L.) | About 2.0 |
| 110-41-8 | 2-Methylundecanal | About 1.0 |
| 101-48-4 | (2,2-Dimethoxyethyl) benzene | About 0.8 |
| 112-45-8 | Undec-10-enal | About 0.6 |
| 928-96-1 | Hex-3-en-1-ol | About 0.6 |
| 1205-17-0 | 3-(1,3-Benzodioxol-5-yl)-2-methylpropanal | About 0.6 |
| 93-92-5 | 1-Phenylethyl acetate | About 0.5 |
| 3738-00-9 | 3a,6,6,9a-Tetramethyldodecahydronaphtho[2,1-b]furan | About 0.4 |
| 67634-00-8 | Allyl (3-methylbutoxy) acetate | About 0.4 |
| 56973-85-4 | 1-(5,5-Dimethylcyclohex-1-en-1-yl) pent-4-en-1-one | About 0.1 |
| TOTAL | | 100.00 |

Thus, a preferred blend of perfume raw materials of the present invention comprises one or more compounds with a weight percentage selected from the group consisting of about 14.0 wt % of 1-(2,3,8,8-tetramethyl-1,2,3,4,5,6,7,8-octahydronaphthalen-2-yl) ethanone, about 12.0 wt % of methyl (3-oxo-2-pentylcyclopentyl) acetate, about 11.0 wt % of 2-benzylideneoctanal, about 6.0 wt % of 1-cedr-8-en-9-ylethanone, about 6.0 wt % of 4-tert-butylcyclohexyl acetate, about 6.0 wt % of 1,5-dimethyl-1-vinylhex-4-en-1-yl acetate, about 6.0 wt % of 3,7-dimethylocta-1,6-dien-3-ol, about 6.0 wt % of 1-(2,6,6-trimethylcyclohex-2-en-1-yl) pent-1-en-3-one, about 6.0 wt % of 2-isobutyl-4-methyltetrahydro-2H-pyran-4-ol, about 6.0 wt % of 1,4-dioxacycloheptadecane-5,17-dione, about 6.0 wt % of 2,6-dimethyloct-7-en-2-ol, about 2.0 wt % of 3-(4-isopropylphenyl)-2-methylpropanal, about 2.0 wt % of hexyl salicylate, about 1.4 wt % of 3-(4-ethylphenyl)-2,2-dimethylpropanal, about 0.6 wt % of 3-(2-ethylphenyl)-2,2-dimethylpropanal, about 2.0 wt % of 3a,4,5,6,7,7a-hexahydro-1H-4,7-methanoinden-6-yl acetate, about 2.0 wt % of Cedarwood oil, Virginian (*Juniperus virginiana* L.), about 1.0 wt % of 2-methylundecanal, about 0.8 wt % of (2,2-dimethoxyethyl) benzene, about 0.6 wt % of undec-10-enal, about 0.6 wt % of hex-3-en-1-ol, about 0.6 wt % of 3-(1,3-benzodioxol-5-yl)-2-methylpropanal, about 0.5 wt % of 1-phenylethyl acetate, about 0.4 wt % of 3a,6,6,9a-tetramethyldodecahydronaphtho[2,1-b] furan, about 0.4 wt % of allyl (3-methylbutoxy) acetate, and about 0.1 wt % of 1-(5,5-dimethylcyclohex-1-en-1-yl) pent-4-en-1-one, wherein the weight percentage of each compound is with reference to the total weight of the blend of the perfume raw materials. It is understood and one of ordinary skill in the art will appreciate that, if not clearly contradicted by the content of this specification, each of the one or more preceeding compounds can be combined with any of the embodiments hereinabove or hereinbelow, and in particular with any embodiment of a fragrance release modulator and/or features/elements disclosed as part of that embodiment.

In some embodiments of the present invention, a blend of perfume raw material, referred to herein from time to time as Fragrance "Floral Fresh" or Floral Fresh Fragrance, consists of the compounds listed in Table 8 at the indicated weight percentage.

Thus, a preferred blend of perfume raw materials of the present invention consists about 14.0 wt % of 1-(2,3,8,8-tetramethyl-1,2,3,4,5,6,7,8-octahydronaphthalen-2-yl) ethanone, about 12.0 wt % of methyl (3-oxo-2-pentylcyclopentyl) acetate, about 11.0 wt % of 2-benzylideneoctanal, about 6.0 wt % of 1-cedr-8-en-9-ylethanone, about 6.0 wt % of 4-tert-butylcyclohexyl acetate, about 6.0 wt % of 1,5-dimethyl-1-vinylhex-4-en-1-yl acetate, about 6.0 wt % of 3,7-dimethylocta-1,6-dien-3-ol, about 6.0 wt % of 1-(2,6,6-trimethylcyclohex-2-en-1-yl) pent-1-en-3-one, about 6.0 wt % of 2-isobutyl-4-methyltetrahydro-2H-pyran-4-ol, about 6.0 wt % of 1,4-dioxacycloheptadecane-5,17-dione, about 6.0 wt % of 2,6-dimethyloct-7-en-2-ol, about 2.0 wt % of 3-(4-isopropylphenyl)-2-methylpropanal, about 2.0 wt % of hexyl salicylate, about 1.4 wt % of 3-(4-ethylphenyl)-2,2-dimethylpropanal, about 0.6 wt % of 3-(2-ethylphenyl)-2,2-dimethylpropanal, about 2.0 wt % of 3a,4,5,6,7,7a-hexahydro-1H-4,7-methanoinden-6-yl acetate, about 2.0 wt % of Cedarwood oil, Virginian (*Juniperus virginiana* L.), about 1.0 wt % of 2-methylundecanal, about 0.8 wt % of (2,2-dimethoxyethyl) benzene, about 0.6 wt % of undec-10-enal, about 0.6 wt % of hex-3-en-1-ol, about 0.6 wt % of 3-(1,3-benzodioxol-5-yl)-2-methylpropanal, about 0.5 wt % of 1-phenylethyl acetate, about 0.4 wt % of 3a,6,6,9a-tetramethyldodecahydronaphtho[2,1-b] furan, about 0.4 wt % of allyl (3-methylbutoxy) acetate, and about 0.1 wt % of 1-(5,5-dimethylcyclohex-1-en-1-yl) pent-4-en-1-one, wherein the weight percentage of each compound is with reference to the total weight of the blend of the perfume raw materials. It is understood and one of ordinary skill in the art will appreciate that, if not clearly contradicted by the content of this specification, each of the one or more preceeding compounds can be combined with any of the embodiments hereinabove or hereinbelow, and in particular with any embodiment of a fragrance release modulator and/or features/elements disclosed as part of that embodiment.

Each of the perfume raw materials and each of the blends of perfume raw materials described herein can be combined with any of the solvents or diluents described herein. Each of the perfume raw materials and each of the blends of perfume raw materials described herein can be combined with any of the fragrance release modulators (FRMs) described herein. Each of the perfume raw materials and each of the blends of the perfume raw materials described herein can be combined with any of the solvents or diluents and fragrance release modulators described herein.

B. Fragrance Release Modulators (FRMs)

In some embodiments of the present invention, a freshening composition comprises a fragrance release modulator. In some embodiments of the present invention, an air freshening composition comprises a fragrance release modulator. In some embodiments of the present invention, a liquid freshening composition a fragrance release modulator. In some embodiments of the present invention, a clear freshening composition comprises a fragrance release modulator. In some embodiments of the present invention, a homogenous freshening composition comprises a fragrance release modulator. In some embodiments of the present invention, a clear liquid freshening composition comprises a fragrance release modulator. In some embodiments of the present invention, a liquid air freshening composition comprises a fragrance release modulator. In some embodiments of the present invention, a homogeneous clear liquid air freshening composition comprises a fragrance release modulator. In some embodiments of the present invention, a homogeneous clear liquid air freshening composition comprises a fragrance release modulator. Sometimes, herein a fragrance release modulator is referred to as "drop-in fragrance release modulator" or "drop-in FRM." It is understood and one of ordinary skill in the art will appreciate that, if not clearly contradicted by the content of this specification, each embodiment of a fragrance release modulator and/or features/elements disclosed as part of that embodiment can be combined with any of the embodiments hereinabove or hereinbelow.

Unexpectedly and surprisingly, the inventors have found that specific combinations of solvents, diluents, or solubilizers with a fragrance release modulator (FRM), permit the customization, control, and modulation of (i) the lifespan of a freshening composition and (ii) the releasing profile of the freshening composition. This customization, control and modulation can be achieved regardless of which wicking device used. For example, the wicking device is a reed or a plurality of reeds, a wick or a plurality of wicks, a stick or a plurality of sticks, a fiber or a plurality of fibers, a mesh, or a combination thereof, there is no need to intervene, no need to touch the delivery device or to reverse the flow of the freshening composition through the delivery device during product usage. Moreover, at the end of product usage the reservoir in the delivery device is substantially completely empty.

Further, and equally surprisingly and unexpectedly, the inventors have found that it will be possible to establish a two-stage functional regime and to customize, control and modulate the release of a freshening composition by controlling the transport process of the freshening composition inside of, e.g., a wicking system to an emanating surface by using a "drop-in" fragrance release modulator ("FRM"). More specifically, the inventors have found that by using the "drop-in" FRM it will be possible to alter, modulate, control and customize the surface tension, the dynamic viscosity and the density of such freshening composition. That discovery allows for the optimization, modulation and control of the mass transport of a freshening composition through a "delivery engine," such as a reed, a stick, a fiber, a mesh, a wick, a membrane, a porous or a semi-porous material. Thus, in some embodiments of the present invention, a fully saturated emanating surface is provided, whereby the lifespan of the air care product is optimized and controlled. Further, the strength, character and diffusivity of the scent irrespective of the perfume raw material used, can be optimized and controlled without altering the capability of the freshening composition to, e.g., address other functions, such as to counteract malodor ingredients or compositions or to have insect repelling activity.

Surprisingly and un-expectedly, the inventors have found that the mass transfer process of a freshening composition inside a wicking or diffusing element, as well as the mass transfer and the diffusion process of the freshening composition can be altered, modulated and controlled when specific materials, herein described as fragrance release modulators (FRM), are dropped into a perfume raw material or a blend of perfume raw materials—with or without a solvent or diluent—to formulate a freshening composition. The FRM can significantly influence the wicking process inside the delivery device (further described herein), and the releasing rate of the freshening composition at the surface of the emanating device by altering the surface tension, the dynamic viscosity, the density, the flash point and the volatility of the freshening composition. In other words, an FRM, as described herein, permits the control, the customization and the modulation of diffusivity and long-lasting characteristics of a freshening composition, including, but not limited to, the perceived scent's character, the intensity and lifespan of the product. Due to the presence of an FRM, a freshening composition can be released through a two-stage process: (i) an initial transitory regime, which is associated with unusually high amount of freshening composition release, and (ii) a steady-state release regime, which implies a linear release of the freshening composition into an external environment until, or very close to its full completion (see, Examples).

As described herein, a FRM helps to formulate long-lasting air freshening products with customized releasing time when the delivery device is a wicking or a diffusing device. There are no known formulation restrictions regarding the selection of perfume raw material, fragrance ingredients, flavor ingredients, essential oils, or functional ingredients that can be employed in combination with an FRM. Further, the inventors have not found any limitation with respect to the type of ingredient and the concentration of such ingredient when used in combination with an FRM.

By dropping the FRM into a freshening composition, which comprises a perfume raw material, the inventors surprisingly and unexpectedly have found that it is possible to control and customize (i) the surface tension of the freshening composition; (ii) the dynamic viscosity of the freshening composition; (iii) the density of the freshening composition; and (iv) the flash point of the freshening composition, all measured under normal temperature and pressure ("NTP") conditions. This finding permits the control of the two critical steps associated with the releasing process of the freshening compositions: (i) the capillary mass transfer of the freshening composition through the "delivery element", which can be a reed, stick, fiber, mesh, wick, semi-porous or porous materials; and (ii) the phase and mass transfer processes of the freshening composition at the emanating surface.

Freshening compositions of the present invention comprise specific amounts and compositions of FRM, depending on the desired application. FRMs generally are odorless or low-odor, non-fragrance materials, but fragrance-miscible compounds. They may be used in combination with any perfume raw material (PRM) described herein, i.e., in combination with one or more of an ester, an alcohol, an aldehyde, a ketone, an acetal, a phenol, an ether, a lactone, a furan, a hydrocarbon, an acid, a natural origin fragrance compound, stereoisomers, and mixtures thereof, without any restriction, and without any negative impact on the freshening competition's hedonic character and strength, as well as the freshening composition's targeting purpose.

In some embodiments of the present invention, a fragrance release modulator comprises one or more ingredients having almost no hedonic impact on a person's fragrance experience. Those ingredients permit emanating a surface to quickly saturate and to operate as a steady saturated surface during the delivery process of the freshening composition.

The inventors have found that FRMs described herein when combined with a perfume raw material to form a freshening composition bestow the desired and superior characteristics upon the freshening composition. The inventors have found the following FRMs most useful: $C_{2-8}$ linear and branched alcohols, alkyl- and aryl-ethers, alkyl- and aryl-glycols, alkyl- and aryl-carbonates, alkyldiols, alkyl- and aryl-adipates, alkyl- and aryl-benzoates, alkyl- and aryl-citrates, alkyl- and aryl-laurates, alkyl- and aryl-palmitates, alkyl- and aryl-stearates, aryl-myristates, alkyl- and aryl-succinates, alkyl- and aryl-glutarates, silicon solvents, combinations and mixtures thereof. Thus, in some embodiments of the present invention, a fragrance release modulator is selected from the group consisting of a $C_{2-8}$ linear alcohol, a $C_{2-8}$ branched alcohol, an alkyl-ether, an aryl-ether, an alkyl-glycol, an aryl-glycol, an alkyl-carbonate, an aryl-carbonate, an alkyldiol, an alkyl-adipate, an aryl-adipate, an alkyl-benzoate, an aryl-benzoate, an alkyl-citrate, an aryl-citrate, an alkyl-laurate, an aryl-laurate, an alkyl-palmitate, an aryl-palmitate, an alkyl-stearate, an aryl-stearate, an aryl-myristate, an alkyl-succinate, an aryl-succinate, an alkyl-glutarate, an aryl-glutarate, a silicon solvent a stereoisomer of any preceeding fragrance release modulator, and a mixture of any of the preceeding release modulators.

Preferred FRMs are ethanol, triethylcitrate, benzyl benzoate, 3-methoxy-3-methyl-1-butanol, 1,2 hexanediol, 1,2 pentanediol, hexyleneglycol, glycerol, propylene glycol, di-propylene glycol, dimethyl ether, isoamyl laurate, methyl palmitate, methyl stearate, dimethicone, disiloxane, trisiloxane, stereoisomers and mixtures thereof. Thus, in some embodiments of the present invention, a fragrance release modulator is selected from the group consisting of ethanol, triethylcitrate, benzyl benzoate, 3-methoxy-3-methyl-1-butanol, 1,2 hexanediol, 1,2 pentanediol, hexyleneglycol, glycerol, propylene glycol, di-propylene glycol, dimethyl ether, isoamyl laurate, methyl palmitate, methyl stearate, dimethicone, disiloxane, trisiloxane, a stereoisomer of any preceeding fragrance release modulator, and a mixture of any of the preceeding fragrance release modulators. Preferred are ethanol, triethylcitrate, benzyl benzoate, 3-methoxy-3-methyl-1-butanol, and di-propylene glycol. In some embodiments of the present invention, a fragrance release modulator is ethanol. Thus, in some embodiments of the present invention, a freshening composition comprises ethanol. In some embodiments of the present invention, a fragrance release modulator is triethylcitrate. Thus, in some embodiments of the present invention a freshening composition comprises triethylcitrate. In some embodiments of the present invention, a fragrance release modulator is benzyl benzoate. Thus, in some embodiments of the present invention a freshening composition comprises benzyl benzoate. In some embodiments of the present invention, a fragrance release modulator is 3-methoxy-3-methyl-1-butanol. Thus, in some embodiments of the present invention a freshening composition comprises 3-methoxy-3-methyl-1-butanol. In some embodiments of the present invention, a fragrance release modulator is di-propylene glycol. Thus, in some embodiments of the present invention a freshening composition comprises di-propylene glycol.

Other preferred FRMs are n-propanol, iso-propanol, n-butanol, t-butanol, 3-methoxy-3-methyl-1-butanol, 1-pentanol, 2-pentanol, amyl-alcohol, n-pentyl alcohol, 1,3 propanediol, 1,2 hexanediol, 1,2 pentanediol, dimethyl ether, propylene glycol, dipropylene glycol, hexyleneglycol, glycerol, benzyl benzoate, triethylcitrate, dioctyl adipate, propylene carbonate, dimethyl carbonate, isoamyl laurate, methyl palmitate, methyl stearate, dimethyl ether, dimethyl adipate, dimethyl succinate, dimethyl glutarate, n-butyl propionate, dimethicone, disiloxane, trisiloxane, stereoisomers or a combination thereof. Thus, in some embodiments of the present invention, a fragrance release modulator is selected from the group consisting of ethanol, n-propanol, iso-propanol, n-butanol, t-butanol, 3-methoxy-3-methyl-1-butanol, 1-pentanol, 2-pentanol, amyl-alcohol, n-pentyl alcohol, 1,3 propanediol, 1,2 hexanediol, 1,2 pentanediol, dimethyl ether, propylene glycol, dipropylene glycol, hexyleneglycol, glycerol, benzyl benzoate, triethylcitrate, dioctyl adipate, propylene carbonate, dimethyl carbonate, isoamyl laurate, methyl palmitate, methyl stearate, dimethyl ether, dimethyl adipate, dimethyl succinate, dimethyl glutarate, n-butyl propionate, dimethicone, disiloxane, trisiloxane, stereoisomers, and a mixture of any of the preceeding fragrance release modulators.

A preferred freshening composition of the present invention comprises less than about 90 wt % fragrance release modulator selected from the group consisting of ethanol, n-propanol, iso-propanol, n-butanol, t-butanol, 3-methoxy-3-methyl-1-butanol, 1-pentanol, 2-pentanol, amyl alcohol, n-pentyl alcohol, 1,3 propanediol, 1,2 hexanediol, 1,2 pentanediol, propylene glycol, dipropylene glycol, hexyleneglycol, glycerol, dimethyl ether, benzyl benzoate, triethylcitrate, dimethyl adipate, dioctyl adipate, propylene carbonate, dimethyl carbonate, isoamyl laurate, methyl palmitate, methyl stearate, dimethyl ether, dimethyl succinate, dimethyl glutarate, n-butyl propionate, dimethicone, disiloxane, trisiloxane, and a combination of any of the preceeding fragrance release modulators. Weight percentage is made with reference to the total weight of the freshening composition.

Fragrance release modulators of the present invention can be characterized by their flash point, surface tension, dynamic viscosity, density, and vapor pressure. For example, TEC has a flash point of greater than about 200° F., a surface tension of about 33.7 dyne/cm at 20° C., a dynamic viscosity of about 6.5 mPa·s at 20° C., a density of about 1,137 g/l at 20° C., and a vapor pressure of about 0.0006 mmHg at 25° C. As another example, BB has a flash point of greater than about 200° F. (298° F.), a surface tension of about 26.6 dyne/cm at 20° C., a dynamic viscosity of about 8.3 mPa·s at 25° C., a density of about 1,118 g/l at 25° C., and a vapor pressure of about 0.0002 mmHg at 25° C.

A preferred FRM of the present invention has a surface tension of less than about 60 mN/m; preferably, less than about 50 mN/m; more preferably, less than about 40 mN/m, and most preferably, less than about 30 mN/m.

A preferred FRM of the present invention has a dynamic viscosity in the range from about 0.5 cp to about 100 cp. A preferred FRM of the present invention has dynamic viscosity of less than about 100 cp, preferably, less than about 50 cp, more preferably, less than about 30 cp, even more preferably, less than about 20 cp, and most preferably, less than about 10 cp.

A preferred FRM of the present invention has a surface density in the range from about 100 g/l to about 2,000 g/l, preferably, in the range from about 200 g/l to about 1,800 g/l, more preferably, in the range from about 400 g/l to about 1,600 g/l, and most preferably, in the range from about 600 g/l to about 1,300 g/l. Another preferred FRM of the present invention has a surface density in the range between about 100 g/l and about 2,000 g/l; preferably, in the range between about 200 g/l and about 1,800 g/l, more preferably, in the range between about 400 g/l and about 1,600 g/l, and most preferably, in the range between about 600 g/l and about 1,300 g/l.

A freshening composition of the present invention may comprise a fragrance release modulator at a level of less than about 99 wt %, less than about 95 wt %, less than about 90 wt %, less than about 85 wt %, less than about 80 wt %, less than about 75 wt %, less than about 70 wt %, less than about 65 wt %, less than about 60 wt %, less than about 50 wt %, less than about 40 wt %, less than about 30 wt %, less than about 20 wt %, less than about 10 wt %, less than about 5 wt %, less than about 2 wt %, less than about 1 wt %, less than about 0.5 wt %, less than about 0.2 wt %, less than about 0.1 wt %, less than about 0.05%, less than about 0.02 wt %, or less than about 0.01 wt %, with the weight percentages being relative to the total weight of the freshening composition.

A freshening composition of the present invention may comprise a fragrance release modulator at a level of greater than about 0.01 wt %, greater than about 0.02 wt %, greater than about 0.05 wt %, greater than about 0.1 wt %, greater than about 0.2 wt %, greater than about 0.5 wt %, greater than about 1 wt %, greater than about 2 wt %, greater than about 5 wt %, greater than about 10 wt %, greater than about 20 wt %, greater than about 30 wt %, greater than about 40 wt %, greater than about 50 wt %, greater than about 60 wt %, greater than about 70 wt %, greater than about 80 wt %, greater than about 85 wt %, greater than about 90 wt %, greater than about 95 wt %, greater than about 99 wt %, with the weight percentages being relative to the total weight of the freshening composition.

A freshening composition of the present invention may comprise a fragrance release modulator in a range from about 0.01 wt % to about 99 wt %, in a range from about 0.02 wt % to about 95 wt %, in a range from about 0.05 wt % to about 95 wt %, in a range from about 0.1 wt % to about 95 wt %, in a range from about 0.2 wt % to about 95 wt %, in a range from about 0.5 wt % to about 95 wt %, in a range from about 1 wt % to about 95 wt %, in a range from about 2 wt % to about 90 wt %, in a range from about 3 wt % to about 85 wt %, in a range from about 5 wt % to about 80 wt %, in a range from about 10 wt % to about 75 wt %, in a range from about 15 wt % to about 70 wt %, in a range from about 20 wt % to about 65 wt %, in a range from about 25 wt % to about 60 wt %, in a range from about 30 wt % to about 55 wt %, in a range from about 40 wt % to about 50 wt %, with the weight percentages being relative to the total weight of the freshening composition.

A freshening composition of the present invention may comprise a fragrance release modulator in a range between about 0.01 wt % and about 99 wt %, in a range between about 0.02 wt % and about 95 wt %, in a range between about 0.05 wt % and about 95 wt %, in a range between about 0.1 wt % and about 95 wt %, in a range between about 0.2 wt % and about 95 wt %, in a range between about 0.5 wt % and about 95 wt %, in a range between about 1 wt % and about 95 wt %, in a range between about 2 wt % and about 90 wt %, in a range between about 3 wt % and about 85 wt %, in a range between about 5 wt % and about 80 wt %, in a range between about 10 wt % and about 75 wt %, in a range between about 15 wt % and about 70 wt %, in a range between about 20 wt % and about 65 wt %, in a range between about 25 wt % and about 60 wt %, in a range between about 30 wt % and about 55 wt %, in a range between about 40 wt % and about 50 wt %, with the weight percentages being relative to the total weight of the freshening composition.

Preferably, a freshening composition comprises from about 0.01 wt % to about 80 wt % fragrance release modulator (FRM); preferably, less than about 50 wt % FRM; more preferable, less than about 10 wt % FRM; and most preferable less than about 3 wt % FRM, with the weight percentages being relative to the total weight of the freshening composition.

C. Solvents and Diluents

In some embodiments of the present invention, a freshening composition comprises a perfume raw material and a solvent or diluent. In some embodiments of the present invention, an air freshening composition comprises a perfume raw material and a solvent or diluent. In some embodiments of the present invention, a liquid freshening composition comprises a perfume raw material and a solvent or diluent. In some embodiments of the present invention, a clear freshening composition comprises a perfume raw material and a solvent or diluent. In some embodiments of the present invention, a homogenous freshening composition comprises a perfume raw material and a solvent or diluent. In some embodiments of the present invention, a clear liquid freshening composition comprises a perfume raw material and a solvent or diluent. In some embodiments of the present invention, a liquid air freshening composition comprises a perfume raw material and a solvent or diluent. In some embodiments of the present invention, a homogeneous clear liquid air freshening composition comprises a perfume raw material and a solvent or diluent. In some embodiments of the present invention, a homogeneous clear liquid air freshening composition comprises a perfume raw material and a solvent or diluent. A solvent or diluent, from time to time, may also be referred to as solubilizer. It is understood and one of ordinary skill in the art will appreciate that, if not clearly contradicted by the content of this specification, each embodiment of a solvent, diluent, or solubilizer and/or features/elements disclosed as part of that embodiment can be combined with any of the embodiments hereinabove or hereinbelow.

In some embodiments of the present invention, a solvent is a volatile solvent. With a few exceptions, such as silicon fluids, most high volatile solvents are classified as volatile organic compounds (VOCs). In the United States, acceptable levels of VOC solvents in a final product is restricted by national organizations, such as the Environmental Protection Agency (EPA) or the California Air Resources Board (CARB). The present invention provides freshening compositions that are in compliance with requirements imposed by those agencies.

The inventors have established certain key performance requirements (KPRs) for a solvent to be used for the formulation of a liquid freshening composition as described herein, preferably, for the formulation of a freshening composition for use with a wicking delivery device. According to those KPRs, a preferred solvent is completely miscible with any perfume raw material described herein. A preferred solvent is odorless, or at least of low odor. Also, according to those KPRs, a preferred solvent easily wicks through a delivery device as described herein without clogging it. Another characteristic of a solvent for use in formulating a freshening composition is to easily diffuse from the emanating surface of a delivery device into an external environment, the atmosphere, air, or onto an external surface. Other preferred characteristics of a solvent include compliance with safety requirements, such as being CARB-accepted. Further, they should be cost effective, readily available, and preferably, sustainable.

Thus, one of ordinary skill in the art knows how to characterize solvents based on their polarities, volatilities, functionalities, flash points, densities, viscosities, and surface tensions. Those basic techniques are not set forth herein.

In some embodiments of the present invention, a carrier comprises a solvent, a diluent, and/or a solubilizer. A solvent can also function as a diluent. A solvent may also comprise or a blend of solvents with different polarities and volatilities, a functional perfume component, such as a malodor counteracting ingredient, or combinations thereof.

In some embodiments of the present invention, a solvent is a mixture of solvents.

A solvent or diluent for use in a freshening composition of the present invention excludes glycol ethers. Thus, a preferred solvent or diluent is a non-glycol solvent. An even more preferred solvent or diluent is a non-glycol ether solvent.

A preferred solvent or diluent includes, but is not limited to, 3-methyl-1,3-butanediol-1-acetate (IPD-AC® brand name from Kuraray), 2,2-dimethyl-1,3-dioxolane-4-methanol (Augeo Clean Multi® brand name from Solvay), dimethyl adipate (DMA), Isopar M® (trade name from ExxonMobil), dimethicone, disiloxane, trisiloxane, cyclosiloxane, and a combination of any of the preceeding solvents or diluents. Thus, in some embodiments of the present invention, a solvent or diluent is selected from the group consisting of 3-methyl-1,3-butanediol-1-acetate, 2,2-dimethyl-1,3-dioxolane-4-methanol, dimethyl adipate, Isopar M®, dimethicone, disiloxane, trisiloxane, cyclosiloxane, and a combination of any of the preceeding solvents or diluents. In some embodiments of the present invention, a solvent or diluent is selected from the group consisting of 2,2-dimethyl-1,3-dioxolane-4-methanol, 3-methyl-1,3-butanediol-1-acetate, dimethyl adipate, dimethicone, disiloxane, trisiloxane, a cyclosiloxane, Isopar M®, and a combination of any of the preceeding solvents or diluents. In some embodiments of the present invention, a solvent or diluent is selected from the group consisting of 2,2-dimethyl-1,3-dioxolane-4-methanol, 3-methyl-1,3-butanediol-1-acetate, dimethyl adipate, a $C_{15-19}$alkane, a $C_{13-19}$isoparaffine, an alkylcyclosiloxane, an aryl-cyclosiloxane, and a combination of any of the preceeding solvents or diluents.

Preferred $C_{15-19}$alkanes include, but are not limited to, Emogreen L-15® (European Community Number: 942-444-6; CAS Number: 68551-20-2; European REACh registration number: 01-2120107955-53) or Emogreen L-19® (European Community Number: 942-446-7; CAS Number: 90622-53-0; European REACh registration number: 01-2120107957-49), each of which is believed to be a mixture of different fractions.

Preferred $C_{13-19}$isoparaffines include, but are not limited to, Isopar M®, Isopar H® (CAS Number: 64742-49-9/90622-57-4), Isopar K® (CAS Number: 64742-48-9), and Isopar L® (CAS Number 64742-48-9), each of which is believed to be a mixture of different fractions In some embodiments of the present invention, a solvent or diluent is Augeo Clean Multi®. Augeo Clean Multi® is known as acetone monoglycerol ketal (CAS Number 100-79-8). It can be obtained from various sources, including Solvay (Vernon, Tex., USA).

In some embodiments of the present invention, a solvent or diluent is IPD-AC®. IPD-AC® is known as 3-methyl-1,3-butanediol-acetate (CAS Number 1609958-13-5). It can be obtained from various sources, including Kuraray America Inc., Kuraray America Chemicals Division (Houston, Tex., USA).

In some embodiments of the present invention, a solvent or diluent is STA-SOL® ESS 165. STA-SOL® ESS 165 is known as dimethyl adipate (synonyms: Hexanedioic acid, 1,6-dimethyl ester, Hexanedioic acid, dimethyl ester, Adipic acid, dimethyl ester). It can be obtained from various sources, including ST Laboratories, Inc. (Cranston, R.I., USA).

In some embodiments of the present invention, a solvent or diluent is VOLASIL® DM-2. VOLASIL® DM-2 is known as dimethicone. It can be obtained from various sources, including CHEMSIL Silicones, Inc. (Chatsworth, Calif., USA).

A freshening composition of the present invention may comprise a solvent or diluent at a level of less than about 90 wt %, less than about 80 wt %, less than about 70 wt %, less than about 60 wt %, less than about 50 wt %, less than about 40 wt %, less than about 30 wt %, less than about 20 wt %, less than about 10 wt %, less than about 5 wt %, less than about 2 wt %, or less than about 1 wt %, with the weight percentages being relative to the total weight of the freshening composition.

A freshening composition of the present invention may comprise a solvent or diluent at a level of greater than about 1 wt %, greater than about 2 wt %, greater than about 5 wt %, greater than about 10 wt %, greater than about 20 wt %, greater than about 30 wt %, greater than about 40 wt %, greater than about 50 wt %, greater than about 60 wt %, greater than about 70 wt %, greater than about 80 wt %, greater than about 90 wt %, with the weight percentages being relative to the total weight of the freshening composition.

A freshening composition of the present invention may comprise a solvent or diluent in a range from about 0.1 wt % to about 99 wt %, in a range from about 0.5 wt % to about 99 wt %, in a range from about 1 wt % to about 95 wt %, in a range from about 1 wt % to about 90 wt %, in a range from about 2 wt % to about 85 wt %, in a range from about 5 wt % to about 80 wt %, in a range from about 10 wt % to about 70 wt %, in a range from about 15 wt % to about 60 wt %, in a range from about 20 wt % to about 55 wt %, in a range from about 25 wt % to about 50 wt %, in a range from about 30 wt % to about 40 wt %, with the weight percentages being relative to the total weight of freshening composition.

A freshening composition of the present invention may comprise a solvent or diluent in a range between about 0.1 wt % and about 99 wt %, in a range between about 0.5 wt % and about 99 wt %, in a range between about 1 wt % and about 95 wt %, in a range between about 1 wt % and about 90 wt %, in a range between about 2 wt % and about 85 wt %, in a range between about 5 wt % and about 80 wt %, in a range between about 10 wt % and about 70 wt %, in a range between about 15 wt % and about 60 wt %, in a range between about 20 wt % and about 55 wt %, in a range between about 25 wt % and about 50 wt %, in a range between about 30 wt % and about 40 wt %, with the weight percentages being relative to the total weight of freshening composition

III. Air Care Products and Devices

The present invention also provides are care products and devices. It is understood and one of ordinary skill in the art will appreciate that, if not clearly contradicted by the content of this specification, each embodiment of an air care product or device and/or features/elements disclosed as part of that embodiment can be combined with any of the embodiments hereinabove or hereinbelow.

A freshening composition of the present invention may be used with an air care product or device to deliver volatile materials of a freshening composition, such as the scent of a freshening composition, into the atmosphere, into the air, or onto a surface. Thus, the present invention also provides air care products and devices for use with the freshening compositions described herein. It is contemplated that the air care product or device is configured for use in a variety of applications to deliver volatile materials of a freshening composition, such as the scent of a freshening composition, into the atmosphere, into the air, or onto a surface. The terms air care product, device and air freshener device are used interchangeably herein.

In some embodiments of the present invention, an air care product or a device comprises a freshening composition. In some embodiments of the present invention, an air care product or a device comprises a liquid freshening composition. In some embodiments of the present invention, an air care product or a device comprises a clear freshening composition. In some embodiments of the present invention, an air care product or a device comprises a homogeneous freshening composition. In some embodiments of the present invention, an air care product or a device comprises a clear liquid freshening composition. In some embodiments of the present invention, an air care product or a device comprises an air freshening composition. In some embodiments, an air care product or a device comprises a liquid air freshening composition. In some embodiments of the present invention, an air care product or a device comprises a clear liquid air freshening composition. In some embodiments of the present invention, an air care product or a device comprises a homogeneous liquid air freshening composition. In some embodiments of the present invention, an air care product or a device comprises a homogeneous clear liquid air freshening composition.

A freshening composition of the present invention may be combined with any air care product or device wherein the freshening composition may be used directly or after dilution with solvents or diluents.

A freshening composition of the present invention may be combined with any air care product or device adapted for use in a method of the present invention as further described herein.

As will be appreciated by one of skill in the art, the design of an air care product or device comprising a freshening composition of the present invention and for use in a method of the present invention is not limited. In some embodiments of the present invention, an air care product is selected from the group consisting of a spray, an energized air freshening delivery system and a passive delivery device.

In some embodiments of the present invention, an air care product or device comprises a delivery system, which is in communication or in contact with a freshening composition that is also present in such air care product or device. The delivery system then directly or indirectly permits the freshening composition to be released into the atmosphere, into the air, or onto a surface. A variety of suitable delivery systems are described herein.

In some embodiments of the present invention, an air care product or device comprises an evaporative assistance element which facilitates the evaporation, delivery, dispersion of a freshening composition that is also present in such air care product or device. A variety of suitable evaporative assistance elements, including, but not limited to, a heater, a fan, an agitator, and combinations thereof, are described herein.

Aside from the air care products and devices described herein, one of ordinary skill in the art will appreciate that other commercially available and/or described air care products and devices may be used in combination with a freshening composition of the present invention.

In some embodiments of the present invention, a freshening composition of the present invention resides within an air care product or device as described in published U.S. Pat. Appl. No. US2014/0157665 A1, which hereby is incorporated by this reference in its entirety for all purposes.

In some embodiments of the present invention, a freshening composition of the present invention resides within an air care product or device as described in published U.S. Pat. Appl. No. US2016/0089465 A1, which hereby is incorporated by this reference in its entirety for all purposes.

In some embodiments of the present invention, a freshening composition of the present invention resides within an air care product or device as described in published U.S. Pat. Appl. No. US2016/0367715 A1, which hereby is incorporated by this reference in its entirety for all purposes.

In some embodiments of the present invention, a freshening composition of the present invention resides within an air care product or device as described in published U.S. Pat. Appl. No. US2018/0008740 A1, which hereby is incorporated by this reference in its entirety for all purposes.

A. Air Care Products Comprising a Means for Delivering a Freshening Composition

The present invention also provides air care products comprising a means for delivering a freshening composition. It is understood and one of ordinary skill in the art will appreciate that, if not clearly contradicted by the content of this specification, each embodiment of an air care product comprising a means for delivering a freshening composition and/or features/elements disclosed as part of that embodiment can be combined with any of the embodiments hereinabove or hereinbelow.

In some embodiments of the present invention, an air care product or device comprising a freshening composition is adapted or configured to deliver the freshening composition, preferably to the atmosphere, air, and/or a surface. Such air care product or device may be configured in various ways. For example, the air care product may comprise a means for delivering a freshening composition. Means for delivering a freshening composition include, but are not limited to, an actuator attached to a spraying device, a releasing element in the form of a wick, a reed, a stick, a fiber, a mesh, a membrane, or a porous or semi-porous substrate, including a felt pad.

B. Reed Diffuser Air Freshener

In some embodiments, an air care product or device is a reed diffuser air freshener. It is understood and one of ordinary skill in the art will appreciate that, if not clearly contradicted by the content of this specification, each embodiment of a reed diffuser air freshener and/or features/elements disclosed as part of that embodiment can be combined with any of the embodiments hereinabove or hereinbelow.

A reed diffuser air freshener may be configured in various ways. In some embodiments, a reed diffuser air freshener comprises (i) an air freshening composition, (ii) a reservoir, container, or vessel, (iii) one or more reeds, and (iv) an opening for the one or more reeds. The reservoir (or container, vessel) has a functionality selected from the group consisting of accepting a freshening composition, receiving a freshening composition, holding a freshening composition, housing freshening composition and storing a freshening composition. They may be made of different materials, such as glass, ceramic, wood or metal. Further, size and shape of the reservoir, container, or vessel are not limited. Thus, they may be of different sizes and shapes. The one or more reeds can be of natural or synthetic materials.

C. Air Care Products and Devices Configured as Energized Devices

In some embodiments of the present invention, an air care product or device is configured as an energized device. It is understood and one of ordinary skill in the art will appreciate that, if not clearly contradicted by the content of this specification, each embodiment of an air care product or device configured as an energized device and/or features/elements disclosed as part of that embodiment can be combined with any of the embodiments hereinabove or hereinbelow.

Exemplary, non-limiting energized devices include an electrical device. The energized device may be an electrical wall plug-in, or a battery-operated air freshener. They may have a delivery engine such as a wick, which is in direct contact with a freshening composition, and which is used to transport the freshening composition to an emanating surface or into the air, where the freshening composition is released to an external environment.

In some embodiments of the present invention, an energized air freshening delivery system is electrically powered. In some embodiments of the present invention, an energized air freshening delivery system is selected from the group consisting of a fan-based diffuser, a liquid electric pluggable air freshener, and an electromechanical actuating diffuser.

In some embodiments, an energized device is a heating device, e.g. a device powered by a chemical reaction, such as a catalyst fuel system, a solar powered device, etc.

In some embodiments of the present invention, an energized device comprises a micro-fluidic die having either a heater(s) or piezo crystal(s) that are used to dispense droplets of the freshening composition into the air.

An exemplary and preferred energized device is an electrical wall plug-in air freshener. In some embodiments of the present invention, a wall plug-in air freshener comprises a housing. Such housing is connected to an electrical outlet by a plug that is directly or indirectly attached to the housing. The wall plug-in air freshener further comprises at least one reservoir for accepting, receiving, holding and/or storing a freshening composition until it is used up. The housing may serve as a holder for the reservoir(s) and any of the other components of the air freshener. In some embodiments of the present invention, a wall plug-in air freshener further comprises a delivery engine, e.g., in the form of a wick. In some embodiments of the present invention, a wall plug-in air freshener further comprises an evaporative assistance element, e.g., in the form of a heater for dispensing the volatile material.

While some air care products or devices having a single reservoir, a single evaporative assistance element, and a single delivery engine, one of ordinary skill in the art will appreciate that air care products or devices may comprise more than reservoir, more than one evaporative assistance element, and/or more than one delivery engine. In embodiments where an air care product or device comprises more than one reservoir, each reservoir may contain a different freshening composition or may contain the same freshening composition.

D. Air Care Product and Devices Comprising a Wick

In some embodiments, an air care product or device comprises a means for delivering a freshening composition in the form of a wick. It is understood and one of ordinary skill in the art will appreciate that, if not clearly contradicted by the content of this specification, each embodiment of an air care product or device comprising a wick and/or features/elements disclosed as part of that embodiment can be combined with any of the embodiments hereinabove or hereinbelow.

A wick may be configured and be manufactured from different materials. Those materials can be natural or synthetic. They may have different porosities, various different shapes, and sizes. Exemplary, non-limiting wicks include, a wick having a cylindrical form or a wick having an elongate cube shape. Further, a wick may be characterized by its porosity, length, diameter, or width depending on its shape. As will be appreciated by one of ordinary skill in the art, wick porosity and the material of which it is made are critical parameters that influence the capillary diffusion process of a freshening composition. The length of a wick is not limiting. In some embodiments of the present invention, the length of a preferred wick ranges from about 1 millimeter ("mm") to about 100 mm, from about 5 mm to about 75 mm, or from about 10 mm to about 50 mm. In some embodiments of the present invention, the length of a preferred wick is between about 1 millimeter ("mm") and about 100 mm, between about 5 mm and about 75 mm, or between about 10 mm and about 50 mm. Similarly, the diameter or width of a wick is not limiting. In some embodiments, a preferred wick has a diameter of at least about 1 mm, of at least about 2 mm, of at least about 3 mm, or of at least about 4 mm. In some embodiments, a preferred wick has a width of at least about 1 mm, of at least about 2 mm, of at least about 3 mm, or of at least about 4 mm.

A wick exhibits a density and porosity. Density and porosity of a wick are not critical. In some embodiments of the present invention, the density of a preferred wick ranges from about 0.100 grams/cm$^3$ ("g/cc") to about 1.0 g/cc. In some embodiments of the present invention, the porosity of a preferred wick may be in the range from about 0.35 g/cc to about 0.85 g/cc. In some embodiments of the present invention, the density of a preferred wick is between about 0.100 grams/cm$^3$ ("g/cc") and about 1.0 g/cc. In some embodiments of the present invention, the porosity of a preferred wick is between about 0.35 g/cc and about 0.85 g/cc.

In some embodiments of the present invention, a wick comprises a porous or semi-porous substrate. A wick may comprise various materials and may be manufactured by various methods of construction, including, but not limited to, bundled fibers that may be compressed and/or formed into various shapes via overwrap (such as a non-woven sheet overwrap) or be made of sintered plastics such as poly ethylene (PE), high-density polyethylene (HDPE) or other polyolefins. For example, a wick may be made from a plastic material, such as polyethylene or a polyethylene blend.

In some embodiments of the present invention, an air care product or device is a passive diffuser that is not electrically powered. In some embodiments of the present invention, a passive diffuser is a passive air diffuser apparatus. A passive air diffuser apparatus can comprise a breathable membrane for diffusing and evaporating a freshening composition.

In some embodiments of the present invention, a passive diffuser is a wicking air freshener. In some embodiments of the present invention, a wicking air freshener is selected from the group consisting of a reed diffuser, a steam-based freshener, and a membrane-based air freshener. A preferred membrane-based air freshener is a car vent air freshener.

E. Air Care Product and Devices Comprising an Evaporative Surface

Air care products and devices of the present invention typically comprise an evaporative surface with which a freshening composition comes into contact. It is understood and one of ordinary skill in the art will appreciate that, if not clearly contradicted by the content of this specification, each embodiment of a an air care product or device comprising an evaporative surface and/or features/elements disclosed as part of that embodiment can be combined with any of the embodiments hereinabove or hereinbelow.

In some embodiments of the present invention, an evaporative surface may be integral or separate from an evaporative assistance element and/or the delivery engine. The evaporative surface may be configured as a porous or semi-porous substrate, a bowl or plate. That substrate, bowl or plate can be made of plastic, of glass, of metal or of a combination of any of the preceeding.

In some embodiments of the present invention, an air care product or device comprises an evaporative assistance element. An evaporative assistance element may be used to achieve or facilitate the evaporation of a freshening composition from the air care product. Such an evaporative assistance element may be configured in various ways. In some embodiments of the present invention, an evaporative assistance element is selected from the group consisting of a heater, a fan, an agitation member, a powered agitator, a manual agitator, and a combination thereof.

In some embodiments of the present invention, an evaporative assistance element is a heater comprising one or more heating elements. Such one or more heating elements may be used to heat a liquid volatile freshening composition within an air care product. A heater may be configured to heat the delivery system to a desired temperature. A preferred temperature is in the range from about 45° C. to about 75° C.

In some embodiments of the present invention, an evaporative assistance element comprises a chemical constituent. Such chemical constituent may be used to speed up evaporation or release rates of the freshening composition. In some embodiments of the present invention, an evaporative assistance element comprises a chemically heated membrane. Such chemically heated membrane may be used to provide increased evaporation of a freshening composition via exothermic reaction. As one of skill in the art will appreciate, synergistic combinations of a heating element, chemical constituent or chemically heated membrane may be used as well.

An energized device having an evaporative assistance element in the form of a heater may be configured to heat the delivery engine to various temperatures. For example, the energized device may be configured such that the heater heats an evaporative surface, such as a wick, membrane, gel, porous or semi-porous substrate, such as a felt pad, to a temperature from about 30° C. to about 150° C. A preferred energized device comprises a control system such that the heater temperature is adjustable. In some embodiments of the present invention, a control system also cycles the heater temperature to provide greater control over the evaporation process of the freshening composition.

III. Methods

In some embodiments, the present invention provides methods for formulating a freshening composition, methods for manufacturing an air care product or device comprising a freshening composition, methods for using a freshening composition, methods for using an air care product or device comprising a freshening composition to deliver the freshening composition, and methods for modulating the release and evaporation of a freshening composition.

A. Methods for Manufacturing a Freshening Composition

The present invention also provides methods for manufacturing a freshening composition. It is understood and one of ordinary skill in the art will appreciate that, if not clearly contradicted by the content of this specification, each embodiment of a method for manufacturing a freshening composition and/or features/elements disclosed as part of that embodiment can be combined with any of the embodiments hereinabove or hereinbelow.

Freshening compositions of the present invention can be manufactured without any further guidance, other than this disclosure, by one of ordinary skill in the art. As such, the present invention provides a method for manufacturing a freshening composition. The steps for manufacturing a freshening composition, described in detail below, can be performed in any order, consecutively, or contemporaneously.

In some embodiments of a method for manufacturing a freshening composition, the method comprises the step of adding a perfume raw material to a solvent or diluent. As one of ordinary skill in the art will appreciate, the step of adding one ingredient or component to another is synonymous with the step of combining one ingredient or component with another.

In some embodiments of a method for manufacturing a freshening composition, the method comprises the step of adding a solvent or diluent to a perfume raw material.

In some embodiments of a method for manufacturing a freshening composition, the method comprises the step of adding a fragrance release modulator to a solvent or diluent.

In some embodiments of a method for manufacturing a freshening composition, the method comprises the step of adding a solvent or diluent to a fragrance release modulator.

In some embodiments of a method for manufacturing a freshening composition, the method comprises the step of adding a perfume raw material to a fragrance release modulator to formulate a first mixture. The method further comprises the step of adding a solvent or diluent to the first mixture to formulate a second mixture.

Alternatively, in some embodiments of a method for manufacturing a freshening composition, the method comprises the step of adding a perfume raw material to a solvent or diluent to formulate a first mixture. The method then further comprises the step of adding a fragrance release modulator to the first mixture to formulate a second mixture.

In some embodiments of a method for manufacturing a freshening composition, the method comprises the step of combining one or more perfume raw materials. Thus, in some embodiments of a method for manufacturing a freshening composition, the method comprises the step of adding a first perfume raw material to a second perfume raw material. In some embodiments of a method for manufacturing a freshening composition, the method comprises the step of adding a perfume raw material to a plurality of different perfume raw materials.

In some embodiments of a method for manufacturing a freshening composition, the method comprises the step of combining one or more fragrance release modulators. Thus, in some embodiments of a method for manufacturing a freshening composition, the method comprises the step of adding a first fragrance release modulator to a second fragrance release modulator. In some embodiments of a method for manufacturing a freshening composition, the method comprises the step of adding a fragrance release modulator to a plurality of different fragrance release modulators.

In some embodiments of a method for manufacturing a freshening composition, the method comprises the step of combining one or more solvents or one or more diluents. Thus, in some embodiments of a method for manufacturing a freshening composition, the method comprises the step of adding a first solvent or diluent to a second solvent or diluent. In some embodiments of a method for manufacturing a freshening composition, the method comprises the step of adding a solvent or diluent to a plurality of different solvents or diluents.

In embodiments of the present invention, wherein a perfume raw material is a solid material, it may be first combined with a solvent or diluent that has the capability of solubilizing said solid perfume raw material. In those circumstances, a solvent or diluent may also be described as solubilizer.

In some embodiments of the present invention, a method for manufacturing a freshening composition comprises the step of combining (i) about 0.1 wt % to 95 wt % perfume raw material, the perfume raw material comprising one or more ingredients selected from the group consisting of an ester, an alcohol, an aldehyde, a ketone, an acetal, a phenol, an ether, a lactone, a furan, a hydrocarbon, an acid, a natural origin fragrance compound a stereoisomer of any preceeding perfume raw material, and a mixture of any preceeding perfume raw material, (ii) from about 1.0 wt % to about 95 wt % of a non-glycol ether solvent, a non-glycol ether diluent, or a mixture thereof; and (iii) from about 0.01 wt % to about 90 wt % fragrance release modulator having one or more characteristics selected from the group consisting of: (a) a flash point higher than about 100° F., (b) a surface tension of less than about 60 mN/m, (c) a dynamic viscosity from about 0.5 cp to about 100 cp, and (d) a density from about 600 g/l to about 1,300 g/l; wherein the fragrance release modulator is selected from the group consisting of a $C_{2-8}$ linear alcohol, a $C_{2-8}$ branched alcohol, an alkyl-ether, an aryl-ether, an alkyl-glycol, an aryl-glycol, an alkyl-carbonate, an aryl-carbonate, an alkyldiol, an alkyl-adipate, an aryl-adipate, an alkyl-benzoate, an aryl-benzoate, an alkyl-citrate, an aryl-citrate, an alkyl-laurate, an aryl-laurate, an alkyl-palmitate, an aryl-palmitate, an alkyl-stearate, an aryl-stearate, an aryl-myristate, an alkyl-succinate, an aryl-succinate, an alkyl-glutarate, an aryl-glutarate, a silicon solvent, a stereoisomer of any preceeding fragrance release modulator, and a mixture of any of the preceeding fragrance release modulators; thereby producing a mixture comprising (i), (ii), and (iii).

In some embodiments of the present invention, a method for manufacturing a freshening composition comprises the step adapting a freshening composition to have one or more of a characteristic selected from the group consisting of a flash point higher than about 100° F., a surface tension from about 10 mN/m to about 40 mN/m, a dynamic viscosity from about 1 cp to about 30 cp, and a density from about 650 g/l to about 1,300 g/l.

In some embodiments of a method for manufacturing a freshening composition, a perfume raw material comprises a plurality of perfume raw materials.

In some embodiments of a method for manufacturing a freshening composition, a non-glycol ether solvent is selected from the group consisting of an alkyladipate, an aryladipate, an alkyl-glycerol, an aryl-glycerol, an alkyldiol, and aryldiol, an isoparaffine, a silicon, and a mixture of any of the preceeding non-glycol ether solvents.

In some embodiments of a method for manufacturing a freshening composition, a non-glycol ether solvent is selected from the group consisting of 2,2-dimethyl-1,3-dioxolane-4-methanol, 3-methyl-1,3-butanediol-1-acetate, dimethyl adipate, dimethicone, disiloxane, trisiloxane, a $C_{15-19}$alkane, a $C_{13-19}$isoparaffine, a cyclosiloxane, Isopar M®, an alkylcyclosiloxane, an aryl-cyclosiloxane, and a combination of any of the preceeding non-glycol ether solvents.

In some embodiments of a method for manufacturing a freshening composition, a the fragrance release modulator is selected from the group consisting of ethanol, n-propanol, iso-propanol, n-butanol, t-butanol, 3-methoxy-3-methyl-1-butanol, 1-pentanol, 2-pentanol, amyl-alcohol, n-pentyl alcohol, 1,3 propanediol, 1,2 hexanediol, 1,2 pentanediol, dimethyl ether, propylene glycol, dipropylene glycol, hexyleneglycol, glycerol, benzyl benzoate, triethylcitrate, dioctyl adipate, propylene carbonate, dimethyl carbonate, iso-amyl laurate, methyl palmitate, methyl stearate, dimethyl ether, dimethyl adipate, dimethyl succinate, dimethyl glutarate, n-butyl propionate, dimethicone, disiloxane, trisiloxane, and a mixture of any of the preceeding fragrance release modulators.

In some embodiments of a method for manufacturing a freshening composition, the method further comprises the step of adding to the mixture comprising (i), (ii) and (iii) less than 50 wt % of an ingredient having a functional activity and wherein the ingredient having the functional activity is selected from the group consisting of an ingredient having malodor counteracting activity, an ingredient having antimicrobial activity, an ingredient having an insect repellant activity, an ingredient having a preservative activity, an ingredient having an antioxidant activity, an ingredient having a humectant activity, an ingredient having a UV-blocking activity, an ingredient having a pigment activity, an ingredient having a dye activity, an ingredient having a surfactant activity, an ingredient having an emulsifier activity, an ingredient having a solubilizer activity, an ingredient having a polymer activity, and an ingredient having a buffer activity.

In some embodiments of a method for manufacturing a freshening composition, the method further comprises the step of adding to the mixture comprising (i), (ii) and (iii) less than 50 wt % of an ingredient having a functional activity and wherein the ingredient having the functional activity is selected from the group consisting of an ingredient having malodor counteracting activity, an ingredient having antimicrobial activity, an insect repellant, a preservative, an antioxidant, a humectant, a UV-blocking agent, a pigment, a dye, a surfactant, an emulsifier, a solubilizer, a polymer, and a buffer.

In some embodiments of a method for manufacturing a freshening composition, a non-glycol ether solvent is selected from the group consisting of 2,2-dimethyl-1,3-dioxolane-4-methanol, 3-methyl-1,3-butanediol-1-acetate, dimethyl adipate, dimethicone, disiloxane, trisiloxane, a $C_{15-19}$alkane, a $C_{13-19}$isoparaffine, a cyclosiloxane, Isopar M®, an alkylcyclosiloxane, an aryl-cyclosiloxane, and a combination of any of the preceeding non-glycol ether solvents.

In some embodiments of a method for manufacturing a freshening composition, the method further comprises the step of adding to the mixture comprising (i), (ii) and (iii) less than about 20 wt % of an ingredient having a functional activity and wherein the ingredient having the functional activity is selected from the group consisting of an ingredient having malodor counteracting activity, an ingredient having antimicrobial activity, an ingredient having an insect repellant activity, an ingredient having a preservative activity, an ingredient having an antioxidant activity, an ingredient having a humectant activity, an ingredient having a UV-blocking activity, an ingredient having a pigment activity, an ingredient having a dye activity, an ingredient having a surfactant activity, an ingredient having an emulsifier activity, an ingredient having a solubilizer activity, an ingredient having a polymer activity, and an ingredient having a buffer activity.

In some embodiments of a method for manufacturing a freshening composition, the method further comprises the step of adding to the mixture comprising (i), (ii) and (iii) less than about 20 wt % of an ingredient having a functional activity and wherein the ingredient having the functional activity is selected from the group consisting of an ingredient having malodor counteracting activity, an ingredient having antimicrobial activity, an insect repellant, a preservative, an antioxidant, a humectant, a UV-blocking agent, a pigment, a dye, a surfactant, an emulsifier, a solubilizer, a polymer, and a buffer.

B. Methods for Manufacturing an Air Care Product or Device Comprising a Freshening Composition The present invention also provides methods for manufacturing an air care product or device comprising a freshening composition. It is understood and one of ordinary skill in the art will appreciate that, if not clearly contradicted by the content of this specification, each embodiment of a method for manufacturing an air care product or device comprising a freshening composition and/or features/elements disclosed as part of that embodiment can be combined with any of the embodiments hereinabove or hereinbelow.

Freshening compositions of the present invention may be introduced into an article or device, without any further guidance, other than this disclosure. Thus, one of ordinary skill in the art using this specification will be able to manufacture an article or device comprising a freshening composition of the present invention. As such, the present invention provides a method for manufacturing an article, an air care product, a device, or an air freshener device comprising a freshening composition.

Freshening compositions of the present invention may be used in a variety of forms to manufacture an article or a product comprising such freshening composition. For example, freshening compositions of the present invention may be directly used to manufacture sprayable, capillary wicking, membrane diffusing and/or steam-diffusing products or articles.

In some embodiments of a method for manufacturing an article, an air care product, a device, or an air freshener device comprising a freshening composition, the method comprises the step of introducing a freshening composition into an article, air care product, device or air freshening device. Any article, air care product, device or air freshener device described herein and or known to one of ordinary skill in the art may be used to introduce a freshening composition. Preferably, such article, air care product, device or air freshener device comprises a reservoir having a functionality selected from the group consisting of accepting a freshening composition, receiving a freshening composition, holding a freshening composition, housing freshening composition and storing a freshening composition.

In some embodiments of the present invention, an article, air care product, device or air freshener device comprises a delivery system. Suitable delivery systems are described herein. In some embodiments of the present invention, a delivery system is selected from the group consisting of a wick, a plurality of wicks, a stick, a plurality of sticks, a reed, a plurality of reeds, a fiber, a plurality of fibers, a mesh, a conductive mesh, a membrane, a porous substrate, a semi-porous substrate, and a combination of any of the preceeding delivery systems.

In some embodiments of a method for manufacturing an air care product, device or air freshener device comprising a freshening composition, the method comprises the step of introducing a freshening composition into a reservoir residing in an energized device. Suitable energized devices, such as an electric device (wall plug-in or battery-operated), are described herein.

In some embodiments of a method for manufacturing an air care product, device or air freshener device comprising a freshening composition, the method comprises the step of introducing a freshening composition into a reservoir residing in a heating device. Suitable heating devices are described herein.

In some embodiments of a method for manufacturing an air care product, device or air freshener device comprising a freshening composition, the method comprises the step of introducing a freshening composition into a reservoir residing in a device powered by a chemical reaction. Suitable devices powered by chemical reactions are described herein.

In some embodiments of a method for manufacturing an air care product, device or air freshener device comprising a freshening composition, the method comprises the step of introducing a freshening composition into a reservoir residing in a passive air diffuser apparatus. Suitable passive air diffuser apparatuses are described herein.

In some embodiments of a method for manufacturing an air freshener device comprising a freshening composition, the method comprises the step of contacting a reservoir in an air freshener device with a freshening composition, wherein the freshening composition comprises (i) from about 0.1 wt % to about 95 wt % perfume raw material, the perfume raw material comprising one or more ingredients selected from the group consisting of an ester, an alcohol, an aldehyde, a ketone, an acetal, a phenol, an ether, a lactone, a furan, a hydrocarbon, an acid, a natural origin fragrance compound, a stereoisomer of any preceeding perfume raw material, and a mixture of any of the preceeding perfume raw materials, (ii) from about 1.0 wt % to about 95 wt % of a non-glycol ether solvent, a non-glycol ether diluent, or a mixture thereof; and (iii) from about 0.01 wt % to about 90 wt % fragrance release modulator having one or more characteristics selected from the group consisting of (a) a flash point higher than about 100° F., (b) a surface tension of less than about 60 mN/m, (c) a dynamic viscosity from about 0.5 cp to about 100 cp, and (d) a density from about 600 g/l to about 1,300 g/l; wherein the fragrance release modulator is selected from the group consisting of a $C_{2-8}$ linear alcohol, a $C_{2-8}$ branched alcohol, an alkyl-ether, an aryl-ether, an alkyl-glycol, an aryl-glycol, an alkyl-carbonate, an aryl-carbonate, an alkyldiol, an alkyl-adipate, an aryl-adipate, an alkyl-benzoate, an aryl-benzoate, an alkyl-citrate, an aryl-citrate, an alkyl-laurate, an aryl-laurate, an alkyl-palmitate, an aryl-palmitate, an alkyl-stearate, an aryl-stearate, an aryl-myristate, an alkyl-succinate, an aryl-succinate, an alkyl-glutarate, an aryl-glutarate, a silicon solvent, a stereoisomer of any preceeding fragrance release modulator, and a mixture of any of the preceeding fragrance release modulators.

In some embodiments of a method for manufacturing an air freshener device comprising a freshening composition, the freshening composition is adapted to have one or more of a characteristic selected from the group consisting of (a) a flash point higher than about 100° F., (b) a surface tension from about 10 mN/m to about 40 mN/m, (c) a dynamic viscosity from about 1 cp to about 30 cp, and (d) a density from about 650 g/l to about 1,300 g/l.

In some embodiments of a method for manufacturing an air freshener device comprising a freshening composition, a perfume raw material comprises a plurality of perfume raw materials.

In some embodiments of a method for manufacturing an air freshener device comprising a freshening composition, a non-glycol ether solvent is selected from the group consisting of an alkyladipate, an aryladipate, an alkyl-glycerol, an aryl-glycerol, an alkyldiol, and aryldiol, an isoparaffine, a silicon, and a mixture of any of the preceeding non-glycol ether solvents.

In some embodiments of a method for manufacturing an air freshener device comprising a freshening composition, a non-glycol ether solvent is selected from the group consisting of 2,2-dimethyl-1,3-dioxolane-4-methanol, 3-methyl-1,3-butanediol-1-acetate, dimethyl adipate, dimethicone, disiloxane, trisiloxane, a $C_{15-19}$alkane, a $C_{13-19}$isoparaffine, a cyclosiloxane, Isopar M®, an alkylcyclosiloxane, an aryl-cyclosiloxane, and a combination of any of the preceeding non-glycol ether solvents.

In some embodiments of a method for manufacturing an air freshener device comprising a freshening composition, a fragrance release modulator is selected from the group consisting of ethanol, n-propanol, iso-propanol, n-butanol, t-butanol, 3-methoxy-3-methyl-1-butanol, 1-pentanol, 2-pentanol, amyl-alcohol, n-pentyl alcohol, 1,3 propanediol, 1,2 hexanediol, 1,2 pentanediol, dimethyl ether, propylene glycol, dipropylene glycol, hexyleneglycol, glycerol, benzyl benzoate, triethylcitrate, dioctyl adipate, propylene carbonate, dimethyl carbonate, isoamyl laurate, methyl palmitate, methyl stearate, dimethyl ether, dimethyl adipate, dimethyl succinate, dimethyl glutarate, n-butyl propionate, dimethicone, disiloxane, trisiloxane, and a mixture of any of the preceeding fragrance release modulators.

In some embodiments of a method for manufacturing an air freshener device comprising a freshening composition, a freshening composition further comprises less than 50 wt % of an ingredient having a functional activity and wherein the ingredient having the functional activity is selected from the group consisting of an ingredient having malodor counter-acting activity, an ingredient having antimicrobial activity, an ingredient having an insect repellant activity, an ingredient having a preservative activity, an ingredient having an antioxidant activity, an ingredient having a humectant activity, an ingredient having a UV-blocking activity, an ingredient having a pigment activity, an ingredient having a dye activity, an ingredient having a surfactant activity, an ingredient having an emulsifier activity, an ingredient having a solubilizer activity, an ingredient having a polymer activity, and an ingredient having a buffer activity.

In some embodiments of a method for manufacturing an air freshener device comprising a freshening composition, a freshening composition further comprises less than 50 wt % of an ingredient having a functional activity and wherein the ingredient having the functional activity is selected from the group consisting of an ingredient having malodor counter-acting activity, an ingredient having antimicrobial activity, an insect repellant, a preservative, an antioxidant, a humectant, a UV-blocking agent, a pigment, a dye, a surfactant, an emulsifier, a solubilizer, a polymer, and a buffer.

In some embodiments of a method for manufacturing an air freshener device comprising a freshening composition, a freshening composition comprises less than 20 wt % of an ingredient having a functional activity and wherein the ingredient having the functional activity is selected from the group consisting of an ingredient having malodor counteracting activity, an ingredient having antimicrobial activity, an ingredient having an insect repellant activity, an ingredient having a preservative activity, an ingredient having an antioxidant activity, an ingredient having a humectant activity, an ingredient having a UV-blocking activity, an ingredient having a pigment activity, an ingredient having a dye activity, an ingredient having a surfactant activity, an ingredient having an emulsifier activity, an ingredient having a solubilizer activity, an ingredient having a polymer activity, and an ingredient having a buffer activity.

In some embodiments of a method for manufacturing an air freshener device comprising a freshening composition, a freshening composition comprises less than 20 wt % of an ingredient having a functional activity and wherein the ingredient having the functional activity is selected from the group consisting of an ingredient having malodor counteracting activity, an ingredient having antimicrobial activity, an insect repellant, a preservative, an antioxidant, a humectant, a UV-blocking agent, a pigment, a dye, a surfactant, an emulsifier, a solubilizer, a polymer, and a buffer.

In some embodiments of a method for manufacturing an air freshener device comprising a freshening composition, an air freshener device further comprises a delivery system, wherein the delivery system comprises an element in communication or in contact with the freshening composition. In some embodiments of the present invention, the delivery system is selected from the group consisting of a reed, a plurality of reeds, a stick, a plurality of sticks, a fiber, a plurality of fibers, a wick, a plurality of wicks, a mesh material, a conductive mesh material, a porous substrate, a semi-porous substrate, and a combination of any of the preceeding delivery systems.

In some embodiments of a method for manufacturing an air freshener device comprising a freshening composition, an air freshener device comprises a reservoir having a functionality selected from the group consisting of accepting a freshening composition, receiving a freshening composition, holding a freshening composition, housing a freshening composition and storing a freshening composition. In some embodiments of the present invention, the reservoir is selected from the group consisting of a bottle, a vessel, and a container.

In some embodiments of a method for manufacturing an air freshener device comprising a freshening composition, an air freshener device comprises an evaporative assistance element. In some embodiments of the present invention, the evaporative assistance element is selected from the group consisting of a heater, a fan, an agitator, and a combination of any of the preceeding evaporative assistance elements.

In some embodiments of a method for manufacturing an air freshener device comprising a freshening composition, an air freshener device comprises an evaporative assistance element and a delivery system. In some embodiments of the present invention, the evaporative assistance element is a heater and wherein the heater is configured to heat the delivery system to a temperature in the range from about 45° C. to about 75° C.

C. Methods for Delivering a Smell or Scent of a Freshening Composition

The present invention also provides methods for delivering a smell or scent of a freshening composition. It is understood and one of ordinary skill in the art will appreciate that, if not clearly contradicted by the content of this specification, each embodiment of a method for delivering a smell or scent of a freshening composition and/or features/elements disclosed as part of that embodiment can be combined with any of the embodiments hereinabove or hereinbelow.

Freshening compositions of the present invention, preferably, the smell or scent of a freshening composition of the present invention, or a component thereof, may be delivered into the atmosphere, air and/or onto a surface, without any further guidance, other than this disclosure, by one of ordinary skill in the art. As such, the present invention provides a method for delivering a freshening composition or a component thereof, preferably, the smell or scent of a freshening composition or a component thereof, into the atmosphere, air, and/or onto a surface. By delivering a freshening composition or a component thereof, preferably, the smell or scent of a freshening composition or a component thereof, into the atmosphere, air, and/or onto a surface, the atmosphere, air and/or surface is refreshed. By delivering a freshening composition or a component thereof, preferably, the smell or scent of a freshening composition or a component thereof, into the atmosphere, air, and/or onto a surface, any malodor in the atmosphere, air and/or on the surface is reduced.

In some embodiments of a method for delivering a freshening composition or a component thereof, preferably, the smell or scent of a freshening composition or a component thereof, into the atmosphere, air, and/or onto a surface, the method comprises the step of delivering the freshening composition or a component thereof, preferably, a liquid freshening composition or a component thereof to a delivery system within an air care product or device. Suitable delivery systems are described herein.

In some embodiments of a method for delivering a freshening composition or a component thereof, preferably, the smell or scent of a freshening composition or a component thereof, into the atmosphere, air, and/or onto a surface, the delivery system may be heated to a temperature in the range from about 45° C. to about 75° C.

In some embodiments of a method for delivering a freshening composition or a component thereof, preferably, the smell or scent of a freshening composition or a component thereof, into the atmosphere, air, and/or onto a surface, the method comprises the step of dispersing the freshening composition or a component thereof, preferably, a liquid freshening composition or a component thereof into the atmosphere, air, and/or onto a surface.

In some embodiments of a method for delivering a freshening composition or a component thereof, preferably, the smell or scent of a freshening composition or a component thereof, into the atmosphere, air, and/or onto a surface, the method comprises the step of dispersing the freshening composition or a component thereof, preferably, a liquid freshening composition or a component thereof into the atmosphere, air, and/or onto a surface over a controlled or customized period of time.

In some embodiments, the step of dispersing a freshening composition or a component thereof, preferably, a liquid freshening composition or a component thereof into the atmosphere, air, and/or onto a surface, comprises wickening and evaporating the liquid freshening composition or a component thereof into the atmosphere, the air, and/or onto the surface. In some embodiments, the step of dispersing a freshening composition or a component thereof, preferably, a liquid freshening composition or a component thereof into the atmosphere, air, and/or onto a surface, comprises a wicking-evaporation system adapted to deliver the liquid freshening composition or a component thereof into the atmosphere, the air, and/or onto the surface. In some embodiments, the step of dispersing a freshening composition or a component thereof, preferably, a liquid freshening composition or a component thereof into the atmosphere, air, and/or onto a surface, comprises a wicking-evaporation system adapted to deliver the liquid freshening composition or a component thereof into the atmosphere, the air, and/or onto the surface, over a controlled or customized period of time. A variety of wicking-evaporation systems may be used. In some embodiments of the present invention, a wicking-evaporation system comprises an element selected from the group consisting of a natural wick, a plurality of natural wicks, a synthetic wick, a plurality of synthetic wicks, a stick, a plurality of sticks, a reed, a plurality of reeds, a stick, a plurality sticks, a fiber, a plurality of fibers, a mesh, a conductive mesh, a membrane, a porous substrate, a semi-porous substrate, and a combination of any of the preceeding elements.

In some embodiments, the step of dispersing a freshening composition or a component thereof, preferably, a liquid freshening composition or a component thereof into the atmosphere, air, and/or onto a surface, comprises exposing and evaporating the liquid freshening composition or a component thereof into the atmosphere, the air, and/or onto the surface.

In some embodiments, the step of dispersing a freshening composition or a component thereof, preferably, a liquid freshening composition or a component thereof into the atmosphere, air, and/or onto a surface, comprises spraying the liquid freshening composition or a component thereof into the atmosphere, the air, and/or onto the surface.

In some embodiments of a method for delivering a freshening composition or a component thereof, preferably, the scent of a freshening composition or a component thereof, into the atmosphere, air, and/or onto a surface, wherein the freshening composition or a component thereof resides in an air care product or device, such as an air care product, a device or an air freshener device may comprises an evaporative assistance element as described herein. In some embodiments of the present invention, an evaporative assistance element is selected from the group consisting of a heater, a fan, an agitator, and a combination of any of the preceeding evaporative assistance elements.

Delivery of a freshening composition or a component thereof, preferably, the smell or scent of a freshening composition or a component thereof, into the atmosphere, air, or onto a surface, can be noticed by one of ordinary skill in the art and a customer by sniffing.

D. Methods for Modulating the Release of a Freshening Composition

The present invention also provides methods for modulating the release of a freshening composition. It is understood and one of ordinary skill in the art will appreciate that, if not clearly contradicted by the content of this specification, each embodiment of a method for modulating the release of a freshening composition and/or features/elements disclosed as part of that embodiment can be combined with any of the embodiments hereinabove or hereinbelow.

As described in great detail herein, the inventors have found that the release of a freshening composition or a component thereof can be controlled or modulated by employing fragrance release modulators. Employing such fragrance release modulators allows for a customizable control of the release of a freshening composition or a component thereof. When using in combination with a wicking device, it is understood that releasing a freshening composition or a component thereof comprises the step of wicking followed by evaporation of the freshening composition or of a component thereof.

Thus, the present invention provides a method for modulating the release of a freshening composition or a component thereof. Examples E-L provide exemplary guidance for performing such method. While Examples E-L have employed two preferred blends of perfume raw materials and various preferred fragrance release modulators, the inventors have employed the same and other fragrance release modulators with other blends of perfume raw materials and have obtained similar results. As such, the fragrance release modulators described herein, may be used to modulate the release of any freshening composition or a component thereof, comprising any perfume raw material or any blend of perfume raw materials, i.e., regardless of composition of said freshening composition and concentration of each perfume raw material in such freshening composition.

In some embodiments of a method for modulating the release of a freshening composition or a component thereof, the method comprises the step of adding a fragrance release modulator to a perfume raw material.

In some embodiments of a method for modulating the release of a freshening composition or a component thereof, the method comprises the step of adding a fragrance release modulator to a plurality of perfume raw materials.

A fragrance modulator may be added to a perfume raw material or to a plurality of perfume raw materials in various concentrations (see, Examples E-L and as described herein).

In some embodiments of a method for modulating the release of a freshening composition or a component thereof, the method comprises the step of adding a solvent or diluent to a perfume raw material.

In some embodiments of a method for modulating the release of a freshening composition or a component thereof, the method comprises the step of adding a solvent or diluent to a plurality of perfume raw materials.

A solvent or diluent may be added to a perfume raw material or to a plurality of perfume raw materials in various concentrations (see, Examples C-L and as described herein).

Preferred embodiments of this invention are described herein, including the best mode known to the inventors for carrying out the invention. Of course, variations, changes, modifications and substitution of equivalents on those preferred embodiments will become apparent to those of ordinary skill in the art upon reading the foregoing description. The inventors expect skilled artisans to employ such variations, changes, modifications and substitution of equivalents as appropriate, and the inventors intend for the invention to be practiced otherwise than specifically described herein. Those of skill in the art will readily recognize a variety of non-critical parameters that could be changed, altered or modified to yield essentially similar results. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

The referenced patents, patent applications, and scientific literature referred to herein are hereby incorporated by reference in their entirety as if each individual publication, patent or patent application were specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter. Citation of a patent, patent publication, and of any other publication herein shall not be construed in any way as an admission that such patent, patent application and other publication is prior art to an invention claimed herein.

As can be appreciated from the disclosure above, the present invention has a wide variety of applications. The invention is further illustrated by the following examples, which are only illustrative and are not intended to limit the definition and scope of the invention in any way.

III. Examples

The below examples are meant to illustrate specific embodiments of the methods and compositions described herein and should not be construed as limiting the scope of the invention in any way.

Compounds described and used herein can be obtained from various sources, e.g., from Firmenich (Anaheim, Calif., USA), Givaudan (Vernier, Switzerland), IFF (International Flavors & Fragrances; New York, N.Y., USA), Mane, Inc. (Lebanon, Ohio, USA), Berjé, Inc. (Carteret, N.J., USA), Symrise (Elyria, Ohio, USA), Takasago (Crystal Lake, Ill., USA), and Robertet (Piscataway, N.J., USA).

Example A. Preparation of Apple Fragrance, A Blend of Perfume Raw Materials Allyl (3-methylbutoxy) acetate, allyl hexanoate, allyl 3-cyclohexylpropanoate, allyl heptanoate, benzaldehyde, 3-(4-isopropylphenyl)-2-methylpropanal, 2,6-dimethyloct-7-en-2-ol, 1,1-dimethyl-2-phenylethyl acetate, 1,1-dimethyl-2-phenylethyl butyrate, ethyl 2-methylbutanoate, 2-ethyl-3-hydroxy-4H-pyran-4-one, 3-ethoxy-4-hydroxybenzaldehyde, 1,4-dioxacycloheptadecane-5,17-dione, 4-allyl-2-methoxyphenol, ethyl (2-methyl-1,3-dioxolan-2-yl) acetate, methyl (3-oxo-2-pentylcyclopentyl) acetate, hex-2-enal, hexyl acetate, 2-benzylideneoctanal, 4,5,6-trimethylcyclohex-3-ene-1-carbaldehyde, 1-(2,3,8,8-tetramethyl-1,2,3,4,5,6,7,8-octahydronaphthalen-2-yl) ethanone, hex-3-en-1-yl acetate, hex-3-en-1-ol, ethyl 2-methylpentanoate, 5-pentyldihydrofuran-2(3H)-one, 2-phenoxyethyl 2-methylpropanoate, 1-phenylethyl acetate, 2,4-dimethylcyclohex-3-ene-1-carbaldehyde, 5-heptyldihydrofuran-2(3H)-one, and 2-tert-butylcyclohexyl acetate were combined to formulate a blend of perfume raw materials, referred to as Fragrance "Apple" or Apple Fragrance. There is no specific order of addition when combining the individual perfume raw materials to formulate the blend of perfume raw materials.

The freshening composition obtained by the method described in this example is referred to herein, as Fragrance "Apple" or Apple Fragrance. The wt % of each compound in this freshening composition is provided in Table 9:

TABLE 9

Weight percentage of compounds in Fragrance Apple, a blend of perfume raw materials. Weight percentage given for each compound is with reference to the total weight of the blend of perfume raw materials.

| CAS # | IUPAC NOMENCLATURE | WEIGHT PERCENTAGE |
|---|---|---|
| 67634-00-8 | Allyl (3-methylbutoxy) acetate | 2.0 |
| 123-68-2 | Allyl hexanoate | 0.4 |
| 2705-87-5 | Allyl 3-cyclohexylpropanoate | 0.5 |
| 142-19-8 | Allyl heptanoate | 1.0 |
| 100-52-7 | Benzaldehyde | 0.3 |
| 103-95-7 | 3-(4-Isopropylphenyl)-2-methylpropanal | 0.5 |
| 18479-58-8 | 2,6-Dimethyloct-7-en-2-ol | 5.0 |
| 151-05-3 | 1,1-Dimethyl-2-phenylethyl acetate | 1.0 |
| 10094-34-5 | 1,1-Dimethyl-2-phenylethyl butyrate | 5.0 |
| 7452-79-1 | Ethyl 2-methylbutanoate | 0.5 |
| 4940-11-8 | 2-Ethyl-3-hydroxy-4H-pyran-4-one | 0.2 |
| 121-32-4 | 3-Ethoxy-4-hydroxybenzaldehyde | 1.0 |
| 105-95-3 | 1,4-Dioxacycloheptadecane-5,17-dione | 10.0 |
| 97-53-0 | 4-Allyl-2-methoxyphenol | 3.0 |
| 6413-10-1 | Ethyl (2-methyl-1,3-dioxolan-2-yl) acetate | 2.0 |
| 24851-98-7 | Methyl (3-oxo-2-pentylcyclopentyl) acetate | 5.0 |
| 6728-26-3 | Hex-2-enal | 0.1 |
| 142-92-7 | Hexyl acetate | 0.8 |
| 101-86-0 | 2-Benzylideneoctanal | 5.0 |
| 1335-66-6 | 4,5,6-Trimethylcyclohex-3-ene-1-carbaldehyde | 5.0 |
| 54464-57-2 | 1-(2,3,8,8-Tetramethyl-1,2,3,4,5,6,7,8-octahydronaphthalen-2-yl) ethanone | 5.0 |
| 3681-71-8 | Hex-3-en-1-yl acetate | 0.5 |
| 928-96-1 | Hex-3-en-1-ol | 0.7 |
| 39255-32-8 | Ethyl 2-methylpentanoate | 0.5 |
| 104-61-0 | 5-Pentyldihydrofuran-2(3H)-one | 0.7 |
| 103-60-6 | 2-Phenoxyethyl 2-methylpropanoate | 2.0 |
| 93-92-5 | 1-Phenylethyl acetate | 0.3 |
| 68039-49-6 | 2,4-Dimethylcyclohex-3-ene-1-carbaldehyde | 2.0 |
| 104-67-6 | 5-Heptyldihydrofuran-2(3H)-one | 15.0 |
| 88-41-5 | 2-tert-Butylcyclohexyl acetate | 25.0 |
| | TOTAL | 100.00 |

It is understood and one of ordinary skill in the art will appreciate that, if not clearly contradicted by the content of this specification, each embodiment of an Apple Fragrance and/or features/elements disclosed as part of that embodiment can be combined with any of the embodiments hereinabove or hereinbelow. It is further understood and one of ordinary skill in the art will appreciate that, if not clearly contradicted by the content of this specification, each embodiment of a method for preparing an Apple Fragrance and/or features/elements disclosed as part of that embodiment can be combined with any of the embodiments hereinabove or hereinbelow.

Example B. Preparation of Floral Fresh Fragrance, a Blend of Perfume Raw Materials 1-(2,3,8,8-tetramethyl-1,2,3,4,5,6,7,8-octahydronaphthalen-2-yl) ethanone, methyl (3-oxo-2-pentylcyclopentyl) acetate, 2-benzylideneoctanal, 1-cedr-8-en-9-ylethanone, 4-tert-butylcyclohexyl acetate, 1,5-dimethyl-1-vinylhex-4-en-1-yl acetate, 3,7-dimethylocta-1,6-dien-3-ol, 1-(2,6,6-trimethylcyclohex-2-en-1-yl) pent-1-en-3-one, 2-isobutyl-4-methyltetrahydro-2H-pyran-4-ol, 1,4-dioxacycloheptadecane-5,17-dione, 2,6-dimethyloct-7-en-2-ol, 3-(4-isopropylphenyl)-2-methylpropanal, hexyl salicylate, 3-(4-ethylphenyl)-2,2-dimethylpropanal, 3-(2-ethylphenyl)-2,2-dimethylpropanal, 3a,4,5,6,7,7a-hexahydro-1H-4,7-methanoinden-6-yl acetate, Cedarwood oil, Virginian (*Juniperus virginiana* L.), 2-methylundecanal, (2,2-dimethoxyethyl) benzene, undec-10-enal, hex-3-en-1-ol, 3-(1,3-benzodioxol-5-yl)-2-methylpropanal, 1-phenylethyl acetate, 3a,6,6,9a-tetramethyldodecahydronaphtho[2,1-b] furan, allyl (3-methylbutoxy) acetate, and 1-(5,5-dimethylcyclohex-1-en-1-yl) pent-4-en-1-one were combined to formulate a blend of perfume raw materials, referred to as Fragrance "Floral Fresh" or Floral Fresh Fragrance. There is no specific order for combining the individual perfume raw materials to formulate the blend of perfume raw materials.

The freshening composition obtained by the method described in this example is referred to herein, as Floral Fresh Fragrance. The wt % of each compound in this Table 10 at the indicated weight percentage.

TABLE 10

Weight percentage of compounds in Floral Fresh Fragrance, a blend of perfume raw materials. Weight percentage given for each compound is with reference to the total weight of the blend of perfume raw materials.

| CAS # | IUPAC NOMENCLATURE | WEIGHT PERCENTAGE |
|---|---|---|
| 54464-57-2 | 1-(2,3,8,8-Tetramethyl-1,2,3,4,5,6,7,8-octahydronaphthalen-2-yl) ethanone | 14.0 |
| 24851-98-7 | Methyl (3-oxo-2-pentylcyclopentyl) acetate | 12.0 |
| 101-86-0 | 2-Benzylideneoctanal | 11.0 |
| 32388-55-9 | 1-Cedr-8-en-9-ylethanone | 6.0 |
| 32210-23-4 | 4-tert-Butylcyclohexyl acetate | 6.0 |
| 115-95-7 | 1,5-Dimethyl-1-vinylhex-4-en-1-yl acetate | 6.0 |
| 78-70-6 | 3,7-Dimethylocta-1,6-dien-3-ol | 6.0 |
| 1335-46-2 | 1-(2,6,6-Trimethylcyclohex-2-en-1-yl) pent-1-en-3-one | 6.0 |
| 63500-71-0 | 2-Isobutyl-4-methyltetrahydro-2H-pyran-4-ol | 6.0 |
| 105-95-3 | 1,4-Dioxacycloheptadecane-5,17-dione | 6.0 |
| 18479-58-8 | 2,6-Dimethyloct-7-en-2-ol | 6.0 |
| 103-95-7 | 3-(4-Isopropylphenyl)-2-methylpropanal | 2.0 |
| 6259-76-3 | Hexyl salicylate | 2.0 |
| 67634-15-5 | 3-(4-Ethylphenyl)-2,2-dimethylpropanal | 1.40 |
| 67634-14-4 | 3-(2-ethylphenyl)-2,2-dimethylpropanal | 0.6 |
| 5413-60-5 | 3a,4,5,6,7,7a-Hexahydro-1H-4,7-methanoinden-6-yl acetate | 2.0 |
| 8000-27-9 | Cedarwood oil, Virginian (*Juniperus virginiana* L.)* | 2.0 |
| 110-41-8 | 2-Methylundecanal | 1.0 |
| 101-48-4 | (2,2-Dimethoxyethyl) benzene | 0.8 |
| 112-45-8 | Undec-10-enal | 0.6 |
| 928-96-1 | Hex-3-en-1-ol | 0.6 |
| 1205-17-0 | 3-(1,3-Benzodioxol-5-yl)-2-methylpropanal | 0.6 |
| 93-92-5 | 1-Phenylethyl acetate | 0.5 |
| 3738-00-9 | 3a,6,6,9a-Tetramethyldodecahydronaphtho[2,1-b]furan | 0.4 |
| 67634-00-8 | Allyl (3-methylbutoxy) acetate | 0.4 |
| 56973-85-4 | 1-(5,5-Dimethylcyclohex-1-en-1-yl) pent-4-en-1-one | 0.1 |
| | TOTAL | 100.00 |

It is understood and one of ordinary skill in the art will appreciate that, if not clearly contradicted by the content of this specification, each embodiment of a Floral Fresh Fragrance and/or features/elements disclosed as part of that embodiment can be combined with any of the embodiments hereinabove or hereinbelow. It is further understood and one of ordinary skill in the art will appreciate that, if not clearly contradicted by the content of this specification, each embodiment of a method for preparing a Floral Fresh Fragrance and/or features/elements disclosed as part of that embodiment can be combined with any of the embodiments hereinabove or hereinbelow.

Example C. The Influence of Different Solvents on the Release and Evaporation of a Freshening Composition Comprising 50 Wt % Apple Fragrance Various freshening compositions were formulated. Each freshening composition analyzed in this Example consisted of 50 wt % Apple Fragrance (see, Table 9) and 50 wt % solvents. The following solvents were tested: Augeo Clean Multi® (acetone monoglycerol ketal; from Solvay), IPD-AC® (3-methyl-1,3-butanediol-acetate; from Kuraray), STA-SOL® ESS 165 (dimethyl adipate; from ST Laboratories, Inc.), and VOLASIL® DM-2 (dimethicone; from CHEMSIL Silicones, Inc.). Upon adding the freshening composition into a reservoir in an electrical plug-in device having a single wick, release and evaporation of the freshening composition was analyzed. Exemplary results are schematically depicted in FIG. 1.

There is no preferred order of adding the individual ingredient to each other when formulating the liquid freshening composition of the present invention. The liquid freshening composition forms by gentle mixing of the perfume raw materials with the fragrance release modulator (s) and solvent(s) or diluent(s). A clear, temperature stable freshening composition forms. The resulting freshening compositions were tested for temperature stability, which means clarity, no precipitate and no phase separation, at 4° C., at room temperature (RT), at 20° C. to 25° C., and at 40° C. to 42° C. Further, the air freshening compositions were tested for 3 cycles freeze-thaw stability. All experimental data described herein (Examples C-L; FIGS. 1-10) were obtained using the same type of electrical plug-in device comprising: (i) a 25 ml glass reservoir, into which the freshening composition is loaded, (ii) a delivery system, which comprises a 70 mm long and 0.8 mm diameter wick (one end of the wick being in direct contact with the freshening composition, while the other end of the wick is exposed to the external environment), and (iii) an electrical plug-in device, into which the reservoir with the attached wick is fitted It is noted that the use of the electrical plug-in device as described herein, is not limiting. Other devices may be used. In combination with the freshening composition of the present invention. 20 g of freshening composition were used, which contained the indicated wt % for each individual freshening composition (e.g., X wt % of perfume plus Y wt % of FRM and Z wt % of solvent, wherein X+Y+Z=100. The data presented herein consists of daily cumulative percentage released weight-loss, which is calculated as follows: [(initial weight of the entire freshening composition (which consists of the initial weight of the freshening composition+the weight of the reservoir+the weight of the wick+the weight of the electrical plug-in))– (daily weight of the entire freshening composition (which consists of the weight of the freshening composition+the weight of the reservoir+the weight of the wick+the weight of the electrical plug-in))]/initial weight of the air freshening composition.

Figure 2:
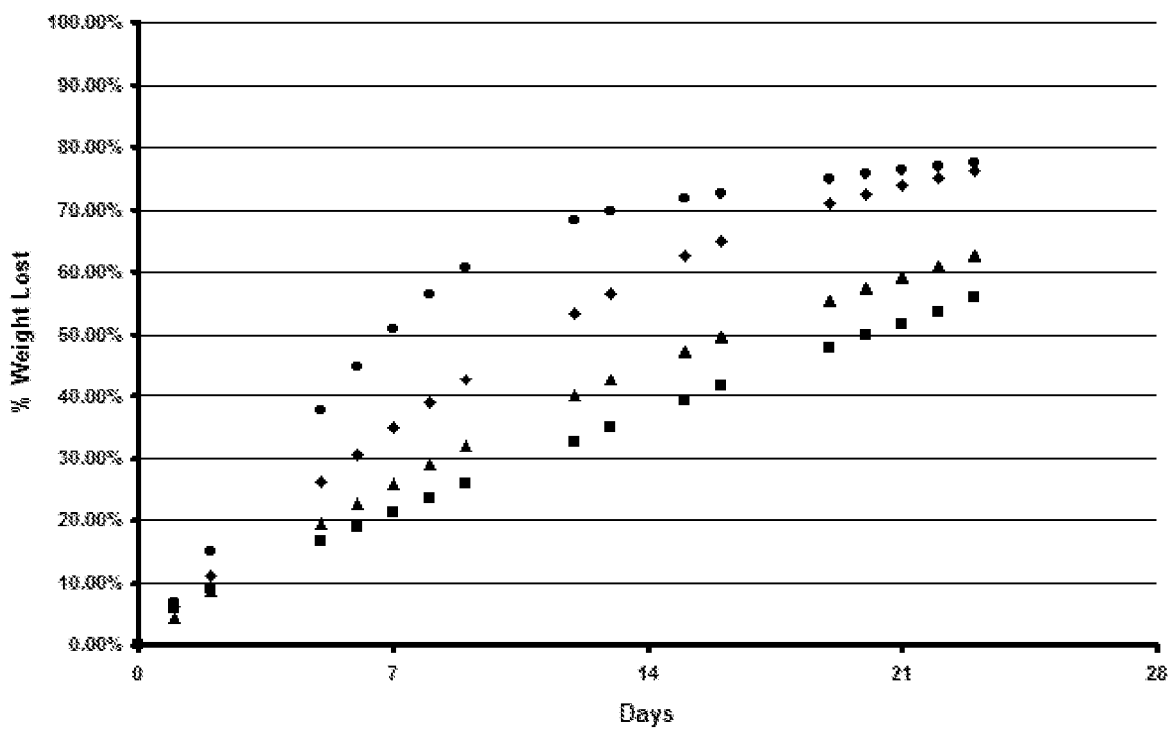
FIG. 2 schematically depicts the influence of different solvents on the release and evaporation of a freshening composition comprising 50 wt % Floral Fresh Fragrance (see, Table 10) and 50 wt % solvents as indicated and measured as % weight lost during the time period indicated. The weight percentage refers to the weight percentage of the entire product formulation, i.e., freshening composition. The following solvents were tested: ●, acetone monoglycerol ketal (Augeo Clean Multi® from Solvay); ♦, 3-methyl-1,3-butanediol-acetate (IPD-AC® from Kuraray); ▲ STA-SOL® ESS 165 (dimethyl adipate (DMA) from ST Laboratories Inc.); ■, silicon solvent (VOLASIL® DM-2 from CHEMSIL Silicones, Inc.). Details are described in Example D.

Example D. The Influence of Different Solvents on the Release and Evaporation of a Freshening Composition Comprising 50 Wt % Floral Fresh Fragrance Various freshening compositions were formulated. Each freshening composition analyzed in this Example consisted of 50 wt % Floral Fresh Fragrance (see, Table 10) and 50 wt % solvents. The following solvents were tested: Augeo Clean Multi® (acetone monoglycerol ketal; from Solvay), IPD-AC® (3-methyl-1,3-butanediol-acetate; from Kuraray), STA-SOL® ESS 165 (dimethyl adipate; from ST Laboratories, Inc.), and VOLASIL® DM-2 (dimethicone; from CHEMSIL Silicones, Inc.). Release and evaporation of the freshening composition was tested as described in Example C. Exemplary results are schematically depicted in FIG. 2.

Example E. The Influence of Different Fragrance Release Modulators (FRMs) on the Release and Evaporation of a Freshening Composition Comprising 50 Wt % Apple Fragrance and 42.5 Wt % of Solvent Augeo Clean Multi®

Figure 3:
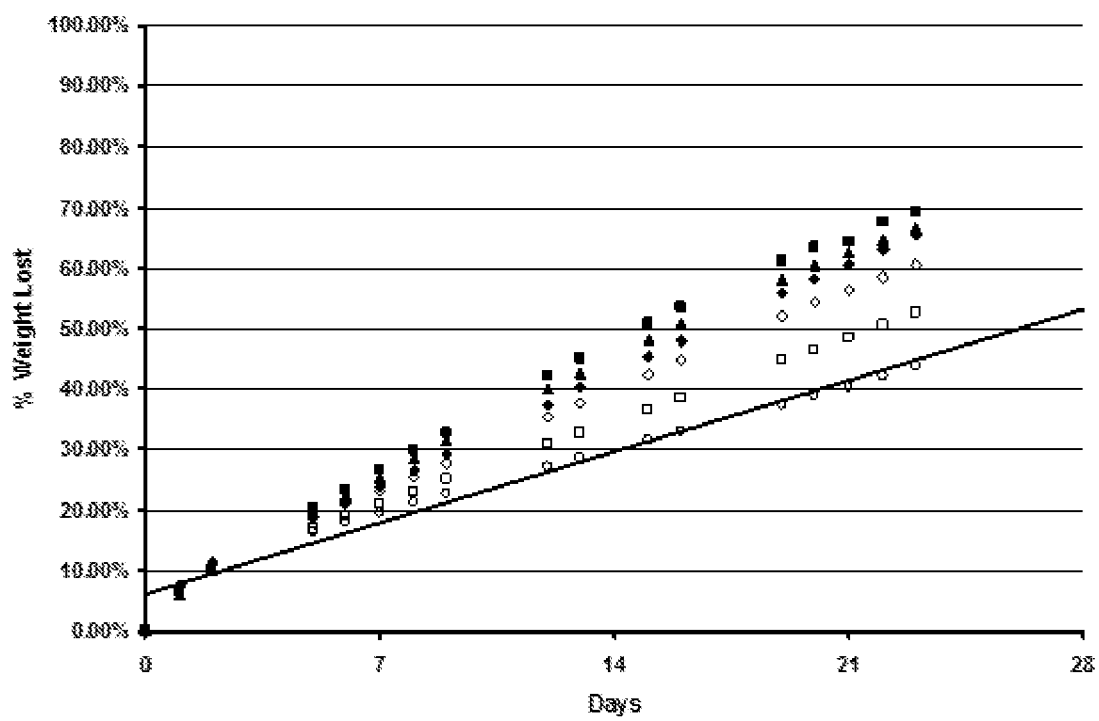
FIG. 3 schematically depicts the influence of different fragrance release modulators (FRM) on the release and evaporation of a freshening composition comprising 50 wt % of an Apple Fragrance (see, Table 9), 42.5 wt % of solvent Augeo Clean Multi® and 7.5 wt % of the indicated FRM and measured as % weight lost during the time period indicated. The weight percentage refers to the weight percentage of the entire product formulation, i.e., freshening composition. The following combinations of Apple Fragrance/Augeo Clean Multi® and FRMs were tested: ○, 50 wt % Apple Fragrance/50 wt % Augeo Clean Multi®; ♦, 50 wt % Apple Fragrance/42.5 wt % Augeo Clean Multi®/7.5 wt % EtOH; ■, 50 wt % Apple Fragrance/42.5 wt % Augeo Clean Multi®/7.5 wt % TEC (TEC, triethyl citrate); 0, 50 wt % Apple Fragrance/42.5 wt % Augeo Clean Multi®/7.5 wt % MMB (MMB, 3-methyl 3-methoxyl butanol); ▲ 50 wt % Apple 42.5 wt % Augeo Clean Multi®/7.5 wt % BB (BB, benzyl benzoate); Q, 50 wt % Apple Fragrance/42.5 wt % Augeo Clean Multi®/7.5 wt % DPG (DPG, dipropylene glycol). Details are described in Example E.

Various freshening compositions were formulated. Each freshening composition analyzed in this Example consisted of 50 wt % Apple Fragrance (see, Table 9) 42.5 wt % solvent Augeo Clean Multi® (acetone monoglycerol ketal) and 7.5 wt % of the following Fragrance Release Modulators (FRMs): EtOH (ethanol), TEC (triethyl citrate), MMB (3-methyl 3-methoxyl butanol), BB (benzyl benzoate), and DPG (dipropylene glycol). Release and evaporation of the freshening composition was tested as described in Example C. Exemplary results are schematically depicted in FIG. 3.

Example F. The Influence of Different Fragrance Release Modulators (FRMs) on the Release and Evaporation of a Freshening Composition Comprising 50 Wt % Floral Fresh Fragrance and 42.5 Wt % of Solvent IPD-AC®

Figure 4:
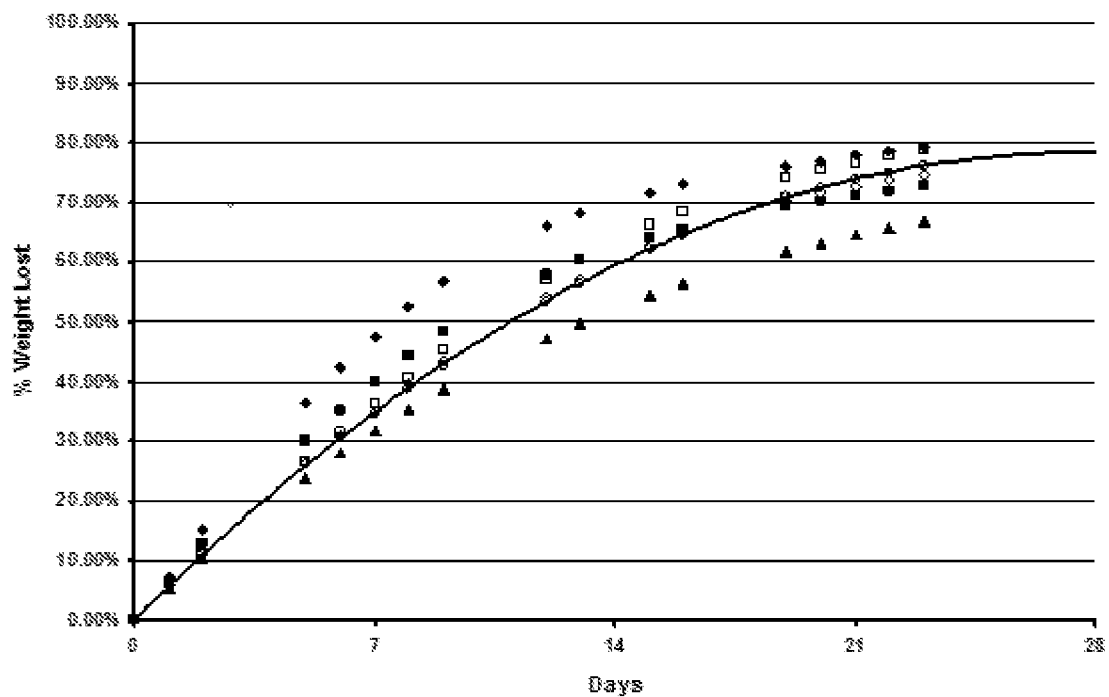
FIG. 4 schematically depicts the influence of different fragrance release modulators (FRM) on the release of a freshening composition comprising 50 wt % of a Floral Fresh Fragrance (see, Table 10), 42.5 wt % of solvent IPD-AC® and 7.5 wt % of the indicated FRM and measured as % weight lost during the time period indicated. The weight percentage refers to the weight percentage of the entire product formulation, i.e., freshening composition. The following combinations of Floral Fresh Fragrance/IPD-AC® and FRMs were tested: ○, 50 wt % Floral Fresh Fragrance/50 wt % IPD-AC®; ♦, 50 wt % Floral Fresh Fragrance/42.5 wt % IPD-AC®/7.5 wt % EtOH; ■, 50 wt % Floral Fresh Fragrance/42.5 wt % IPD-AC®/7.5 wt % TEC (TEC, triethyl citrate); ◇, 50 wt % Floral Fresh Fragrance/42.5 wt % IPD-AC®/7.5 wt % MMB (MMB, 3-methyl 3-methoxyl butanol); ▲ 50 wt % Floral Fresh Fragrance/42.5 wt % IPD-AC®/7.5 wt % BB (BB, benzyl benzoate); □, 50 wt % Floral Fresh Fragrance/42.5 wt % IPD-AC®/7.5 wt % DPG (DPG, dipropylene glycol). Details are described in Example F.

Various freshening compositions were formulated. Each freshening composition analyzed in this Example consisted of 50 wt % Floral Fresh Fragrance (see, Table 10) 42.5 wt % solvent IPD-AC® (3-methyl-1,3-butanediol-acetate) and 7.5 wt % of the following fragrance release modulators (FRMs): EtOH (ethanol), TEC (triethyl citrate), MMB (3-methyl 3-methoxyl butanol), BB (benzyl benzoate), and DPG (dipropylene glycol). Release and evaporation of the freshening composition was tested as described in Example C. Exemplary results are schematically depicted in FIG. 4.

Example G. The Influence of Fragrance Release Modulator Benzyl Benzoate on the Release and Evaporation of a Freshening Composition Comprising 50 Wt % Apple Fragrance and Solvent Augeo Clean Multi®

Figure 5:
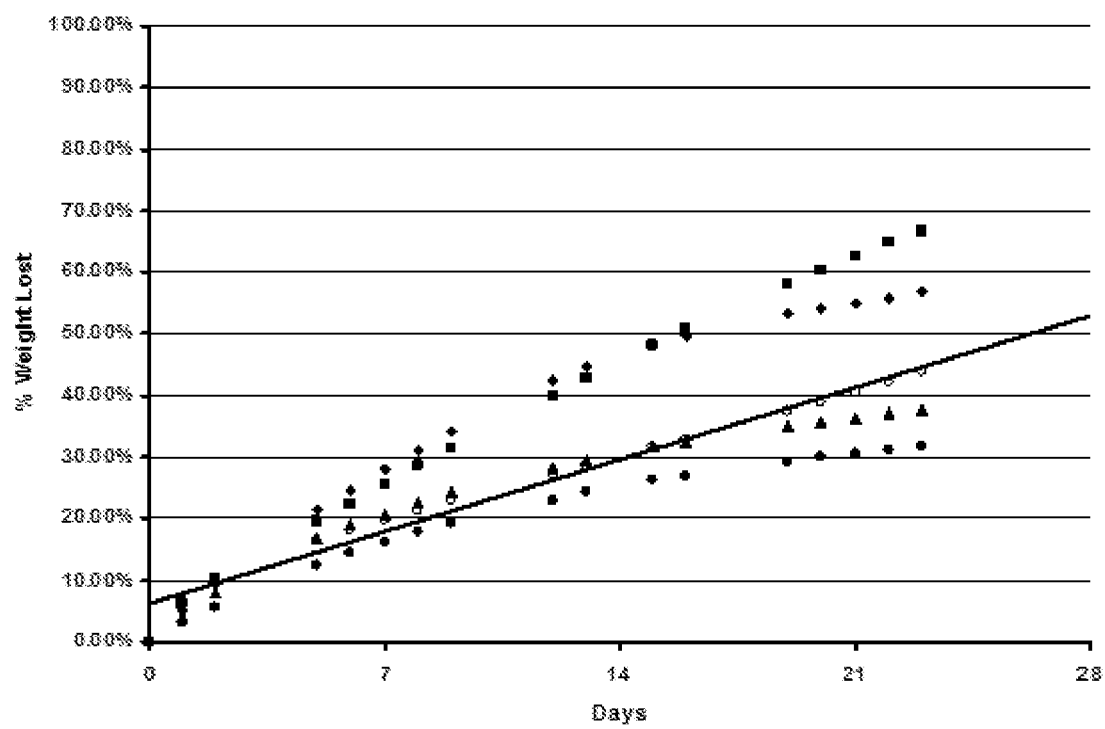
FIG. 5 schematically depicts the influence of various amounts of fragrance release modulator BB (benzyl benzoate) on the release and evaporation of a freshening composition comprising 50 wt % Apple Fragrance (see, Table 9) and various amounts of solvent Augeo Clean Multi® measured as % weight lost during the time period indicated. The weight percentage refers to the weight percentage of the entire product formulation, i.e., freshening composition. The release and evaporation of the following freshening compositions were tested: ○, 50 wt % Apple Fragrance/50 wt % Augeo Clean Multi®; ■, 50 wt % Apple Fragrance/42.5 wt % Augeo Clean Multi®/7.5 wt % BB; ♦, 50 wt % Apple Fragrance/25 wt % Augeo Clean Multi®/25 wt % BB; ▲, 50 wt % Apple Fragrance/7.5 wt % Augeo Clean Multi®/42.5 wt % BB; ●, 50 wt % Apple Fragrance/50 wt % BB. Abbreviations and names are as described for FIGS. 1-4. Details are described in Example G.

Various freshening compositions were formulated. Each freshening composition analyzed in this Example consisted of 50 wt % Apple Fragrance (see, Table 9), various wt % solvent Augeo Clean Multi® and various wt % of fragrance release modulator BB (benzyl benzoate). The following freshening compositions were formulated and tested: 50 wt % Apple Fragrance/50 wt % Augeo Clean Multi®; 50 wt % Apple Fragrance/42.5 wt % Augeo Clean Multi®/7.5 wt % BB; 50 wt % Apple Fragrance/25 wt % Augeo Clean Multi®/25 wt % BB; 50 wt % Apple Fragrance/7.5 wt % Augeo Clean Multi®/42.5 wt % BB; and 50 wt % Apple Fragrance/50 wt % BB. Release and evaporation of the freshening compositions was tested as described in Example C. Exemplary results are schematically depicted in FIG. 5.

Example H. The Influence of Fragrance Release Modulator Benzyl Benzoate on the Release and Evaporation of a Freshening Composition Comprising 50 Wt % Floral Fresh Fragrance and IPD-AC®

Figure 6:
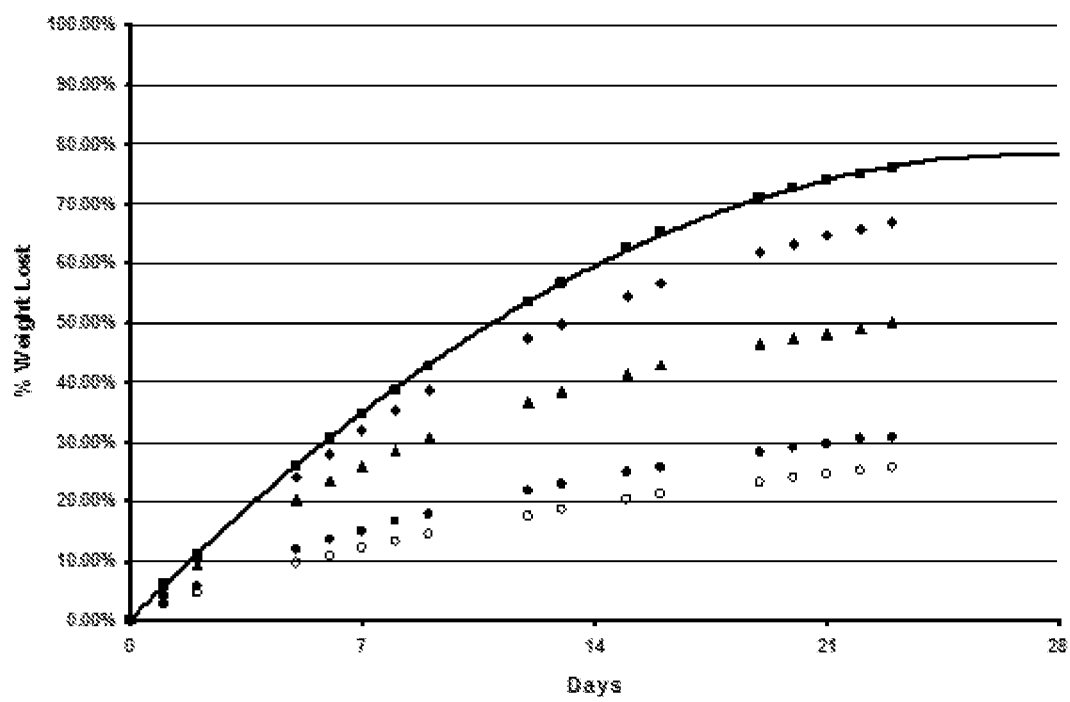
FIG. 6 schematically depicts the influence of fragrance release modulator BB (benzyl benzoate) on the release of a freshening composition comprising 50 wt % Floral Fresh Fragrance (see, Table 10) and various amounts of solvent IPD-AC® and measured as % weight lost during the time period indicated. The weight percentage refers to the weight percentage of the entire product formulation, i.e., freshening composition. The release and evaporation of the following freshening compositions were tested: ♦, 50 wt % Floral Fresh Fragrance/42.5 wt % IPD-AC®/7.5 wt % BB; ▲, 50 wt % Floral Fresh Fragrance/25 wt % IPD-AC®/25 wt % BB; ●, 50 wt % Floral Fresh Fragrance/7.5 wt % IPD-AC®/42.5 wt % BB; ■, 50 wt % Floral Fresh Fragrance/50 wt % IPD-AC®; ○, 50 wt % Floral Fresh Fragrance/50 wt % BB. Abbreviations and names are as described for FIGS. 1-5. Details are described in Example H.

Various freshening compositions were formulated. Each freshening composition analyzed in this Example consisted of 50 wt % Floral Fresh Fragrance (see, Table 10), various wt % solvent IPD-AC® and various wt % of fragrance release modulator BB (benzyl benzoate). The following freshening compositions were formulated and tested: 50 wt % Floral Fresh Fragrance/50 wt % IPD-AC®; 50 wt % Floral Fresh Fragrance/42.5 wt % IPD-AC®/7.5 wt % BB; 50 wt % Floral Fresh Fragrance/25 wt % IPD-AC®/25 wt % BB; 50 wt % Floral Fresh Fragrance/7.5 wt % IPD-AC®/42.5 wt % BB; and 50 wt % Floral Fresh Fragrance/50 wt % BB. Release and evaporation of the freshening compositions was tested as described in Example C. Exemplary results are schematically depicted in FIG. 6.

Example I. The Influence of Various Solvents on the Release and Evaporation of a Freshening Composition Comprising Either 50 Wt % Apple Fragrance or 50 Wt % Floral Fresh Fragrance Various freshening compositions were formulated. Each freshening composition analyzed in this Example consisted of either 50 wt % Apple Fragrance (see, Table 9) or 50 wt % Floral Fresh Fragrance (see, Table 10) and 50 wt % of a solvent as indicated. The following freshening compositions were formulated and tested: 50 wt % Apple Fragrance/50 wt % Augeo Clean Multi®; 50 wt % Apple Fragrance/50 wt % DMA; 50 wt % Apple Fragrance/50 wt % VOLASIL® DM-2; 50 wt % Apple Fragrance/50 wt % IPD-AC®; 50 wt % Floral Fresh Fragrance/50 wt % Augeo Clean Multi®; 50 wt % Floral Fresh Fragrance/50 wt % DMA; 50 wt % Floral Fresh Fragrance/50 wt % VOLASIL DM-2; and 50 wt % Floral Fresh Fragrance/50 wt % IPD-AC®. Release and evaporation of the freshening compositions was tested as described in Example C. Exemplary results are schematically depicted in FIG. 7.

Figure 7:
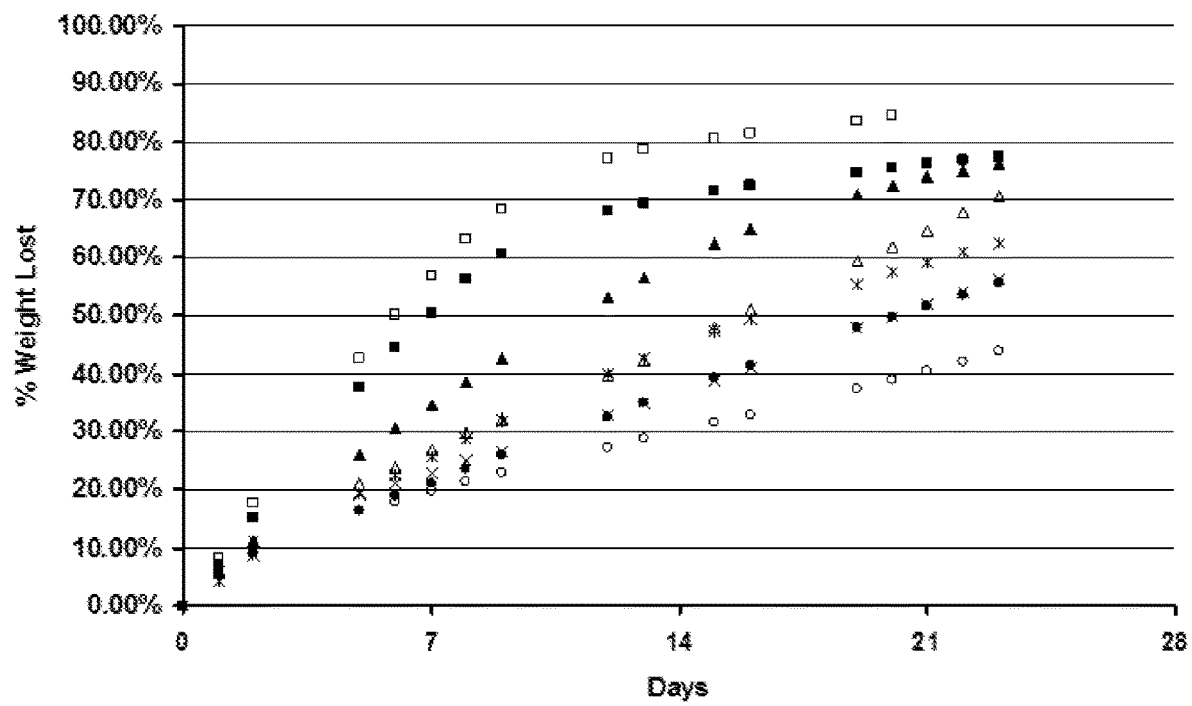
FIG. 7 schematically depicts the influence of different solvents on the release and evaporation of a freshening composition either comprising 50 wt % Apple Fragrance or 50 wt % Floral Fresh Fragrance (see, Tables 9 and 10) and 50 wt % solvents as indicated and measured as % weight lost during the time period indicated. The weight percentage refers to the weight percentage of the entire product formulation, i.e., freshening composition. The release and evaporation of the following freshening compositions were tested: ○, 50 wt % Apple Fragrance/50 wt % Augeo Clean Multi®; ●, 50 wt % Floral Fresh Fragrance/50 wt % Augeo Clean Multi®; x, 50 wt % Apple Fragrance/50 wt % DMA (dimethyl adipate); Ж, 50 wt % Floral Fresh Fragrance/50 wt % DMA; Δ, 50 wt % Apple Fragrance/50 wt % IPD-AC®; ▲, 50 wt % Floral Fresh Fragrance/50 wt % IPD-AC®; □, 50 wt % Apple Fragrance/50 wt % VOLASIL® DM-2; ■, 50 wt % Floral Fresh Fragrance/50 wt % VOLASIL® DM-2. Abbreviations are as in FIGS. 1-6. Details are described in Example I.

The result shown in FIG. 7 is somewhat similar to the results shown in FIGS. 1 and 2, respectively, however, emphasizes a different aspect. FIG. 7 schematically depicts the difference in release performance of the same product compositions (i.e., either Apple Fragrance or Floral Fresh Fragrance) due to the different type of solvent used. As can be seen in FIG. 7, air freshener products, regardless of the fragrance used, based on the VOLASIL® DM-2 solvent are the fastest ones to release the freshening composition, while the Augeo Clean Multi® are the slowest ones to release the freshening compositions.

Figure 8:
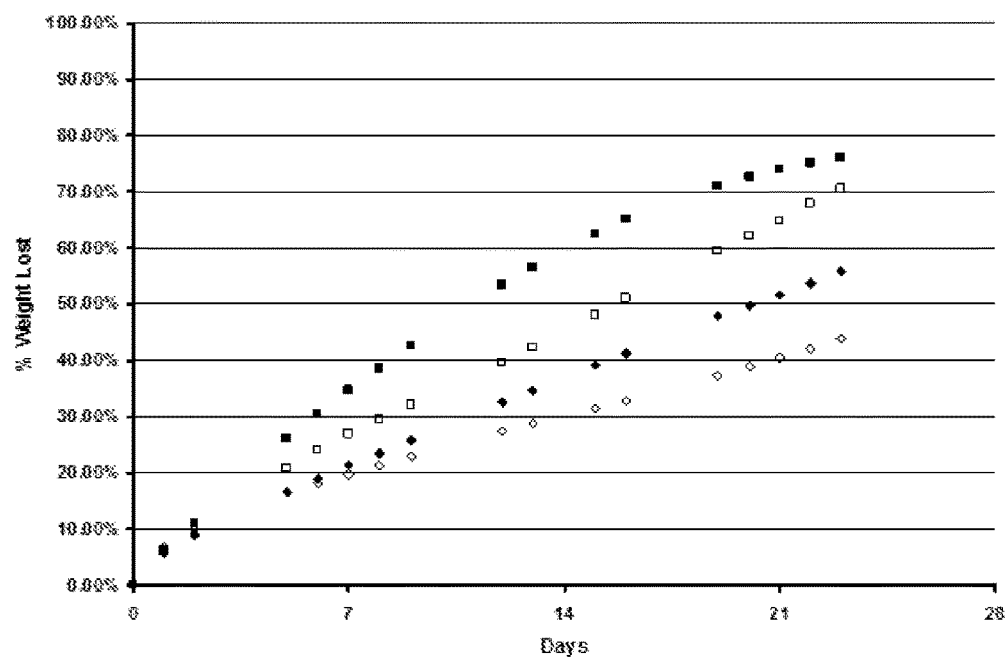
FIG. 8 schematically depicts the influence of different solvents on the release and evaporation of a freshening composition either comprising 50 wt % Apple Fragrance or 50 wt % Floral Fresh Fragrance (see, Tables 9 and 10) and measured as % weight lost during the time period indicated. The weight percentage refers to the weight percentage of the entire product formulation, i.e., freshening composition. Release and evaporation of the following freshening compositions were tested: ◇, 50 wt % Apple Fragrance/50 wt % Augeo Clean Multi®; ♦, 50 wt % Floral Fresh Fragrance/50 wt % Augeo Clean Multi®; □, 50 wt % Apple Fragrance/50 wt % IPD-AC®; ■, 50 wt % Floral Fresh Fragrance/50 wt % IPD-AC®. Abbreviations are as in FIGS. 1-7. Details are described in Example J.

Example J. The Influence of Solvents Augeo Clean Multi® and IPD-AC® on the Release and Evaporation of a Freshening Composition Comprising Either 50% Apple Fragrance or 50% Floral Fresh Fragrance Various freshening compositions were formulated. Each freshening composition analyzed in this Example consisted of either 50 wt % Apple Fragrance (see, Table 9) or 50 wt % Floral Fresh Fragrance (see, Table 10) and 50 wt % of a solvent as indicated. The following freshening compositions were formulated and tested: 50 wt % Apple Fragrance/50 wt % Augeo Clean Multi®; 50 wt % Apple Fragrance/50 wt % IPD-AC®; 50 wt % Floral Fresh Fragrance/50 wt % Augeo Clean Multi®; and 50 wt % Floral Fresh Fragrance/50 wt % IPD-AC® Release and evaporation of the freshening compositions was tested as described in Example C. Exemplary results are schematically depicted in FIG. 8.

Example K. The Influence of Different Fragrance Release Modulators (FRMs) on the Release and Evaporation of a Freshening Composition Comprising 50 Wt % Floral Fresh Fragrance and Solvent IPD-AC®

Figure 9:
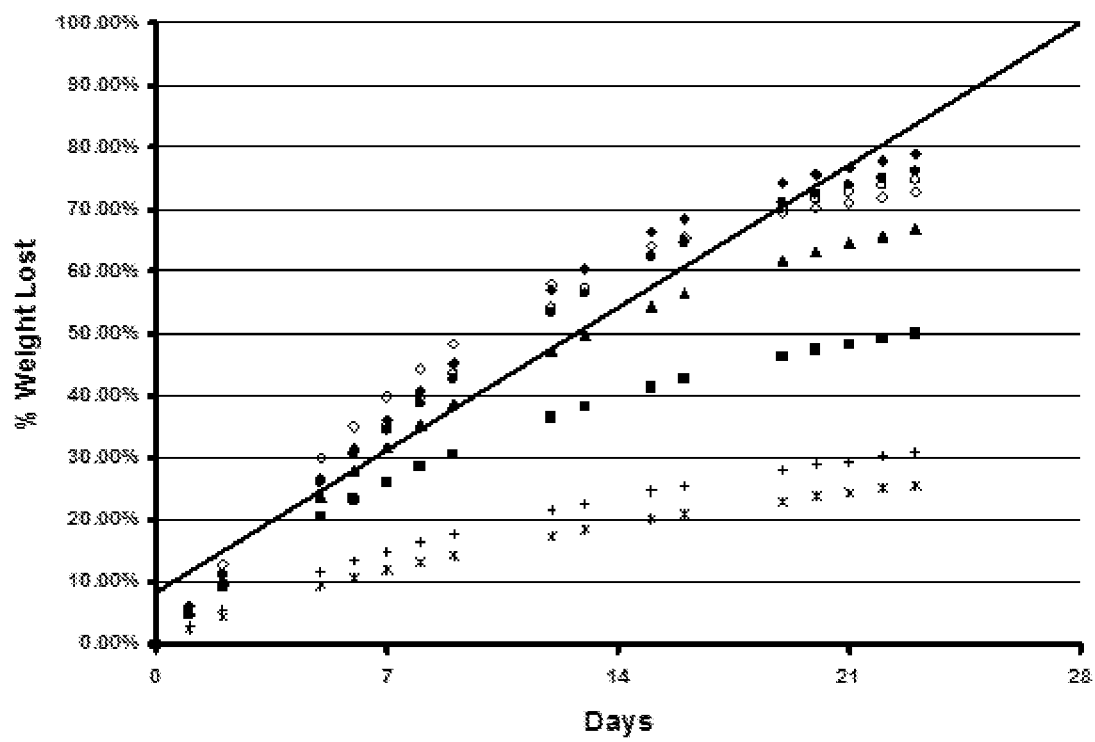
FIG. 9 schematically depicts the influence of different fragrance release modulators (FRM) on the release and evaporation of a freshening composition comprising Floral Fresh Fragrance and as measured as % weight lost during the time period indicated. The weight percentage refers to the weight percentage of the entire product formulation, i.e., freshening composition. The release and evaporation of the following freshening compositions were tested: ○, 50 wt % Floral Fresh Fragrance/42.5 wt % IPD-AC®/7.5 wt % MMB (IPD-AC®, 3-methyl-1,3-butanediol-acetate; MMB, 3-methyl 3-methoxyl butanol); ▲ 50 wt % Floral Fresh Fragrance/42.5 wt % IPD-AC®/7.5 wt % BB (BB, benzyl benzoate); ◇, 50 wt % Floral Fresh Fragrance/42.5 wt % IPD-AC®/7.5 wt % TEC (TEC, triethyl citrate); ♦, 50% Floral Fresh Fragrance/42.5 wt % IPD-AC®/7.5 wt % DPG (DPG, dipropylene glycol); ■, 50% Floral Fresh Fragrance/25 wt % IPD-AC®/25 wt % BB; +, 50 wt % Floral Fresh Fragrance/7.5 wt % IPD-AC®/42.5 wt % BB; ●, 50 wt % Floral Fresh Fragrance/50 wt % IPD-AC®; Ж, 50 wt % Floral Fresh Fragrance/50 wt % BB. Abbreviations and names are as described for FIGS. 1-8. Details are described in Example K.

Various freshening compositions were formulated. Each freshening composition analyzed in this Example consisted of 50 wt % Floral Fresh Fragrance (see, Table 10), various wt % of solvent IPD-AC® and various wt % of a fragrance release modulator as indicated. The following freshening compositions were formulated and tested: 50 wt % Floral Fresh Fragrance/42.5 wt % IPD-AC®/7.5 wt % MMB; 50 wt % Floral Fresh Fragrance/42.5 wt % IPD-AC®/7.5 wt % BB; 50 wt % Floral Fresh Fragrance/42.5 wt % IPD-AC®/7.5 wt % TEC; 50 wt % Floral Fresh Fragrance/42.5 wt % IPD-AC®/7.5 wt % DPG; 50 wt % Floral Fresh Fragrance/25 wt % IPD-AC®/25 wt % BB; 50 wt % Floral Fresh Fragrance/7.5 wt % IPD-AC®/42.5 wt % BB; 50% Floral Fresh Fragrance/50 wt % IPD-AC®; 50% Floral Fresh Fragrance/50 wt % BB. Release and evaporation of the freshening compositions was tested as described in Example C. Exemplary results are schematically depicted in FIG. 9.

Figure 10:
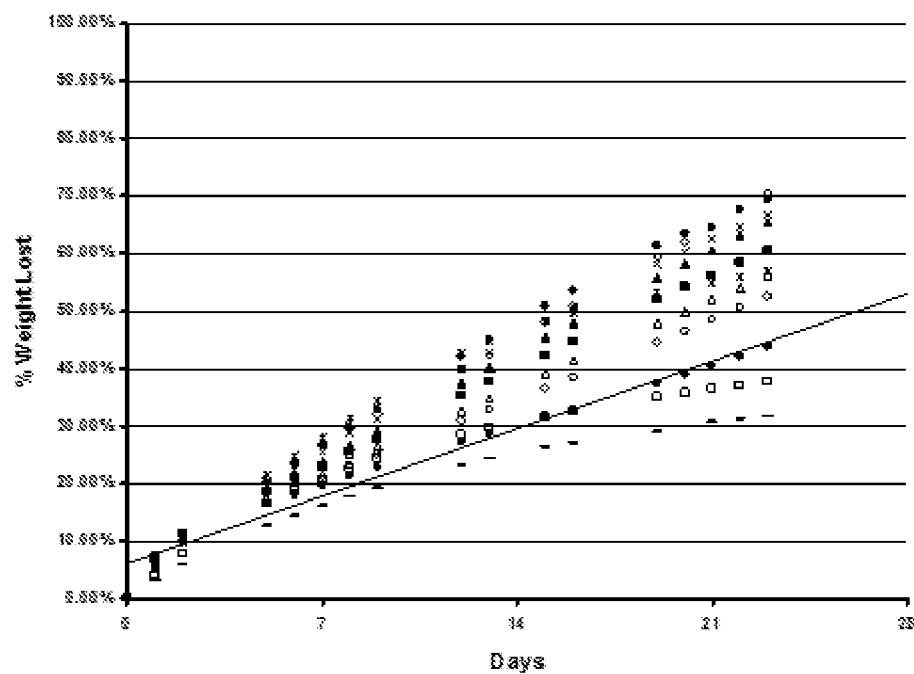
FIG. 10 schematically depicts the influence of different fragrance release modulators (FRM) on the release and evaporation of a freshening composition comprising 50% wt % Apple Fragrance and as measured as % weight lost during the time period indicated. The weight percentage refers to the weight percentage of the entire product formulation, i.e., freshening composition. The release and evaporation of the following fragrance compositions were tested: 0, 50 wt % Apple Fragrance/50 wt % IPD-AC®; Δ, 50 wt % Apple Fragrance/50 wt % STA-SOL® ESS 165; ■, 50 wt % Apple Fragrance/42.5 wt % Augeo Clean Multi®/7.5 wt % MMB; ▲, 50 wt % Apple Fragrance/42.5 wt % Augeo Clean Multi®/7.5 wt % EtOH (EtOH, ethanol); x, 50 wt % Apple Fragrance/42.5 wt % Augeo Clean Multi®/7.5 wt % BB; ●, 50 wt % Apple Fragrance/42.5 wt % Augeo Clean Multi®/7.5 wt % TEC; ○, 50 wt % Apple Fragrance/42.5 wt % Augeo Clean Multi®/7.5 wt % DPG; Ж, 50 wt % Apple Fragrance/25 wt % Augeo Clean Multi®/25 wt % BB; □, 50 wt % Apple Fragrance/7.5 wt % Augeo Clean Multi®/42.5 wt % BB; -, 50 wt % Apple Fragrance/50 wt % BB. Abbreviations and names are as described for FIGS. 1-9. Details are described in Example L.

Example L. The Influence of Different Fragrance Release Modulators (FRMs) on the Release and Evaporation of a Freshening Composition Comprising 50 Wt % Apple Fragrance and Various Solvents Various freshening compositions were formulated. Each freshening composition analyzed in this Example consisted of 50 wt % Apple Fragrance (see, Table 9), various wt % of solvent Augeo Clean Multi® and various wt % of a fragrance release modulator as indicated. The following freshening compositions were formulated and tested: 50 wt % Apple Fragrance/50 wt % IPD-AC®; 50 wt % Apple Fragrance/50 wt % STA-SOL® ESS 165; 50 wt % Apple Fragrance/42.5 wt % Augeo Clean Multi®/7.5 wt % MMB; 50 wt % Apple Fragrance/42.5 wt % Augeo Clean Multi®/7.5 wt % EtOH; 50 wt % Apple Fragrance/42.5 wt % Augeo Clean Multi®/7.5 wt % BB; 50 wt % Apple Fragrance/42.5 wt % Augeo Clean Multi®/7.5 wt % TEC; 50 wt % Apple Fragrance/42.5 wt % Augeo Clean Multi®/7.5 wt % DPG; 50 wt % Apple Fragrance/25 wt % Augeo Clean Multi®/25 wt % BB; 50 wt % Apple Fragrance/7.5 wt % Augeo Clean Multi®/42.5 wt % BB; 50 wt % Apple Fragrance/50 wt % BB. Release and evaporation of the freshening compositions was tested as described in Example C. Exemplary results are schematically depicted in FIG. 10.

What is claimed is:

1. A freshening composition comprising:
   (i) from about 0.1 wt % to about 95 wt % perfume raw material, the perfume raw material comprising one or more ingredients selected from the group consisting of an ester, an alcohol, an aldehyde, a ketone, an acetal, a phenol, an ether, a lactone, a furan, a hydrocarbon, an acid, a natural origin fragrance compound, a synthetic origin fragrance compound, a stereoisomer of any preceding perfume raw material, and a mixture of any of the preceding perfume raw materials;
   (ii) from about 1.0 wt % to about 95 wt % of a solvent; and
   (iii) from about 2 wt % to about 90 wt % fragrance release modulator having two or more characteristics selected from the group consisting of:
      (a) a flash point higher than about 100°F,
      (b) a surface tension of less than about 60 mN/m,
      (c) a dynamic viscosity from about 0.5 cp to about 100 cp, and
      (d) a density from about 600 g/l to about 1,300 g/l;
   wherein the fragrance release modulator is selected from the group consisting of an alkyl-ether, an aryl-ether, an alkyl-glycol, an aryl-glycol, an alkyl-carbonate, an aryl-carbonate, an alkyldiol, an alkyl-adipate, an aryl-adipate, an alkyl-benzoate, an aryl-benzoate, an aryl-citrate, an alkyl-laurate, an aryl-laurate, an alkyl-palmitate, an aryl-palmitate, an alkyl-stearate, an aryl-stearate, an aryl-myristate, an alkyl-succinate, an aryl-succinate, an alkyl-glutarate, an aryl-glutarate, a silicon solvent, a stereoisomer of any preceding fragrance release modulator, and a mixture of any of the preceding fragrance release modulators;
   wherein the fragrance release modulator is not dipropylene glycol, not dimethyl ether, and not dimethyl adipate;
   wherein the freshening composition comprises the fragrance release modulator in an amount sufficient to control release of the freshening composition or of a component thereof when the freshening composition resides within an air freshener device;
   wherein the solvent does not comprise dimethyl adipate;
   wherein the perfume raw material, the solvent and the fragrance release modulator are different ingredients;
   wherein the freshening composition does not comprise water; and
   wherein the freshening composition is adapted to have three or more of a characteristic selected from the group consisting of:
      (a) a flash point higher than about 100°F,
      (b) a surface tension from about 10 mN/m to about 40 mN/m,
      (c) a dynamic viscosity from about 1 cp to about 30 cp, and
      (d) a density from about 650 g/l to about 1,300 g/l.

2. The freshening composition of claim 1, wherein the perfume raw material comprises a plurality of perfume raw materials.

3. The freshening composition according to claim 2, wherein the plurality of perfume raw materials comprises one or more compounds selected from the group consisting of allyl (3-methylbutoxy) acetate, allyl hexanoate, allyl 3-cyclohexylpropanoate, allyl heptanoate, benzaldehyde, 3-(4-isopropylphenyl)-2-methylpropanal, 2,6-dimethyloct-7-en-2-ol, 1,1-dimethyl-2-phenylethyl acetate, 1,1-dimethyl-2-phenylethyl butyrate, ethyl 2-methylbutanoate, 2-ethyl-3-hydroxy-4H-pyran-4-one, 3-ethoxy-4-hydroxybenzaldehyde, 1,4-dioxacycloheptadecane-5,17-dione, 4-allyl-2-methoxyphenol, ethyl (2-methyl-1,3-dioxolan-2-yl) acetate, methyl (3-oxo-2-pentylcyclopentyl) acetate, hex-2-enal, hexyl acetate, 2-benzylideneoctanal, 4,5,6-trimethylcyclohex-3-ene-1-carbaldehyde, 1-(2,3,8,8-tetramethyl-1,2,3,4,5,6,7,8-octahydronaphthalen-2-yl) ethanone, hex-3-en-1-yl acetate, hex-3-en-1-ol, ethyl 2-methylpentanoate, 5-pentyldihydrofuran-2(3H)-one, 2-phenoxyethyl 2-methylpropanoate, 1-phenylethyl acetate, 2,4-dimethylcyclohex-3-ene-1-carbaldehyde, 5-heptyldihydrofuran-2(3H)-one, and 2-tert-butylcyclohexyl acetate.

4. The freshening composition according to claim 2, wherein the plurality of perfume raw materials comprises one or more compounds selected from the group consisting of 1-(2,3,8,8-tetramethyl-1,2,3,4,5,6,7,8-octahydronaphthalen-2-yl) ethanone, methyl (3-oxo-2-pentylcyclopentyl)

acetate, 2-benzylideneoctanal, 1-cedr-8-en-9-ylethanone, 4-tert-butylcyclohexyl acetate, 1,5-dimethyl-1-vinylhex-4-en-1-yl acetate, 3,7-dimethylocta-1,6-dien-3-ol, 1-(2,6,6-trimethylcyclohex-2-en-1-yl) pent-1-en-3-one, 2-isobutyl-4-methyltetrahydro-2H-pyran-4-ol, 1,4-dioxacycloheptadecane-5,17-dione, 2,6-dimethyloct-7-en-2-ol, 3-(4-isopropylphenyl)-2-methylpropanal, hexyl salicylate, 3-(4-ethylphenyl)-2,2-dimethylpropanal, 3-(2-ethylphenyl)-2,2-dimethylpropanal, 3a,4,5,6,7,7a-hexahydro-1H-4,7-methanoinden-6-yl acetate, cedarwood oil, 2-methylundecanal, (2,2-dimethoxyethyl) benzene, undec-10-enal, hex-3-en-1-ol, 3-(1,3-benzodioxol-5-yl)-2-methylpropanal, 1-phenylethyl acetate, 3a,6,6,9a-tetramethyldodecahydronaphtho[2,1-b] furan, allyl (3-methylbutoxy) acetate, and 1-(5,5-dimethylcyclohex-1-en-1-yl) pent-4-en-1-one.

5. The freshening composition according to claim 1, wherein the solvent is selected from the group consisting of an alkyladipate, an aryladipate, an alkyl-glycerol, an aryl-glycerol, an alkyldiol, an aryldiol, an isoparaffine, a silicon, and a mixture of any of the preceding solvents.

6. The freshening composition according to claim 1, wherein the solvent is selected from the group consisting of 2,2-dimethyl-1,3-dioxolane-4-methanol, 3-methyl-1,3-butanediol-1-acetate, dimethicone, disiloxane, trisiloxane, a $C_{15-19}$alkane, a $C_{13-19}$isoparaffine, a cyclosiloxane, an alkyl-cyclosiloxane, an aryl-cyclosiloxane, and a combination of any of the preceding solvents.

7. The freshening composition according to claim 1, wherein the fragrance release modulator is selected from the group consisting of propylene glycol, hexyleneglycol, glycerol, benzyl benzoate, dioctyl adipate, propylene carbonate, dimethyl carbonate, isoamyl laurate, methyl palmitate, methyl stearate, dimethyl succinate, dimethyl glutarate, and a mixture of any of the preceding fragrance release modulators.

8. The freshening composition according to claim 1, further comprising less than 50 wt % of an ingredient having a functional activity and wherein the ingredient having the functional activity is selected from the group consisting of an ingredient having malodor counteracting activity, an ingredient having antimicrobial activity, an insect repellant, a preservative, an antioxidant, a humectant, a UV-blocking agent, a pigment, a dye, a surfactant, an emulsifier, a solubilizer, a polymer, and a buffer.

9. The freshening composition according to claim 8, wherein the ingredient having malodor counteracting activity is cyclodextrin.

10. The freshening composition according to claim 8, wherein the ingredient having antimicrobial activity is selected from the group consisting of a paraben, benzyl alcohol, phenol, cresol, cetrimide, thiomersal, hexylene glycol, 1,2 hexanediol, and phenoxy ethanol.

11. The freshening composition according to claim 8, wherein the insect repellent is N,N-diethyl-meta-toluamide or methyl nonyl ketone.

12. The freshening composition according to claim 8, wherein the preservative is selected from the group consisting of imidazolidinyl urea, diazolidinyl urea, allantoin, and sodium hydroxymethylglycinate.

13. The freshening composition according to claim 8, wherein the antioxidant is selected from the group consisting of butylate hydroxytoluene, ascorbic acid, and tocopherol.

14. The freshening composition according to claim 8, wherein the humectant is selected from the group consisting of glycerol, hexylene glycol, and ethyl-hexylglycerin.

15. The freshening composition according to claim 1, wherein the fragrance release modulator up-regulates the release of the freshening composition or of a component thereof, relative to a control not comprising the fragrance release modulator and being assigned a value of 100%, by at least about 10%, by at least about 20%, by at least about 30%, by at least about 40%, by at least about 50%, by at least about 60%, by at least about 70%, by at least about 80%, by at least about 90%, by at least about 100%, by at least about 110%, by at least about 120%, by at least about 130%, by at least about 140%, by at least about 150%, by at least about 160%, by at least about 170%, by at least about 180%, by at least about 190%, by at least about 200%, by at least about 250%, by at least about 300%, by at least about 400%, by at least about 500%, or by at least about 1,000-3,000% or more.

16. The freshening composition according to claim 1, wherein the fragrance release modulator down-regulates the release of the freshening composition or of a component thereof, relative to a control not comprising the fragrance release modulator and being assigned a value of 100%, by at least about 5%, by at least about 10%, by at least about 15%, by at least about 20%, by at least about 25%, by at least about 30%, by at least about 35%, by at least about 40%, by at least about 45%, by at least about 50%, by at least about 55%, by at least about 60%, by at least about 65%, by at least about 70%, by at least about 75%, by at least about 80%, by at least about 85%, by at least about 90%, by at least about 95% or more.

17. The freshening composition according to claim 1, wherein the ester is selected from the group consisting of an acrylic ester, an acetoacetic ester, an anisic ester, a benzoic ester, an anthranilic ester, an N-methylanthranilic ester, an isovaleric ester, an isobutyric ester, an undecylenic ester, an octanoic ester, an octenoic ester, an octyne carboxylic ester, a caproic ester, a hexenoic ester, a valeric ester, a formic ester, a crotonic ester, a cinnamic ester, a succinic ester, an acetic ester, an salicylic ester, a cyclohexyl alkanoic ester, a stearic ester, a sebacic ester, a decanoic ester, a dodecanoic ester, a lactic ester, a nonanoic ester, a nonenoic ester, a hydroxyhexanoic ester, a phenylacetic ester, a phenoxyacetic ester, a furancarboxylic ester, a propionic ester, a heptanoic ester, a heptin carboxylic ester, a myristic ester, a phenylglycidic ester, a 2-methylbutyric ester, a 3-methylbutyric ester, a butyric ester, a hydroxybutyric ester, a stereoisomer of any preceding ester, and a mixture of any of the preceding esters.

18. The freshening composition according to claim 1, wherein the alcohol is selected from the group consisting of an aliphatic alcohol, a terpene alcohol, an aromatic alcohol, a stereoisomer of any preceding alcohol, and a mixture of any of the preceding alcohols.

19. The freshening composition according to claim 1, wherein the aldehyde is selected from the group consisting of an aliphatic aldehyde, an aromatic aldehyde, a terpene aldehyde, a stereoisomer of any preceding aldehyde, and a mixture of any of the preceding aldehydes.

20. The freshening composition according to claim 1, wherein the ketone is selected from the group consisting of a cyclic ketone, an aromatic ketone, a linear ketone, a stereoisomer of any preceding ketone, and a mixture of any of the preceding ketones.

21. The freshening composition according to claim 1, wherein the acetal is selected from the group consisting of acetaldehyde diethyl acetal, acetaldehyde diamyl acetal, acetaldehyde dihexyl acetal, acetaldehyde propylene glycol acetal, acetaldehyde ethyl cis-3-hexenyl acetal, benzaldehyde glycerin acetal, benzaldehyde propylene glycol acetal, citral dimethyl acetal, citral diethyl acetal, citral propylene glycol acetal, citral ethylene glycol acetal, phenyl acetaldehyde dimethyl acetal, citronellyl methyl acetal, acetaldehyde phenylethyl propyl acetal, hexanal dimethyl acetal, hexanal dihexyl acetal, hexanal propylene glycol acetal, trans-2-hexenal diethyl acetal, trans-2-hexenal propylene glycol acetal, cis-3-hexenal diethyl acetal, heptanal diethyl acetal, heptanal ethylene glycol acetal, octanal dimethyl acetal, nonanal dimethyl acetal, decanal dimethyl acetal, decanal diethyl acetal, 2-methylundecanal dimethyl acetal, citronellal dimethyl acetal, acetoacetate ethyl ethylene glycol acetal, 2-phenylpropanal dimethyl acetal, a stereoisomer of any preceding acetal, and a mixture of any of the preceding acetals.

22. The freshening composition according to claim 1, wherein the phenol is selected from the group consisting of eugenol, isoeugenol, 2-methoxy-4-vinylphenol, thymol, carvacrol, guaiacol, chavicol, a stereoisomer of any preceding phenol, and a mixture of any of the preceding phenols.

23. The freshening composition according to claim 1, wherein the ether is selected from the group consisting of anethole, 1,4-cineole, dibenzyl ether, linalool oxide, limonene oxide, nerol oxide, rose oxide, methylisoeugenol, methyl chavicol, isoamyl phenylethyl ether, β-naphthyl methyl ether, phenyl propyl ether, p-cresyl methyl ether, vanillyl butyl ether, alpha-terpinyl methyl ether, citronellyl ethyl ether, geranyl ethyl ether, rose furan, decyl methyl ether, methyl phenylmethyl ether, a stereoisomer of any preceding ether, and a mixture of any of the preceding ethers.

24. The freshening composition according to claim 1, wherein the lactone is selected from the group consisting of γ-decalactone, δ-decalactone, γ-heptalactone, γ-nonalactone, γ-hexalactone, δ-hexalactone, γ-octalactone, δ-octalactone, γ-undecalactone, δ-undecalactone, δ-dodecalactone, δ-2-decenolactone, methyllactone, 5-hydroxy-δ-undecenoic acid δ-lactone, jasmine lactone, menthalactone, dihydrocoumarin, octahydrocoumarin, 6-methylcoumarin, a stereoisomer of any preceding lactone, and a mixture of any of the preceding lactones.

25. The freshening composition according to claim 1, wherein the furan is selected from the group consisting of 2-methyl furan, 2-ethylfuran, 2,5-diethyltetrahydrofuran, 3-hydroxy-2-methyltetrahydrofuran, 2-(methoxymethyl) furan, 2,3-dihydrofuran, furfural, 5-methylfurfural, 3-(2-furyl)-2-methyl-2-propenal, 5-(hydroxymethyl) furfural, 2,5-dimethyl-4-hydroxy-3 (2H)-furanone (furaneol), 4,5-dimethyl-3-hydroxy-2(5H)-furanone (sotolone), 2-ethyl-4-hydroxy-5-methyl-3(2H)-furanone (homofuraneol), 5-ethyl-3-hydroxy-4-methyl-2(5H)furanone (homosotolone), 3-methyl-1,2-cyclopentanedione (cyclotene), 2(5H)-furanone, 4-methyl-2(5H)-furanone, 5-methyl-2(5H)-furanone, 2-methyl-3(2H)-furanone, 5-methyl-3(2H)-furanone, 2-acetylfuranone, 2-acetyl-5-methylfuran, furfuryl alcohol, methyl 2-furancarboxylate, ethyl 2-furancarboxylate, furfuryl acetate, a stereoisomer of any preceding furan, and a mixture of any of the preceding furans.

26. The freshening composition according to claim 1, wherein the hydrocarbon is selected from the group consisting of α-bisabolene, β-bisabolene, β-caryophyllene, p-cymene, terpinene, terpinolene, cadinene, farnesene, limonene, ocimene, myrcene, α-pinene, β-pinene, 1,3,5-undecatriene, valencene, a stereoisomer of any preceding hydrocarbon, and a mixture of any of the preceding hydrocarbons.

27. The freshening composition according to claim 1, wherein the acid is selected from the group consisting of geranic acid, dodecanoic acid, myristic acid, stearic acid, lactic acid, phenylacetic acid, pyruvic acid, trans-2-methyl-2-pentenoic acid, 2-methyl-cis-3-pentenoic acid, 2-methyl-4-pentenoic acid, cyclohexanecarboxylic acid, a stereoisomer of any preceding acid, and a mixture of any of the preceding acids.

28. The freshening composition according to claim 1, wherein the natural origin fragrance compound is isolated or purified from a natural origin selected from the group consisting of anise, orange, lemon, lime, mandarin, petit grain, bergamot, lemon balm, grapefruit, elemi, olibanum, lemon grass, neroli, marjoram, angelica root, star anise, basil, bay, calamus, chamomile, caraway, cardamon, cassia, cinnamon, pepper, perilla, cypress, oregano, cascarilla, ginger, parsley, pine needle, sage, hyssop, tea tree, mustard, horseradish, clarisage, clove, cognac, coriander, estragon, eucalyptus, fennel, guaiac wood, dill, cajuput, worm seed, pimento, juniper, fenugreek, garlic, laurel, mace, mil, nutmeg, spruce, geranium, citronella, lavender, lavandin, palmarosa, rose, rosemary, sandalwood, oak moth, cider wood, vetiver, linaloe, bois de rose, patchouli, labdanum, cumin, thyme, ylang-ylang, birch, capsicum, celery, tolu balsam, djenne, inmortel, benzoin, jasmine, cassia, tuberose, mignonette, marigold, mimosa, opopanax, orris, vanilla, and licorice.

29. An air freshener device comprising a freshening composition, wherein the freshening composition comprises:
(i) from about 0.1 wt % to about 95 wt % perfume raw material, the perfume raw material comprising one or more ingredients selected from the group consisting of an ester, an alcohol, an aldehyde, a ketone, an acetal, a phenol, an ether, a lactone, a furan, a hydrocarbon, an acid, a natural origin fragrance compound, a synthetic origin fragrance compound, a stereoisomer of any preceding perfume raw material, and a mixture of any of the preceding perfume raw materials;
(ii) from about 1.0 wt % to about 95 wt % of a solvent; and
(iii) from about 2 wt % to about 90 wt % fragrance release modulator having two or more characteristics selected from the group consisting of:
(a) a flash point higher than about 100°F,
(b) a surface tension of less than about 60 mN/m,
(c) a dynamic viscosity from about 0.5 cp to about 100 cp, and
(d) a density from about 600 g/l to about 1,300 g/l;
wherein the fragrance release modulator is selected from the group consisting of an alkyl-ether, an aryl-ether, an alkyl-glycol, an aryl-glycol, an alkyl-carbonate, an aryl-carbonate, an alkyldiol, an alkyl-adipate, an aryl-adipate, an alkyl-benzoate, an aryl-benzoate, an aryl-citrate, an alkyl-laurate, an aryl-laurate, an alkyl-palmitate, an aryl-palmitate, an alkyl-stearate, an aryl-stearate, an alkyl-myristate, an alkyl-succinate, an aryl-succinate, an alkyl-glutarate, an aryl-glutarate, a silicon solvent, a stereoisomer of any preceding fragrance release modulator, and a mixture of any of the preceding fragrance release modulators;
wherein the fragrance release modulator is not dipropylene glycol, not dimethyl ether, and not dimethyl adipate;
wherein the freshening composition comprises the fragrance release modulator in an amount sufficient to control release of the freshening composition or of a component thereof when the freshening composition resides within the air freshener device;

wherein the solvent does not comprise dimethyl adipate;
wherein the perfume raw material, the solvent and the fragrance release modulator are different ingredients;
wherein the freshening composition does not comprise water;
wherein the freshening composition is adapted to have three or more of a characteristic selected from the group consisting of:
(a) a flash point higher than about 100°F,
(b) a surface tension from about 10 mN/m to about 40 mN/m,
(c) a dynamic viscosity from about 1 cp to about 30 cp, and
(d) a density from about 650 g/l to about 1,300 g/l;
and wherein the air freshener device is configured to provide a controllable or customizable rate of release of the freshening composition.

30. The air freshener device according to claim 29, comprising:
(i) less than about 90 wt % fragrance release modulator;
(ii) greater than about 5 wt % perfume raw materials; and
(iii) from about 10 wt % to about 90 wt % solvent.

31. The air freshener device according to claim 30, further comprising less than about 20 wt % of an ingredient having a functional activity and wherein the ingredient having the functional activity is selected from the group consisting of an ingredient having malodor counteracting activity, an ingredient having antimicrobial activity, an insect repellant, a preservative, an antioxidant, a humectant, a UV-blocking agent, a pigment, a dye, a surfactant, an emulsifier, a solubilizer, a polymer, and a buffer.

32. The air freshener device according to claim 31, wherein the ingredient having malodor counteracting activity is cyclodextrin.

33. The air freshener device according to claim 31, wherein the ingredient having antimicrobial activity is selected from the group consisting of a paraben, benzyl alcohol, phenol, cresol, cetrimide, thiomersal, hexylene glycol, 1,2 hexanediol, and phenoxy ethanol.

34. The air freshener device according to claim 31, wherein the insect repellent is N,N-diethyl-meta-toluamide or methyl nonyl ketone.

35. The air freshener device according to claim 31, wherein the preservative is selected from the group consisting of imidazolidinyl urea, diazolidinyl urea, allantoin, and sodium hydroxymethylglycinate.

36. The air freshener device according to claim 9, wherein the antioxidant is selected from the group consisting of butylate hydroxytoluene, ascorbic acid, and tocopherol.

37. The air freshener device according to claim 31, wherein the humectant is selected from the group consisting of glycerol, hexylene glycol, and ethyl-hexylglycerin.

38. The air freshener device according to claim 29, further comprising a delivery system comprising an element in communication or in contact with the freshening composition.

39. The air freshener device according to claim 38, wherein the delivery system is selected from the group consisting of a reed, a plurality of reeds, a stick, a plurality of sticks, a fiber, a plurality of fibers, a wick, a plurality of wicks, a mesh material, a conductive mesh material, a porous substrate, a semi-porous substrate, and a combination of any of the preceding delivery systems.

40. The air freshener device according to claim 38, wherein the delivery system permits the freshening composition to be released into the atmosphere, into the air, or onto a surface.

41. The air freshener device of claim 29, further comprising a reservoir having a functionality selected from the group consisting of accepting a freshening composition, receiving a freshening composition, holding a freshening composition, housing a freshening composition and storing a freshening composition.

42. The air freshener device according to claim 41, wherein the reservoir is selected from the group consisting of a bottle, a vessel, and a container.

43. The air freshener device according to claim 29, further comprising an evaporative assistance element.

44. The air freshener device according to claim 14, wherein the evaporative assistance element is selected from the group consisting of a heater, a fan, an agitator, and a combination of any of the preceding evaporative assistance elements.

45. The air freshener device according to claim 44, further comprising a delivery system, wherein the evaporative assistance element is a heater and wherein the heater is configured to heat the delivery system to a temperature in the range of between about 45° C. to about 75° C.

46. The air freshener device according to claim 29, wherein the perfume raw material comprises a plurality of perfume raw materials.

47. The air freshener device according to claim 46, wherein the plurality of perfume raw materials comprises one or more compounds selected from the group consisting of allyl (3-methylbutoxy) acetate, allyl hexanoate, allyl 3-cyclohexylpropanoate, allyl heptanoate, benzaldehyde, 3-(4-isopropylphenyl)-2-methylpropanal, 2,6-dimethyloct-7-en-2-ol, 1,1-dimethyl-2-phenylethyl acetate, 1,1-dimethyl-2-phenylethyl butyrate, ethyl 2-methylbutanoate, 2-ethyl-3-hydroxy-4H-pyran-4-one, 3-ethoxy-4-hydroxybenzaldehyde, 1,4-dioxacycloheptadecane-5,17-dione, 4-allyl-2-methoxyphenol, ethyl (2-methyl-1,3-dioxolan-2-yl) acetate, methyl (3-oxo-2-pentylcyclopentyl) acetate, hex-2-enal, hexyl acetate, 2-benzylideneoctanal, 4,5,6-trimethylcyclohex-3-ene-1-carbaldehyde, 1-(2,3,8,8-tetramethyl-1,2,3,4,5,6,7,8-octahydronaphthalen-2-yl) ethanone, hex-3-en-1-yl acetate, hex-3-en-1-ol, ethyl 2-methylpentanoate, 5-pentyldihydrofuran-2(3H)-one, 2-phenoxyethyl 2-methylpropanoate, 1-phenylethyl acetate, 2,4-dimethylcyclohex-3-ene-1-carbaldehyde, 5-heptyldihydrofuran-2(3H)-one, and 2-tert-butylcyclohexyl acetate.

48. The air freshener device according to claim 46, wherein the plurality of perfume raw materials comprises one or more compounds selected from the group consisting of 1-(2,3,8,8-tetramethyl-1,2,3,4,5,6,7,8-octahydronaphthalen-2-yl) ethanone, methyl (3-oxo-2-pentylcyclopentyl) acetate, 2-benzylideneoctanal, 1-cedr-8-en-9-ylethanone, 4-tert-butylcyclohexyl acetate, 1,5-dimethyl-1-vinylhex-4-en-1-yl acetate, 3,7-dimethylocta-1,6-dien-3-ol, 1-(2,6,6-trimethylcyclohex-2-en-1-yl) pent-1-en-3-one, 2-isobutyl-4-methyltetrahydro-2H-pyran-4-ol, 1,4-dioxacycloheptadecane-5,17-dione, 2,6-dimethyloct-7-en-2-ol, 3-(4-isopropylphenyl)-2-methylpropanal, hexyl salicylate, 3-(4-ethylphenyl)-2,2-dimethylpropanal, 3-(2-ethylphenyl)-2,2-dimethylpropanal, 3a,4,5,6,7,7a-hexahydro-1H-4,7-methanoinden-6-yl acetate, cedarwood oil, 2-methylundecanal, (2,2-dimethoxyethyl) benzene, undec-10-enal, hex-3-en-1-ol, 3-(1,3-benzodioxol-5-yl)-2-methylpropanal, 1-phenylethyl acetate, 3a,6,6,9a-tetramethyldodecahydronaphtho[2,1-b] furan, allyl (3-methylbutoxy) acetate, and 1-(5,5-dimethylcyclohex-1-en-1-yl) pent-4-en-1-one.

49. The air freshener device according to claim 29, wherein the solvent is selected from the group consisting of an alkyladipate, an aryladipate, an alkyl-glycerol, an aryl-glycerol, an alkyldiol, an aryldiol, an isoparaffine, a silicon, and a mixture of any of the preceding solvents.

50. The air freshener device according to claim 29, wherein the fragrance release modulator is selected from the group consisting of propylene glycol, hexyleneglycol, glycerol, benzyl benzoate, dioctyl adipate, propylene carbonate, dimethyl carbonate, isoamyl laurate, methyl palmitate, methyl stearate, dimethyl succinate, dimethyl glutarate, and a mixture of any of the preceding fragrance release modulators.

51. The air freshener device according to claim 29, wherein the fragrance release modulator up-regulates the release of the freshening composition or of a component thereof, relative to a control not comprising the fragrance release modulator and being assigned a value of 100%, by at least about 10%, by at least about 20%, by at least about 30%, by at least about 40%, by at least about 50%, by at least about 60%, by at least about 70%, by at least about 80%, by at least about 90%, by at least about 100%, by at least about 110%, by at least about 120%, by at least about 130%, by at least about 140%, by at least about 150%, by at least about 160%, by at least about 170%, by at least about 180%, by at least about 190%, by at least about 200%, by at least about 250%, by at least about 300%, by at least about 400%, by at least about 500%, or by at least about 1,000-3,000% or more.

52. The air freshener device according to claim 29, wherein the fragrance release modulator down-regulates the release of the freshening composition or of a component thereof, relative to a control not comprising the fragrance release modulator and being assigned a value of 100%, by at least about 5%, by at least about 10%, by at least about 15%, by at least about 20%, by at least about 25%, by at least about 30%, by at least about 35%, by at least about 40%, by at least about 45%, by at least about 50%, by at least about 55%, by at least about 60%, by at least about 65%, by at least about 70%, by at least about 75%, by at least about 80%, by at least about 85%, by at least about 90%, by at least about 95% or more.

53. The air freshener device according to claim 29, wherein the ester is selected from the group consisting of an acrylic ester, an acetoacetic ester, an anisic ester, a benzoic ester, an anthranilic ester, an N-methylanthranilic ester, an isovaleric ester, an isobutyric ester, an undecylenic ester, an octanoic ester, an octenoic ester, an octyne carboxylic ester, a caproic ester, a hexenoic ester, a valeric ester, a formic ester, a crotonic ester, a cinnamic ester, a succinic ester, an acetic ester, a salicylic ester, a cyclohexyl alkanoic ester, a stearic ester, a sebacic ester, a decanoic ester, a dodecanoic ester, a lactic ester, a nonanoic ester, a nonenoic ester, a hydroxyhexanoic ester, a phenylacetic ester, a phenoxyacetic ester, a furancarboxylic ester, a propionic ester, a heptanoic ester, a heptin carboxylic ester, a myristic ester, a phenylglycidic ester, a 2-methylbutyric ester, a 3-methylbutyric ester, a butyric ester, a hydroxybutyric ester, a stereoisomer of any preceding ester, and a mixture of any of the preceding esters.

54. The air freshener device according to claim 29, wherein the alcohol is selected from the group consisting of an aliphatic alcohol, a terpene alcohol, an aromatic alcohol, a stereoisomer of any preceding alcohol, and a mixture of any of the preceding alcohols.

55. The air freshener device according to claim 29, wherein the aldehyde is selected from the group consisting of an aliphatic aldehyde, an aromatic aldehyde, a terpene aldehyde, a stereoisomer of any preceding aldehyde, and a mixture of any of the preceding aldehydes.

56. The air freshener device according to claim 29, wherein the ketone is selected from the group consisting of a cyclic ketone, an aromatic ketone, a linear ketone, a stereoisomer of any preceding ketone, and a mixture of any of the preceding ketones.

57. The air freshener device according to claim 29, wherein the acetal is selected from the group consisting of acetaldehyde diethyl acetal, acetaldehyde diamyl acetal, acetaldehyde dihexyl acetal, acetaldehyde propylene glycol acetal, acetaldehyde ethyl cis-3-hexenyl acetal, benzaldehyde glycerin acetal, benzaldehyde propylene glycol acetal, citral dimethyl acetal, citral diethyl acetal, citral propylene glycol acetal, citral ethylene glycol acetal, phenyl acetaldehyde dimethyl acetal, citronellyl methyl acetal, acetaldehyde phenylethyl propyl acetal, hexanal dimethyl acetal, hexanal dihexyl acetal, hexanal propylene glycol acetal, trans-2-hexenal diethyl acetal, trans-2-hexenal propylene glycol acetal, cis-3-hexenal diethyl acetal, heptanal diethyl acetal, heptanal ethylene glycol acetal, octanal dimethyl acetal, nonanal dimethyl acetal, decanal dimethyl acetal, decanal diethyl acetal, 2-methylundecanal dimethyl acetal, citronellal dimethyl acetal, acetoacetate ethyl ethylene glycol acetal, 2-phenylpropanal dimethyl acetal, a stereoisomer of any preceding acetal, and a mixture of any of the preceding acetals.

58. The air freshener device according to claim 29, wherein the phenol is selected from the group consisting of eugenol, isoeugenol, 2-methoxy-4-vinylphenol, thymol, carvacrol, guaiacol, chavicol, a stereoisomer of any preceding phenol, and a mixture of any of the preceding phenols.

59. The air freshener device according to claim 29, wherein the ether is selected from the group consisting of anethole, 1,4-cineole, dibenzyl ether, linalool oxide, limonene oxide, nerol oxide, rose oxide, methylisoeugenol, methyl chavicol, isoamyl phenylethyl ether, β-naphthyl methyl ether, phenyl propyl ether, p-cresyl methyl ether, vanillyl butyl ether, alpha-terpinyl methyl ether, citronellyl ethyl ether, geranyl ethyl ether, rose furan, decyl methyl ether, methyl phenylmethyl ether, a stereoisomer of any preceding ether, and a mixture of any of the preceding ethers.

60. The air freshener device according to claim 29, wherein the lactone is selected from the group consisting of γ-decalactone, δ-decalactone, γ-heptalactone, γ-nonalactone, γ-hexalactone, δ-hexalactone, γ-octalactone, δ-octalactone, γ-undecalactone, δ-undecalactone, δ-dodecalactone, δ-2-decenolactone, methyllactone, 5-hydroxy-δ-undecenoic acid δ-lactone, jasmine lactone, menthalactone, dihydrocoumarin, octahydrocoumarin, 6-methylcoumarin, a stereoisomer of any preceding lactone, and a mixture of any of the preceding lactones.

61. The air freshener device according to claim 29, wherein the furan is selected from the group consisting of 2 methyl furan, 2-ethylfuran, 2,5-diethyltetrahydrofuran, 3-hydroxy-2-methyltetrahydrofuran, 2-(methoxymethyl) furan, 2,3-dihydrofuran, furfural, 5-methylfurfural, 3-(2-furyl)-2-methyl-2-propenal, 5-(hydroxymethyl) furfural, 2,5-dimethyl-4-hydroxy-3 (2H)-furanone (furaneol), 4,5-dimethyl-3-hydroxy-2(5H)-furanone (sotolone), 2-ethyl-4-hydroxy-5-methyl-3(2H)-furanone (homofuraneol), 5-ethyl-3-hydroxy-4-methyl-2(5H)furanone (homosotolone), 3-methyl-1,2-cyclopentanedione (cyclotene), 2(5H)-furanone, 4-methyl-2(5H)-furanone, 5-methyl-2(5H)-furanone, 2-methyl-3(2H)-furanone, 5-methyl-3(2H)-furanone, 2-acetylfuranone, 2-acetyl-5-methylfuran, furfuryl alcohol, methyl 2-furancarboxylate, ethyl 2-furancarboxylate, furfuryl acetate, a stereoisomer of any preceding furan, and a mixture of any of the preceding furans.

62. The air freshener device according to claim 29, wherein the hydrocarbon is selected from the group consisting of α-bisabolene, β-bisabolene, β-caryophyllene, p-cymene, terpinene, terpinolene, cadinene, farnesene, limonene, ocimene, myrcene, α-pinene, β-pinene, 1,3,5-undecatriene, valencene, a stereoisomer of any preceding hydrocarbon, and a mixture of any of the preceding hydrocarbons.

63. The air freshener device according to claim 29, wherein the acid is selected from the group consisting of geranic acid, dodecanoic acid, myristic acid, stearic acid, lactic acid, phenylacetic acid, pyruvic acid, trans-2-methyl-2-pentenoic acid, 2-methyl-cis-3-pentenoic acid, 2-methyl-4-pentenoic acid, cyclohexanecarboxylic acid, a stereoisomer of any preceding acid, and a mixture of any of the preceding acids.

64. The air freshener device according to claim 29, wherein the natural origin fragrance compound is isolated or purified from a natural origin selected from the group consisting of anise, orange, lemon, lime, mandarin, petit grain, bergamot, lemon balm, grapefruit, elemi, olibanum, lemon grass, neroli, marjoram, angelica root, star anise, basil, bay, calamus, chamomile, caraway, cardamon, cassia, cinnamon, pepper, perilla, cypress, oregano, cascarilla, ginger, parsley, pine needle, sage, hyssop, tea tree, mustard, horseradish, clarisage, clove, cognac, coriander, estragon, eucalyptus, fennel, guaiac wood, dill, cajuput, worm seed, pimento, juniper, fenugreek, garlic, laurel, mace, mil, nutmeg, spruce, geranium, citronella, lavender, lavandin, palmarosa, rose, rosemary, sandalwood, oak moth, cider wood, vetiver, linaloe, bois de rose, patchouli, labdanum, cumin, thyme, ylang-ylang, birch, capsicum, celery, tolu balsam, djenne, inmortel, benzoin, jasmine, cassia, tuberose, mignonette, marigold, mimosa, opopanax, orris, vanilla, and licorice.

65. The air freshener device according to claim 29, which is a reed diffuser air freshener.

66. The air freshener device according to claim 65, wherein the reed diffuser air freshener comprises a material selected from the group consisting of glass, ceramic, wood, and metal.

67. The air freshener device according to claim 29, which is an energized device.

68. The air freshener device according to claim 67, wherein the energized device is selected from the group consisting of an electrical wall plug-in, a battery-powered air freshener, a fan-based diffuser, a liquid electric pluggable air freshener, an electromechanical actuating diffuser, a heating device, and an energized device comprising a micro-fluidic die having a heater or a piezo crystal.

69. The air freshener device according to claim 68, wherein the energized device is the electrical wall plug-in.

70. The air freshener device according to claim 29, further comprising a wick.

71. The air freshener device according to claim 70, wherein the wick has a cylindrical form or an elongated cube shape.

72. The air freshener device according to claim 70, wherein the density of the wick is in the range from about 0.1 grams/cm³ to about 1.0 grams/cm³.

73. The air freshener device according to claim 70, wherein the porosity of the wick is in the range from about 0.35 grams/cm³ to about 0.85 grams/cm³.

74. The air freshener device according to claim 62, wherein the wick comprises a material selected from the group of polyethylene, high-density polyethylene, and a polyethylene blend.

75. The air freshener device according to claim 29, which is a passive diffuser.

76. The air freshener device according to claim 75, further comprising a breathable membrane.

77. A method for manufacturing an air freshener device comprising a freshening composition, the method comprising the step of contacting a reservoir in an air freshener device with a freshening composition,
wherein the freshening composition comprises:
(i) from about 0.1 wt % to about 95 wt % perfume raw material, the perfume raw material comprising one or more ingredients selected from the group consisting of an ester, an alcohol, an aldehyde, a ketone, an acetal, a phenol, an ether, a lactone, a furan, a hydrocarbon, an acid, a natural origin fragrance compound, a synthetic origin fragrance compound, a stereoisomer of any preceding perfume raw material, and a mixture of any of the preceding perfume raw materials;
(ii) from about 1.0 wt % to about 95 wt % of a solvent; and
(iii) from about 2 wt % to about 90 wt % fragrance release modulator having two or more characteristics selected from the group consisting of:
(a) a flash point higher than about 100°F,
(b) a surface tension of less than about 60 mN/m,
(c) a dynamic viscosity from about 0.5 cp to about 100 cp, and
(d) a density from about 600 g/l to about 1,300 g/l;
wherein the fragrance release modulator is selected from the group consisting of an alkyl ether, an aryl-ether, an alkyl-glycol, an aryl-glycol, an alkyl-carbonate, an aryl-carbonate, an alkyldiol, an alkyl-adipate, an aryl-adipate, an alkyl-benzoate, an aryl-benzoate, an aryl-citrate, an alkyl-laurate, an aryl-laurate, an alkyl-palmitate, an aryl-palmitate, an alkyl-stearate, an aryl-stearate, an aryl-myristate, an alkyl-succinate, an aryl-succinate, an alkyl-glutarate, an aryl-glutarate, a silicon solvent, a stereoisomer of any preceding fragrance release modulator, and a mixture of any of the preceding fragrance release modulators;
wherein the fragrance release modulator is not dipropylene glycol, not dimethyl ether, and not dimethyl adipate;
wherein the freshening composition comprises the fragrance release modulator in an amount sufficient to control release of the freshening composition or of a component thereof when the freshening composition resides within the air freshener device;
wherein the solvent does not comprise dimethyl adipate;
wherein the perfume raw material, the solvent and the fragrance release modulator are different ingredients;
wherein the freshening composition does not comprise water; and
wherein the freshening composition is adapted to have three or more of a characteristic selected from the group consisting of:
(a) a flash point higher than about 100°F,
(b) a surface tension from about 10 mN/m to about 40 mN/m,
(c) a dynamic viscosity from about 1 cp to about 30 cp, and
(d) a density from about 650 g/l to about 1,300 g/l.

78. The method according to claim 77, wherein the fragrance release modulator up-regulates the release of the freshening composition or of a component thereof, relative to a control not comprising the fragrance release modulator and being assigned a value of 100%, by at least about 10%, by at least about 20%, by at least about 30%, by at least about 40%, by at least about 50%, by at least about 60%, by at least about 70%, by at least about 80%, by at least about 90%, by at least about 100%, by at least about 110%, by at least about 120%, by at least about 130%, by at least about 140%, by at least about 150%, by at least about 160%, by at least about 170%, by at least about 180%, by at least about 190%, by at least about 200%, by at least about 250%, by at least about 300%, by at least about 400%, by at least about 500%, or by at least about 1,000-3,000% or more.

79. The method according to claim 20, wherein the fragrance release modulator down-regulates the release of the freshening composition or of a component thereof, relative to a control not comprising the fragrance release modulator and being assigned a value of 100%, by at least about 5%, by at least about 10%, by at least about 15%, by at least about 20%, by at least about 25%, by at least about 30%, by at least about 35%, by at least about 40%, by at least about 45%, by at least about 50%, by at least about 55%, by at least about 60%, by at least about 65%, by at least about 70%, by at least about 75%, by at least about 80%, by at least about 85%, by at least about 90%, by at least about 95% or more.

80. The method according to claim 77, wherein the ester is selected from the group consisting of an acrylic ester, an acetoacetic ester, an anisic ester, a benzoic ester, an anthranilic ester, an N-methylanthranilic ester, an isovaleric ester, an isobutyric ester, an undecylenic ester, an octanoic ester, an octenoic ester, an octyne carboxylic ester, a caproic ester, a hexenoic ester, a valeric ester, a formic ester, a crotonic ester, a cinnamic ester, a succinic ester, an acetic ester, an salicylic ester, a cyclohexyl alkanoic ester, a stearic ester, a sebacic ester, a decanoic ester, a dodecanoic ester, a lactic ester, a nonanoic ester, a nonenoic ester, a hydroxyhexanoic ester, a phenylacetic ester, a phenoxyacetic ester, a furancarboxylic ester, a propionic ester, a heptanoic ester, a heptin carboxylic ester, a myristic ester, a phenylglycidic ester, a 2-methylbutyric ester, a 3-methylbutyric ester, a butyric ester, a hydroxybutyric ester, a stereoisomer of any preceding ester, and a mixture of any of the preceding esters.

81. The method according to claim 77, wherein the alcohol is selected from the group consisting of an aliphatic alcohol, a terpene alcohol, an aromatic alcohol, a stereoisomer of any preceding alcohol, and a mixture of any of the preceding alcohols.

82. The method according to claim 77, wherein the aldehyde is selected from the group consisting of an aliphatic aldehyde, an aromatic aldehyde, a terpene aldehyde, a stereoisomer of any preceding aldehyde, and a mixture of any of the preceding aldehydes.

83. The method according to claim 77, wherein the ketone is selected from the group consisting of a cyclic ketone, an aromatic ketone, a linear ketone, a stereoisomer of any preceding ketone, and a mixture of any of the preceding ketones.

84. The method according to claim 77, wherein the acetal is selected from the group consisting of acetaldehyde diethyl acetal, acetaldehyde diamyl acetal, acetaldehyde dihexyl acetal, acetaldehyde propylene glycol acetal, acetaldehyde ethyl cis-3-hexenyl acetal, benzaldehyde glycerin acetal, benzaldehyde propylene glycol acetal, citral dimethyl acetal, citral diethyl acetal, citral propylene glycol acetal, citral ethylene glycol acetal, phenyl acetaldehyde dimethyl acetal, citronellyl methyl acetal, acetaldehyde phenylethyl propyl acetal, hexanal dimethyl acetal, hexanal dihexyl acetal, hexanal propylene glycol acetal, trans-2-hexenal diethyl acetal, trans-2-hexenal propylene glycol acetal, cis-3-hexenal diethyl acetal, heptanal diethyl acetal, heptanal ethylene glycol acetal, octanal dimethyl acetal, nonanal dimethyl acetal, decanal dimethyl acetal, decanal diethyl acetal, 2-methylundecanal dimethyl acetal, citronellal dimethyl acetal, acetoacetate ethyl ethylene glycol acetal, 2-phenylpropanal dimethyl acetal, a stereoisomer of any preceding acetal, and a mixture of any of the preceding acetals.

85. The method according to claim 20, wherein the phenol is selected from the group consisting of eugenol, isoeugenol, 2-methoxy-4-vinylphenol, thymol, carvacrol, guaiacol, chavicol, a stereoisomer of any preceding phenol, and a mixture of any of the preceding phenols.

86. The method according to claim 77, wherein the ether is selected from the group consisting of anethole, 1,4-cineole, dibenzyl ether, linalool oxide, limonene oxide, nerol oxide, rose oxide, methylisoeugenol, methyl chavicol, isoamyl phenylethyl ether, β-naphthyl methyl ether, phenyl propyl ether, p-cresyl methyl ether, vanillyl butyl ether, alpha-terpinyl methyl ether, citronellyl ethyl ether, geranyl ethyl ether, rose furan, decyl methyl ether, methyl phenylmethyl ether, a stereoisomer of any preceding ether, and a mixture of any of the preceding ethers.

87. The method according to claim 77, wherein the lactone is selected from the group consisting of γ-decalactone, δ-decalactone, γ-heptalactone, γ-nonalactone, γ-hexalactone, δ-hexalactone, γ-octalactone, δ-octalactone, γ-undecalactone, δ-undecalactone, δ-dodecalactone, δ-2-decenolactone, methyllactone, 5-hydroxy-8-undecenoic acid δ-lactone, jasmine lactone, menthalactone, dihydrocoumarin, octahydrocoumarin, 6-methylcoumarin, a stereoisomer of any preceding lactone, and a mixture of any of the preceding lactones.

88. The method according to claim 77, wherein the furan is selected from the group consisting of 2-methyl furan, 2-ethylfuran, 2,5-diethyltetrahydrofuran, 3-hydroxy-2-methyltetrahydrofuran, 2-(methoxymethyl) furan, 2,3-dihydrofuran, furfural, 5-methylfurfural, 3-(2-furyl)-2-methyl-2-propenal, 5-(hydroxymethyl) furfural, 2,5-dimethyl-4-hydroxy-3(2H)-furanone (furaneol), 4,5-dimethyl-3-hydroxy-2(5H)-furanone (sotolone), 2-ethyl-4-hydroxy-5-methyl-3(2H)-furanone (homofuraneol), 5-ethyl-3-hydroxy-4-methyl-2(5H)furanone (homosotolone), 3-methyl-1,2-cyclopentanedione (cyclotene) 3-methyl-1,2-cyclopentanedione (cyclotene), 2(5H)-furanone, 4-methyl-2(5H)-furanone, 5-methyl-2(5H)-furanone, 2-methyl-3(2H)-furanone, 5-methyl-3(2H)-furanone, 2-acetylfuranone, 2-acetyl-5-methylfuran, furfuryl alcohol, methyl 2-furancarboxylate, ethyl 2-furancarboxylate, furfuryl acetate, a stereoisomer of any preceding furan, and a mixture of any of the preceding furans.

89. The method according to claim 77, wherein the hydrocarbon is selected from the group consisting of α-bisabolene, β-bisabolene, β-caryophyllene, p-cymene, terpinene, terpinolene, cadinene, farnesene, limonene, ocimene, myrcene, α-pinene, β-pinene, 1,3,5-undecatriene, valencene, a stereoisomer of any preceding hydrocarbon, and a mixture of any of the preceding hydrocarbons.

90. The method according to claim 77, wherein the acid is selected from the group consisting of geranic acid, dodecanoic acid, myristic acid, stearic acid, lactic acid, phenylacetic acid, pyruvic acid, trans-2-methyl-2-pentenoic acid, 2-methyl-cis-3-pentenoic acid, 2-methyl-4-pentenoic acid, cyclohexanecarboxylic acid, a stereoisomer of any preceding acid, and a mixture of any of the preceding acids.

91. The method according to claim 77, wherein the natural origin fragrance compound is isolated or purified from a natural origin selected from the group consisting of anise, orange, lemon, lime, mandarin, petit grain, bergamot, lemon balm, grapefruit, elemi, olibanum, lemon grass, neroli, marjoram, angelica root, star anise, basil, bay, calamus, chamomile, caraway, cardamon, cassia, cinnamon, pepper, perilla, cypress, oregano, cascarilla, ginger, parsley, pine needle, sage, hyssop, tea tree, mustard, horseradish, clarisage, clove, cognac, coriander, estragon, eucalyptus, fennel, guaiac wood, dill, cajuput, worm seed, pimento, juniper, fenugreek, garlic, laurel, mace, mil, nutmeg, spruce, geranium, citronella, lavender, lavandin, palmarosa, rose, rosemary, sandalwood, oak moth, cider wood, vetiver, linaloe, bois de rose, patchouli, labdanum, cumin, thyme, ylang-ylang, birch, capsicum, celery, tolu balsam, djenne, inmortel, benzoin, jasmine, cassia, tuberose, mignonette, marigold, mimosa, opopanax, orris, vanilla, and licorice.

92. The method according to claim 77, wherein the perfume raw material comprises one or more compounds selected from the group consisting of allyl (3-methylbutoxy) acetate, allyl hexanoate, allyl 3-cyclohexylpropanoate, allyl heptanoate, benzaldehyde, 3-(4-isopropylphenyl)-2-methylpropanal, 2,6-dimethyloct-7-en-2-ol, 1,1-dimethyl-2-phenylethyl acetate, 1,1-dimethyl-2-phenylethyl butyrate, ethyl 2-methylbutanoate, 2-ethyl-3-hydroxy-4H-pyran-4-one, 3-ethoxy-4-hydroxybenzaldehyde, 1,4-dioxacycloheptadecane-5,17-dione, 4-allyl-2-methoxyphenol, ethyl (2-methyl-1,3-dioxolan-2-yl) acetate, methyl (3-oxo-2-pentylcyclopentyl) acetate, hex-2-enal, hexyl acetate, 2-benzylideneoctanal, 4,5,6-trimethylcyclohex-3-ene-1-carbaldehyde, 1-(2,3,8,8-tetramethyl-1,2,3,4,5,6,7,8-octahydronaphthalen-2-yl) ethanone, hex-3-en-1-yl acetate, hex-3-en-1-ol, ethyl 2-methylpentanoate, 5-pentyldihydrofuran-2 (3H)-one, 2-phenoxyethyl 2-methylpropanoate, 1-phenylethyl acetate, 2,4-dimethylcyclohex-3-ene-1-carbaldehyde, 5-heptyldihydrofuran-2(3H)-one, and 2-tert-butylcyclohexyl acetate.

93. The method according to claim 77, wherein the perfume raw material comprises one or more compounds selected from the group consisting of 1-(2,3,8,8-tetramethyl-1,2,3,4,5,6,7,8-octahydronaphthalen-2-yl) ethanone, methyl (3-oxo-2-pentylcyclopentyl) acetate, 2-benzylideneoctanal, 1-cedr-8-en-9-ylethanone, 4-tert-butylcyclohexyl acetate, 1,5-dimethyl-1-vinylhex-4-en-1-yl acetate, 3,7-dimethylocta-1,6-dien-3-ol, 1-(2,6,6-trimethylcyclohex-2-en-1-yl) pent-1-en-3-one, 2-isobutyl-4-methyltetrahydro-2H-pyran-4-ol, 1,4-dioxacycloheptadecane-5,17-dione, 2,6-dimethyl-oct-7-en-2-ol, 3-(4-isopropylphenyl)-2-methylpropanal, hexyl salicylate, 3-(4-ethylphenyl)-2,2-dimethylpropanal, 3-(2-ethylphenyl)-2,2-dimethylpropanal, 3a,4,5,6,7,7a-hexahydro-1H-4,7-methanoinden-6-yl acetate, cedarwood oil, 2-methylundecanal, (2,2-dimethoxyethyl) benzene, undec-10-enal, hex-3-en-1-ol, 3-(1,3-benzodioxol-5-yl)-2-methylpropanal, 1-phenylethyl acetate, 3a, 6,6,9a-tetramethyldodecahydronaphtho[2,1-b] furan, allyl (3-methylbutoxy) acetate, and 1-(5,5-dimethylcyclohex-1-en-1-yl) pent-4-en-1-one.

94. The method according to claim 77, wherein the freshening composition further comprises less than 50 wt % of an ingredient having a functional activity and wherein the ingredient having the functional activity is selected from the group consisting of an ingredient having malodor counteracting activity, an ingredient having antimicrobial activity, an insect repellant, a preservative, an antioxidant, a humectant, a UV-blocking agent, a pigment, a dye, a surfactant, an emulsifier, a solubilizer, a polymer, and a buffer.

95. The method according to claim 94, wherein the ingredient having malodor counteracting activity is cyclodextrin.

96. The method according to claim 94, wherein the ingredient having antimicrobial activity is selected from the group consisting of a paraben, benzyl alcohol, phenol, cresol, cetrimide, thiomersal, hexylene glycol, 1,2 hexanediol, and phenoxy ethanol.

97. The method according to claim 94, wherein the insect repellent is N,N-diethyl-meta-toluamide or methyl nonyl ketone.

98. The method according to claim 94, wherein the preservative is selected from the group consisting of imidazolidinyl urea, diazolidinyl urea, allantoin, and sodium hydroxymethylglycinate.

99. The method according to claim 94, wherein the antioxidant is selected from the group consisting of butylate hydroxytoluene, ascorbic acid, and tocopherol.

100. The method according to claim 94, wherein the humectant is selected from the group consisting of glycerol, hexylene glycol, and ethyl-hexylglycerin.

101. The method according to claim 77, wherein the air freshener device is selected from the group consisting of a sprayable device, a capillary wicking device, a membrane diffusing device, a steam-diffusing device, an energized device, a heating device, a device comprising a delivery system, a device powered by a chemical reaction, a passive air diffuser device, and a device comprising an evaporative assistance element.

102. The method according to claim 101, wherein the delivery system is selected from the group consisting of a wick, a plurality of wicks, a stick, a plurality of sticks, a reed, a plurality of reeds, a fiber, a plurality of fibers, a mesh, a conductive mesh, a membrane, a porous substrate, a semi-porous substrate, and a combination of any of the preceding delivery systems.

* * * * *

UNITED STATES PATENT AND TRADEMARK OFFICE
CERTIFICATE OF CORRECTION

PATENT NO. : 11,806,448 B2
APPLICATION NO. : 16/524697
DATED : November 7, 2023
INVENTOR(S) : Florin-Iosif Vlad and Austin Howard Page 1 of 1

It is certified that error appears in the above-identified patent and that said Letters Patent is hereby corrected as shown below:

In the Specification

In Column 20, Line 35, please delete "0, 50 wt" and insert --◊, 50 wt--.
In Column 20, Line 39, please delete "Q, 50 wt" and insert --□, 50 wt--.
In Column 22, Line 23, please delete "0, 50 wt" and insert --◊, 50 wt--.
In Column 40, Line 48, please delete "6-damascone" and insert --δ-damascone--.
In Column 41, Line 53, please delete "δ-methylcoumarin" and insert --6-methylcoumarin--.
In Column 51, Line 24, please delete "2,6-dimethyl oct-7-en-2-ol" and insert --2,6-dimethyloct-7-en-2-ol--.

In the Claims

In Column 99, Lines 37-38, please delete "5-hydroxy-δ-undecenoic acid δ-lactone" and insert --5-hydroxy-8-undecenoic acid δ-lactone--.
In Column 101, Line 47, please delete "claim 9" and insert --claim 31--.
In Column 102, Line 12, please delete "claim 14" and insert --claim 43--.
In Column 104, Lines 49-50, please delete "5-hydroxy-δ-undecenoic acid ō-lactone" and insert --5-hydroxy-8-undecenoic acid δ-lactone--.
In Column 106, Line 1, please delete "claim 62" and insert --claim 70--.
In Column 107, Line 16, please delete "claim 20" and insert --claim 77--.
In Column 108, Line 16, please delete "claim 20" and insert --claim 77--.

Signed and Sealed this
Fourth Day of March, 2025

Coke Morgan Stewart
*Acting Director of the United States Patent and Trademark Office*